United States Patent
Maruthachalam et al.

(10) Patent No.: US 11,390,686 B2
(45) Date of Patent: Jul. 19, 2022

(54) HER3 BINDING AGENTS AND USES THEREOF

(71) Applicant: University of Saskatchewan, Saskatoon (CA)

(72) Inventors: Bharathikumar Vellalore Maruthachalam, Saskatoon (CA); Ayman Elsayed Mohammad, Saskatoon (CA); Jianghai Liu, Saskatoon (CA); Humphrey Fonge, Saskatoon (CA); Kris Barreto, Saskatoon (CA); Clarence Ronald Geyer, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 87 days.

(21) Appl. No.: 16/637,201

(22) PCT Filed: Aug. 9, 2018

(86) PCT No.: PCT/CA2018/050965
§ 371 (c)(1),
(2) Date: Feb. 6, 2020

(87) PCT Pub. No.: WO2019/028555
PCT Pub. Date: Feb. 14, 2019

(65) Prior Publication Data
US 2020/0207868 A1    Jul. 2, 2020

Related U.S. Application Data

(60) Provisional application No. 62/697,288, filed on Jul. 12, 2018, provisional application No. 62/543,132, filed on Aug. 9, 2017.

(51) Int. Cl.
*C07K 16/00* (2006.01)
*G01N 33/573* (2006.01)
*C07K 16/32* (2006.01)
*A61K 47/64* (2017.01)
*A61K 9/00* (2006.01)
*A61K 49/00* (2006.01)
*G01N 33/574* (2006.01)

(52) U.S. Cl.
CPC .......... *C07K 16/32* (2013.01); *A61K 9/0019* (2013.01); *A61K 47/6415* (2017.08); *A61K 49/0058* (2013.01); *G01N 33/574* (2013.01); *C07K 2317/31* (2013.01); *C07K 2317/55* (2013.01); *C07K 2317/565* (2013.01); *C07K 2317/622* (2013.01); *C07K 2317/626* (2013.01); *C07K 2317/92* (2013.01); *G01N 2333/705* (2013.01)

(58) Field of Classification Search
CPC .............. C07K 16/32; C07K 2317/55; C07K 2317/565; C07K 2317/626; C07K 16/005; G01N 33/574; G01N 2333/705; G01N 2333/71; A61K 51/1045; A61P 35/00
See application file for complete search history.

(56) References Cited

U.S. PATENT DOCUMENTS

| | | | |
|---|---|---|---|
| 8,580,263 B2 | 11/2013 | Adams et al. | |
| 8,784,821 B1 | 7/2014 | Kufer et al. | |
| 9,127,065 B2 * | 9/2015 | Chardes | C07K 16/32 |
| 2005/0244403 A1 | 11/2005 | Lazar et al. | |

FOREIGN PATENT DOCUMENTS

| | | | |
|---|---|---|---|
| WO | 2011/022727 A2 | | 2/2011 |
| WO | WO 2011022727 | * | 2/2011 |

OTHER PUBLICATIONS

Meulendijks et al, Clin Cancer Res 22:877-85, 2015 (Year: 2015).*
Van Dongen, Gams et al., "PET imaging with radiolabeled antibodies and tyrosine kinase inhibitors: Immuno-PET and TKI-PET", Tumor Biol. 2012; 33: pp. 607-615.
Vahrmeijer, AL et al., Image-guided cancer surgery using near-infrared fluorescence. Nat Rev Clin Oncol., Sep. 2013; 10(9), pp. 507-518.
Zalevsky, J. et al., "Enhanced antibody half-life improves in vivo activity", Nat Biotechnol. Feb. 2010, vol. 28 No. 2, pp. 157-159.
Beck, A. et al., "Therapeutic Fc-fusion proteins and peptides as successful alternatives to antibodies", mAbs 2011; 3: pp. 415-416.
Behr, TM. et al., "Trastuzumab and breast cancer", N Engl J Med. 2001; 345: 995-996.
Bensch, F. et al., "(89)Zr-lumretuzumab PET imaging before and during HER3 antibody lumretuzumab treatment in patients with solid tumors", Clin Cancer Res. 2017; 23: 6128-37.
Ocana, A. et al., "HER3 overexpression and survival in solid tumors: A meta-analysis", J Natl Cancer Inst. 2013; 105: 266-73.
Hayashi, M. et al., "High expression of HER3 is associated with a decreased survival in gastric cancer", Clin Cancer Res. 2008; 14: 7843-9.
Ledel, F. et al. "HER3 expression in patients with primary colorectal cancer and corresponding lymph node metastases related to clinical outcome", Eur J Cancer. 2014; 50: 656-62.
Tanner, B. et al., "ErbB-3 predicts survival in ovarian cancer", J Clin Oncol. 2006; 24: 4317-23.
Müller-Tidow, C. et al., "Identification of metastasis-associated receptor tyrosine kinases in non-small cell lung cancer", Cancer Res. 2005; 65: 1778-82.

(Continued)

*Primary Examiner* — Lei Yao
(74) *Attorney, Agent, or Firm* — Bereskin & Parr LLP/S.E.N.C.R.L., s.r.l.; Ainslie Parsons; Carmela De Luca

(57) ABSTRACT

The disclosure is directed to antibodies and binding fragments thereof that specifically bind HER3. The disclosure is further directed to immunoconjugates comprising the antibodies and binding fragments thereof that specifically bind HER3. The disclosure is also directed to uses of the antibodies, binding fragments thereof and immunoconjugates for detecting HER3-expressing cells and for treating HER3-expressing cancer.

14 Claims, 36 Drawing Sheets

Specification includes a Sequence Listing.

(56) References Cited

OTHER PUBLICATIONS

Sergina, N.V. et al., "Escape from HER-family tyrosine kinase inhibitor therapy by the kinase-inactive HER3", Nature. 2007; 445: 437-441.

Huang, X. et al., "Heterotrimerization of the growth factor receptors erbB2, erbB3, and insulin-like growth factor-I receptor in breast cancer cells resistant to herceptin", Cancer Res. 2010; 70: 1204-14.

"Immuno positron emission tomography study of GSK2849330 in subjects with human epidermal growth factor receptor 3-positive solid tumors", downloaded from https://clinicaltrials.gov/ct2/show/NCT02345174, 8 pages.

Lockhart, A.C. et al. "Phase 1 evaluation of (64)Cu-DOTA-patritumab to assess dosimetry, apparent receptor occupancy, and safety in subjects with advanced solid tumors", Mol Imaging Biol. Jun. 2016; 18: 446-453.

Yuan, Q. et al. "Immuno-PET imaging of HER3 in a model in which HER3 signaling plays a critical role", PLoS One. 2015; 10: e0143076, pp. 1-16.

Orlova, A. et al., "Imaging of HER3-expressing xenografts in mice using a (99m)Tc(CO)3-HEHEHE-Z(HER3:08699) affibody molecule", Eur J Nucl Med Mol Imaging. 2014; 41: 1450-1459.

Rosestedt, M. et al., "Affibody-mediated PET imaging of HER3 expression in malignant tumours", Sci Rep. 2015; 5:15226, pp. 1-12.

Da Pieve, C. et al., "Efficient [18F]AlF radiolabeling of Z(HER3:8698) affibody molecule for imaging of HER3 positive tumors", Bioconjug Chem. 2016; 27, pp. 1839-1849.

Maruthachalam, B.V. et al., "A single-framework synthetic antibody library containing a combination of canonical and variable complementarity determining regions", Chembiochem. 2017; 18: 2247-2259.

Garner, A.P. et al., "An antibody that locks HER3 in the inactive conformation inhibits tumor growth driven by HER2 or neuregulin", Cancer Res. 2013; 73: 6024-35.

Klein, J.S. et al., "Examination of the contributions of size and avidity to the neutralization mechanisms of the anti-HIV antibodies b12 and 4E10", Proc Natl Acad Sci USA. 2009; 106 :7385-90.

Torres, M. et al., "The immunoglobulin heavy chain constant region affects kinetic and thermodynamic parameters of antibody variable region interactions with antigen", J Biol Chem. 2007; 282: 13917-13927.

Pritsch, O. et al., "Can immunoglobulin C(H)1 constant region domain modulate antigen binding affinity of antibodies?", J Clin Invest. 1996; 98: 2235-43.

Olafsen, T. et al., "Characterization of engineered anti-p185HER-2 (scFv-CH3)2 antibody fragments (minibodies) for tumor targeting", Protein Eng Des Sel. 2004; 17: 315-23.

Williams, L.E. et al., "Numerical selection of optimal tumor imaging agents with application to engineered antibodies", Cancer Biother Radiopharm. 2001; 16: 25-35.

Begent, R.H.J. et al., "Clinical evidence of efficient tumor targetting based on single-chain Fv antibody selected from a combinatorial library", Nat Med. 1996; 2: 979-84.

Pavlinkova, G. et al. "Pharmacokinetics and biodistribution of engineered single-chain antibody constructs of MAb CC49 in colon carcinoma xenografts", J Nucl Med. 1999; 40: 1536-1546.

Schneider, D.W. et al., "In vivo biodistribution, PET imaging, and tumor accumulation of 86Y- and 111In-antimindin/RG-1, engineered antibody fragments in LNCaP tumor-bearing nude mice", J Nucl Med. 2009; 50, pp. 435-443.

Malm, M. et al., "Inhibiting HER3-mediated tumor cell growth with affibody molecules engineered to low picomolar affinity by position-directed error-prone PCR-like diversification", PLoS One, 2013; 8: e62791, pp. 1-13.

Malm, M. et al., "Targeting HER3 using mono- and bispecific antibodies or alternative scaffolds", mABS, 2016, vol. 8 No. 7, pp. 1195-1209.

Dudgeon, K. et al., "General strategy for the generation of human antibody variable domains with increased aggregation resistance", PNAS, Jul. 2012, pp. 10879-10884.

Bostrom, J. et al., "Variants of the Antibody Herceptin That Interact with HER2 and VEGF at the Antigen Binding Site", Science, Mar. 2009, vol. 323, pp. 1610-1614.

Geyer C.R. et al., "Recombinant Antibodies and In Vitro Selection Technologies", Antibody Methods and Protocols, Methods in Molecular Biology, vol. 901, Jun. 2012, pp. 11-32; DOI 10.1007/978-1-61779-931-0_2.

Mahon C.M. et al., "Comprehensive Interrogation of a Minimalist Synthetic CDR-H3 Library and Its Ability to Generate Antibodies with Therapeutic Potential", J. Mol. Biol. 2013, 425, pp. 1712-1730; http://dx.doi.org/10.1016/j.jmb.2013.02.015.

Nixon A.E. et al., "Drugs derived from phage display, From candidate identification to clinical practice", mAbs 6:1, Jan./Feb. 2014, pp. 73-85; DOI: 10.4161/mabs27240.

Frenzel A. et al., "Phage display-derived human antibodies in clinical development and therapy", mAbs 2016, 8:7 pp. 1177-1194; DOI: 10.1080/19420862.2016.1212149.

Michnick S.W. et al., "Submitting antibodies to binding arbitration", Nature Chemical Biology, vol. 4, No. 6, Jun. 2008, pp. 326-329.

Sidhu S.S. "Antibodies for all: The case for genome-wide affinity reagents", FEBS Letters, vol. 586 issue 17, Aug. 14, 2012, pp. 2778-2779; http://doi.org/10.1016/j.febslet.2012.05.044.

Shim H., "Therapeutic Antibodies by Phage Display", Current Pharmaceutical Design, vol. 22, No. 43, 2016, pp. 6538-6559; doi:10.2174/1381612822666160923113714.

Ponsel D. et al., "High Affinity, Developability and Functional Size: The Holy Grail of Combinatorial Antibody Library Generation", Molecules 2011, 16, pp. 3675-3700; doi:10.3390/molecules16053675.

Inbar N.H. et al., "Selection of antibodies from synthetic antibody libraries", Archives of Biochemistry and Biophysics, 2012, 526, pp. 87-98.

Adams, J.J. et al., "Synthetic antibody technologies", Current Opinion Structural Biology, 2014, 24, pp. 1-9; http://dx.doi.org/10.106/j.sbi.2013.11.003.

Miersch, S. "Synthetic antibodies: Concepts, potential and practical considerations", Methods 2012, 57, pp. 486-498.

Carter, P. et al., "Humanization of an anti-p185[HER2] antibody for human cancer therapy", Proc. Natl. Acad. Sci. USA, vol. 89, May 1992, pp. 4285-4289.

Na, H. et al., "A high-throughput pipeline for the production of synthetic antibodies for analysis of ribonucleoprotein complexes", RNA 2016, 22, pp. 636-655.

Fellouse, F. A. et al., "High-throughput Generation of Synthetic Antibodies from Highly Functional Minimalist Phage-displayed Libraries", J. Mol. Biol. 2007, 373, pp. 924-940.

Persson, H. et al., "CDR-H3 Diversity Is Not Required for Antigen Recognition by Synthetic Antibodies", J. Mol. Biol. 2013, 425, pp. 803-811.

Lee, C.V. et al., "High-affinity Human Antibodies from Phage-displayed Synthetic Fab Libraries with a Single Framework Scaffold", J. Mol. Biol. 2004, 340, pp. 1073-1093.

Kelley, R.F. et al., "Antigen Binding Thermodynamics and Antiproliferative Effects of Chimeric and Humanized anti-p185(HER2) Antibody Fab Fragments", 1992, 31, pp. 5434-5441.

Eigenbrot, C. et al., "X-ray Structures of the Antigen-binding Domains from Three Variants of Humanized anti-p185 (HER2) Antibody 4D5 and Comparison with Molecular Modeling", J. Mol. Biol. 1993, 229, pp. 969-995.

Martin, A.C. et al., "Structural Families in Loops of Homologous Proteins: Automatic Classification, Modelling and Application to Antibodies", J. Mol. Biol. 1996, 263, pp. 800-815.

Al-Lazikani, B. et al., "Standard Conformations for the Canonical Structures of Immunoglobulins", J. Mol. Biol. 1997, 273, pp. 927-948.

Morea, V. et al., "Conformations of the Third Hypervariable Region in the VH Domain of Immunoglobulins", J. Mol. Biol. 1998, 275, pp. 269-294.

(56) References Cited

OTHER PUBLICATIONS

Rothe, C. et al., "The Human Combinatorial Antibody Library HuCAL GOLD Combines Diversification of All Six CDRs According to the Natural Immune System with a Novel Display Method for Efficient Selection of High-Affinity Antibodies", J. Mol. Biol. 2008, 376, 1182-1200.

Prassler, J. et al., "HuCAL PLATINUM, a Synthetic Fab Library Optimized for Sequence Diversity and Superior Performance in Mammalian Expression Systems," J. Mol. Biol. 2011, 413, pp. 261-278.

Tiller, T. et al. "A fully synthetic human Fab antibody library based on fixed VH/VL framework pairings with favorable biophysical properties", mAbs 2013, 5, pp. 445-470.

Chothia, C. et al., "Structural Repertoire of the Human V(H) Segments", J. Mol. Biol. 1992, 227, pp. 799-817.

Knappik, A. et al., "Fully Synthetic Human Combinatorial Antibody Libraries (HuCAL) Based on Modular Consensus Frameworks and CDRs Randomized with Trinucleotides", J. Mol. Biol. 2000, 296, 57-86.

North, B. et al., "A New Clustering of Antibody CDR Loop Conformations", J. Mol. Biol. 2011, 406, pp. 228-256.

Zemlin, M. et al., "Expressed Murine and Human CDR-H3 Intervals of Equal Length Exhibit Distinct Repertoires that Differ in their Amino Acid Composition and Predicted Range of Structures", J. Mol. Biol. 2003, 334, pp. 733-749.

Lee, C.V. et al., "Bivalent antibody phage display mimics natural immunoglobulin", J. Immunol. Methods 2004, 284, pp. 119-132.

Ma, J. et al., "Targeting of erbB3 receptor to overcome resistance in cancer treatment", Mol. Cancer 2014, 13,105, pp. 1-9.

Zhang, K. et al., "Synchronized Targeting of Notch and ERBB Signaling Suppresses Melanoma Tumor Growth through Inhibition of Notch1 and ERBB3", J. Invest. Dermatol. 2016, 136, pp. 464-472.

Mirschberger, C. et al., "RG7116, a Therapeutic Antibody That Binds the Inactive HER3 Receptor and Is Optimized for Immune Effector Activation", Cancer Res. 2013, 73, pp. 5183-5194.

Terwisscha Van Scheltinga, A. GT et al. "ImmunoPET and biodistribution with human epidermal growth factor receptor 3 targeting antibody (89)Zr-RG7116", mAbs 2014, 6, pp. 1051-1058.

Goldenberg, D.M. et al., "Clinical Studies of Cancer Radioimmunodetection with Carcinoembryonic Antigen Monoclonal Antibody Fragments Labeled with (123)I or (99m)Tc(1)", Cancer Res. 1990, 50, pp. 909-921.

Kunkel, T.A. et al., "Rapid and efficient site-specific mutagenesis without phenotypic selection", Methods in Enzymol. 1987, 154, pp. 367-382.

Rajan, S. et al., "Simplified Synthetic Antibody Libraries", Methods Enzymol. 2012, vol. 502, pp. 3-23.

duManoir, J.M. et al., "Strategies for Delaying or Treating In vivo Acquired Resistance to Trastuzumab in Human Breast Cancer Xenografts", Clin Cancer Res. 2006, 12, pp. 904-916.

Dahabieh, M.S. et al. "Direct non-productive HIV-1 infection in a T-cell line is driven by cellular activation state and NFκB", Retrovirology 2014, 11, pp. 1-17.

Hornsby, M. et al. "A High Through-put Platform for Recombinant Antibodies to Folded Proteins", Mol. Cell. Proteomics 2015, 14, pp. 2833-2847.

Tang, Y. et al., "Imaging of HER2/neu-positive BT-474 human breast cancer xenografts in athymic mice using (111)In-trastuzumab (Herceptin) Fab fragments", Nucl. Med. Biol. 2005, 32, pp. 51-58.

Covell, D.G. et al., "Pharmacokinetics of Monoclonal Immunoglobulin G(1), F(ab')2, and Fab' in Mice", Cancer Res. 1986,46, pp. 3969-3978.

Sela-Culang, I. et al., "The structural basis of antibody-antigen recognition", Front Immunol. 2013, 8, pp. 1-13.

MacKenzie, C.R. et al., "Analysis by Surface Plasmon Resonance of the Influence of Valence on the Ligand Binding Affinity and Kinetics of an Anti-carbohydrate Antibody", J Biol Chem. 1996, 19, 1527-33.

Wu, A.M., "Engineered antibodies for molecular imaging of cancer", Jan. 2014, 65(1), pp. 139-147.

Freise, A.C. et al., "In vivo Imaging with Antibodies and Engineered Fragments", Mol Immunol. Oct. 2015, 67, pp. 142-152.

Colombo, I. et al., "Molecular imaging in drug development: Update and challenges for radiolabeled antibodies and nanotechnology", Methods 130, 2017, pp. 23-35.

Abbineni, G. et al., "Evolutionary Selection of New Breast Cancer Cell-Targeting Peptides and Phages with the Cell-Targeting Peptides Fully Displayed on the Major Coat and Their Effects on Actin Dynamics during Cell Internalization", 2010, vol. 7, No. 5, pp. 1629-1642.

Sunderland, K.S. et al., "Phage-Enabled Nanomedicine: From Probes to Therapeutics in Precision Medicine", Angew. Chem. Int. Ed. 2017, 56, 1964-92.

Burkovitz, A. et al., "Understanding differences between synthetic and natural antibodies can help improve antibody engineering", MABS 2016, vol. 8, No. 2, pp. 278-287.

Ramaraj, T., et al., "Antigen-antibody interface properties: Composition, residue interactions, and features of 53 non-redundant structures", Biochim Biophys Acta., Mar. 2012, 1824(3), pp. 520-532.

\* cited by examiner

```
                        CDRL1                    CDRL2
              10        20        30        40        50        60
Mu4D5      DIVMTQSHKFMSTSVGDRVSITCKASQDVNTAVAWYQQKPGHSPKLLIYSASFRYTGVPD
Hu4D5-1    DIQMTQSPSSLSASVGDRVTITCRASQDVNTAVAWYQQKPGKAPKLLIYSASFLESGVPS
Hu4D5-8    DIQMTQSPSSLSASVGDRVTITCRASQDVNTAVAWYQQKPGKAPKLLIYSASFLYSGVPS
Library-F  DIQMTQSPSSLSASVGDRVTITCRASQSVSSAVAWYQQKPGKAPKLLIYSASSLYSGVPS
Library-S  DIQMTQSPSSLSASVGDRVTITCRASQGISNYLAWYQQKPGKAPKLLIYAASSLQSGVPS
           ** ****  .:*:******:***:***.:.. ;*******:;******:**  ;***.

CDRL3
              70        80        90        100     SEQ ID NO:
Mu4D5      RFTGNRSGTDFTFTISSVQAEDLAVYYCQQHYTTPPTFGGGTKLEIK    101
Hu4D5-1    RFSGSGSGTDFTLTISSLQPEDFATYYCQQHYTTPPTFGQGTKVEIK    102
Hu4D5-8    RFSGSRSGTDFTLTISSLQPEDFATYYCQQHYTTPPTFGQGTKVEIK    103
Library-F  RFSGSRSGTDFTLTISSLQPEDFATYYCQQ------TFGQGTKVEIK    104
Library-S  RFSGSRSGTDFTLTISSLQPEDFATYYCQQ----PLTFGQGTKVEIK    105
           **:*. ******:****:* **:*.*****       *** ***:***
```

B)

```
                        CDRH1                    CDRH2
              10        20        30        40        50 a
Mu4D5      EVQLQQSGPELVKPGASLKLSCTASGFNIKDTYIHWVKQRPEQGLEWIGRIYPTNGYTRY
Hu4D5-1    EVQLVESGGGLVQPGGSLRLSCAASGFNIKDTYIHWVRQAPGKGLEWVARIYPTNGYTRY
Hu4D5-8    EVQLVESGGGLVQPGGSLRLSCAASGFNIKDTYIHWVRQAPGKGLEWVARIYPTNGYTRY
Library-F  EVQLVESGGGLVQPGGSLRLSCAASGFN------HWVRQAPGKGLEWVA-I------T-Y
Library-S  EVQLVESGGGLVQPGGSLRLSCAASGFTFSSYGMHWVRQAPGKGLEWVAVISYDGSNKYY
           ****  ;**  **:**.**:***;****.:.. ;***;*  *  ;****:.  *   . *

CDRH3
              60        70        80 abc     90        100abc     110 SEQ ID NO:
Mu4D5      DPKFQDKATITADTSSNTAYLQVSRLTSEDTAVYYCSRWGGDGFYAMDYWGQGASVTVSS    106
Hu4D5-1    ADSVKGRFTISRDDSKNTLYLQMNSLRAEDTAVYYCARWGGDGFYAMDVWGQGTLVTVSS    107
Hu4D5-8    ADSVKGRFTISADTSKNTAYLQMNSLRAEDTAVYYCSRWGGDGFYAMDYWGQGTLVTVSS    108
Library-F  ADSVKGRFTISADTSKNTAYLQMNSLRAEDTAVYYCAR---------DYWGQGTLVTVSS    109
Library-S  ADSVKGRFTISRDNSKNTLYLQMNSLRAEDTAVYYCAR---------DYWGQGTLVTVSS    110
           ..:.: **: * *.** ***:. * :********:*       * ****: *****
```

| SEQ ID NO: | | | |
|---|---|---|---|
| 111 | L1 | 24 ... 34 | R A S Q G I S N Y L A |
| 112 | L2 | 49 ... 56 | Y A A S S L Q S |
| | L3 | 89 ... 97 | Q Q $Z_4$ P L T |
| | | | $V_K$ — $J_K$ |
| 113 | H1 | 23 ... 35 | A A S G F T F S S Y G M H |
| 114 | H2 | 50 ... 58 | V I S Y D G S N K Y |
| | H3 | 93 ... 102 | A R $Z_{1-10}$ (A/G/D/Y) F D Y $J_H4$ |
| | | | A R $X_{7-15}$ $Y_{3-4}$(G/Y) (F/M) D(Y/V) $J_H6$ |
| | | | $V_H$ — $D_H$ — $J_H$ |

FIGURE 4 CON'T
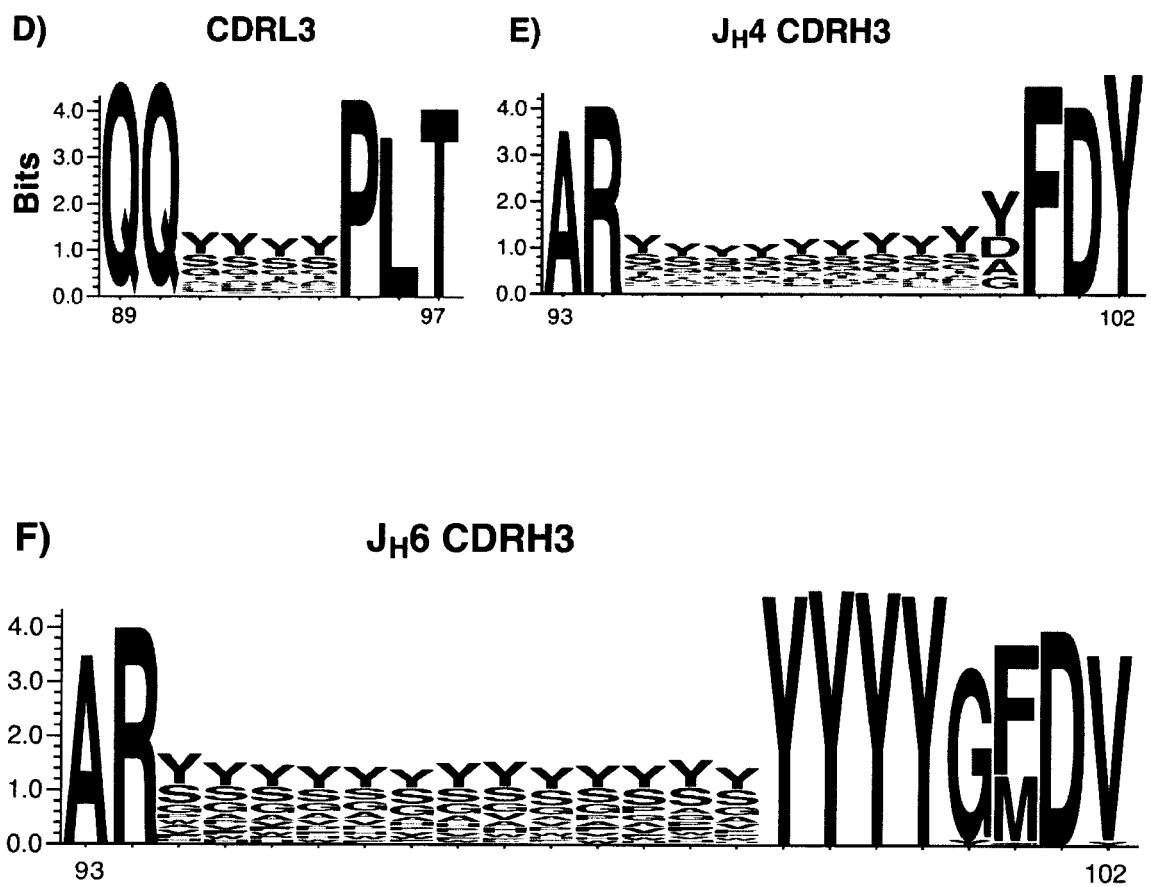

FIGURE 4 CON'T
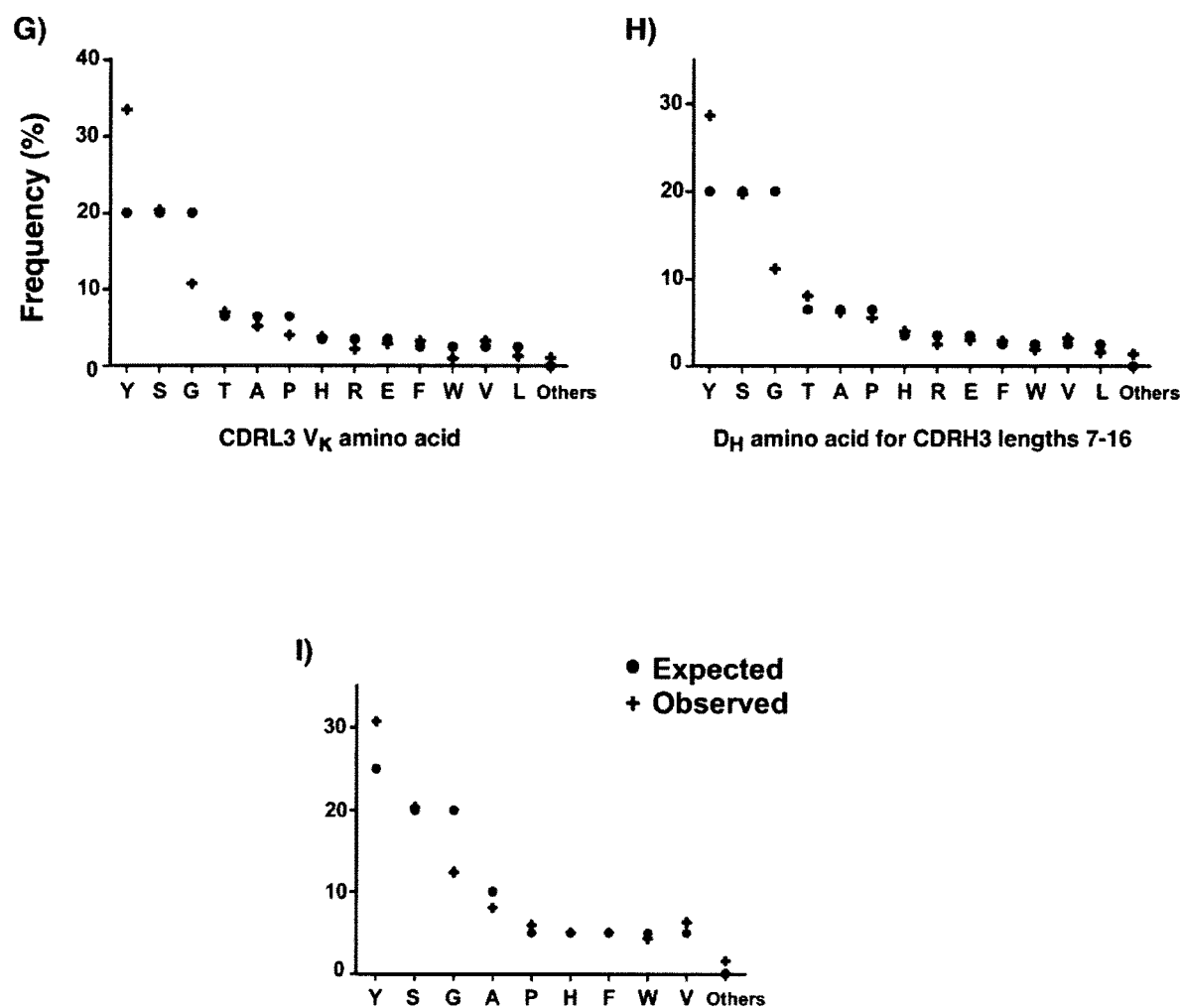

FIGURE 5 CON'T
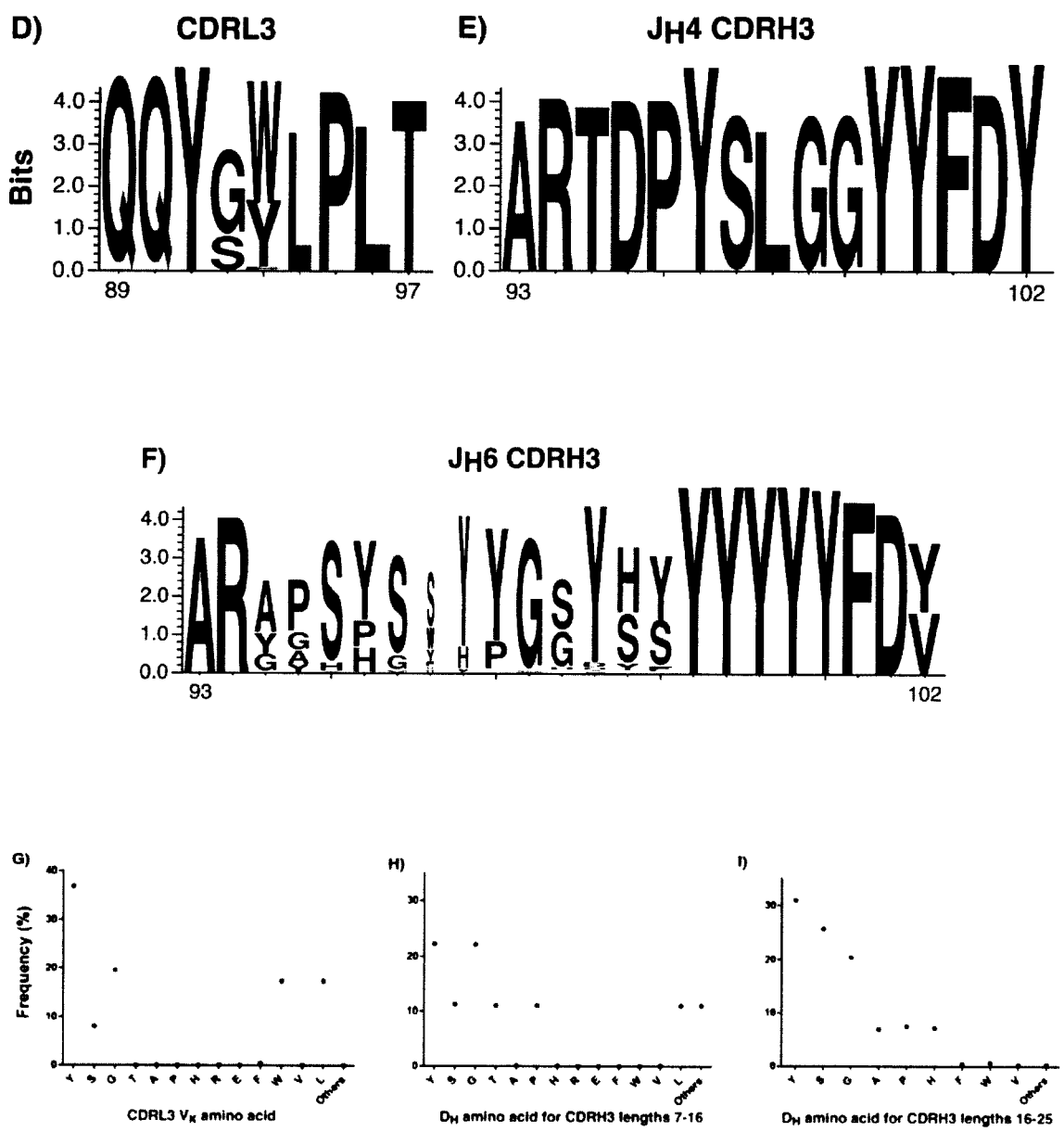

FIGURE 10
A
Anti-HER3 antibody fragments expressed in bacteria
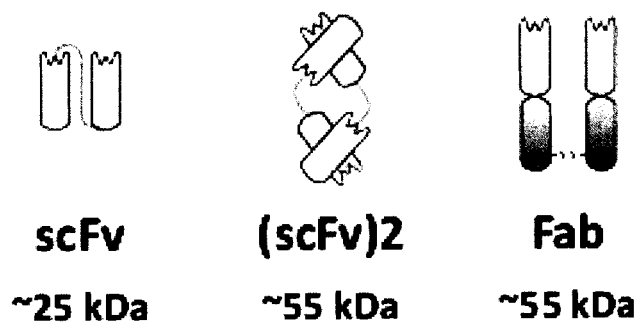
B
Anti-HER3 antibody fragments expressed in mammalian cells
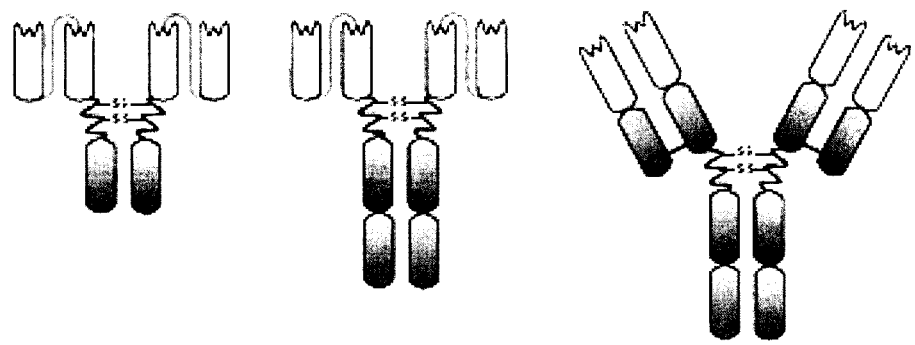

FIGURE 11
A
Anti-HER3 fragments characterization using Bioanalyzer under reducing conditions:
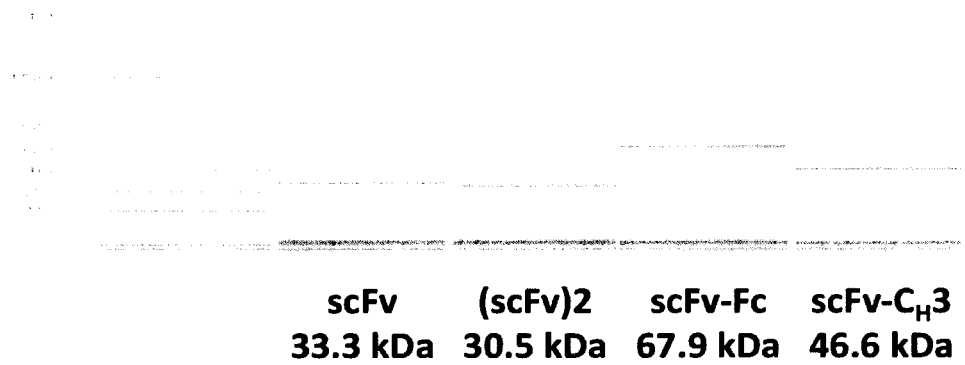
        scFv    (scFv)2   scFv-Fc   scFv-$C_H$3
    33.3 kDa  30.5 kDa  67.9 kDa  46.6 kDa
B
Anti-HER3 scFv-$C_H$3 characterization using Bioanalyzer under reducing vs. non-reducing conditions:
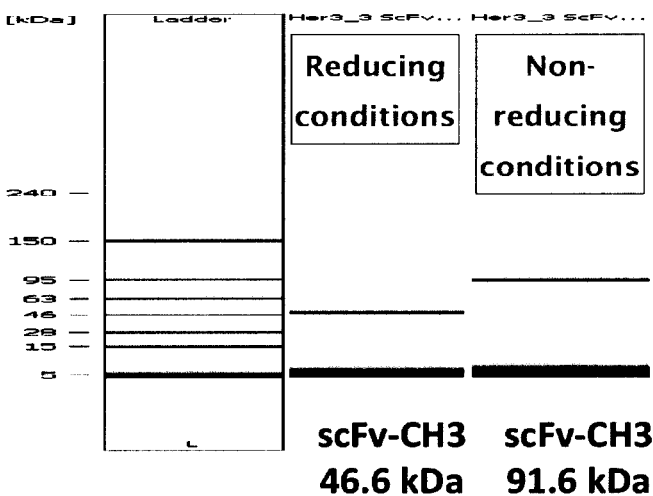
scFv-CH3   scFv-CH3
46.6 kDa   91.6 kDa FIGURE 19
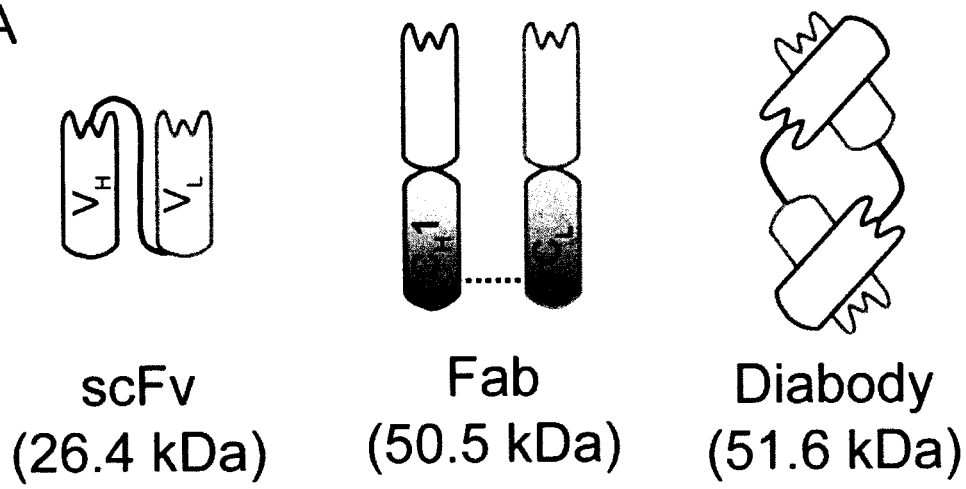
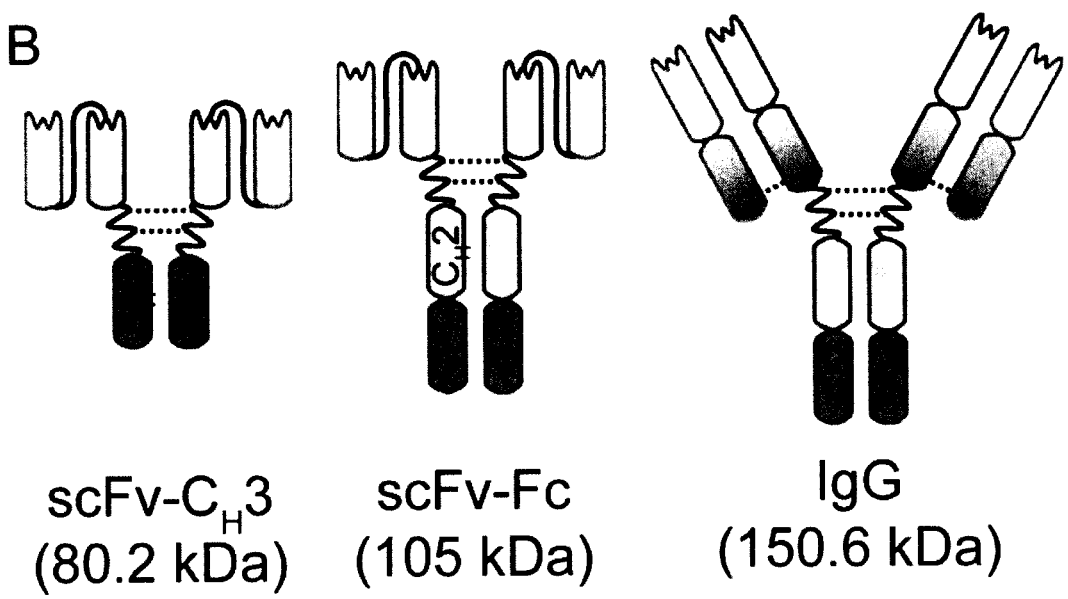

FIGURE 23 CON'T
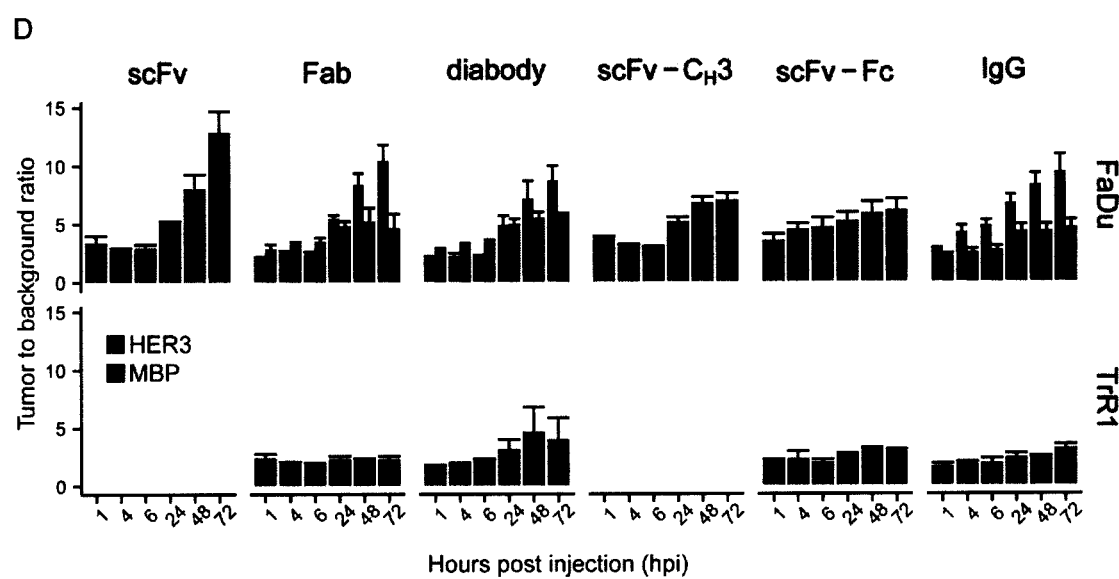

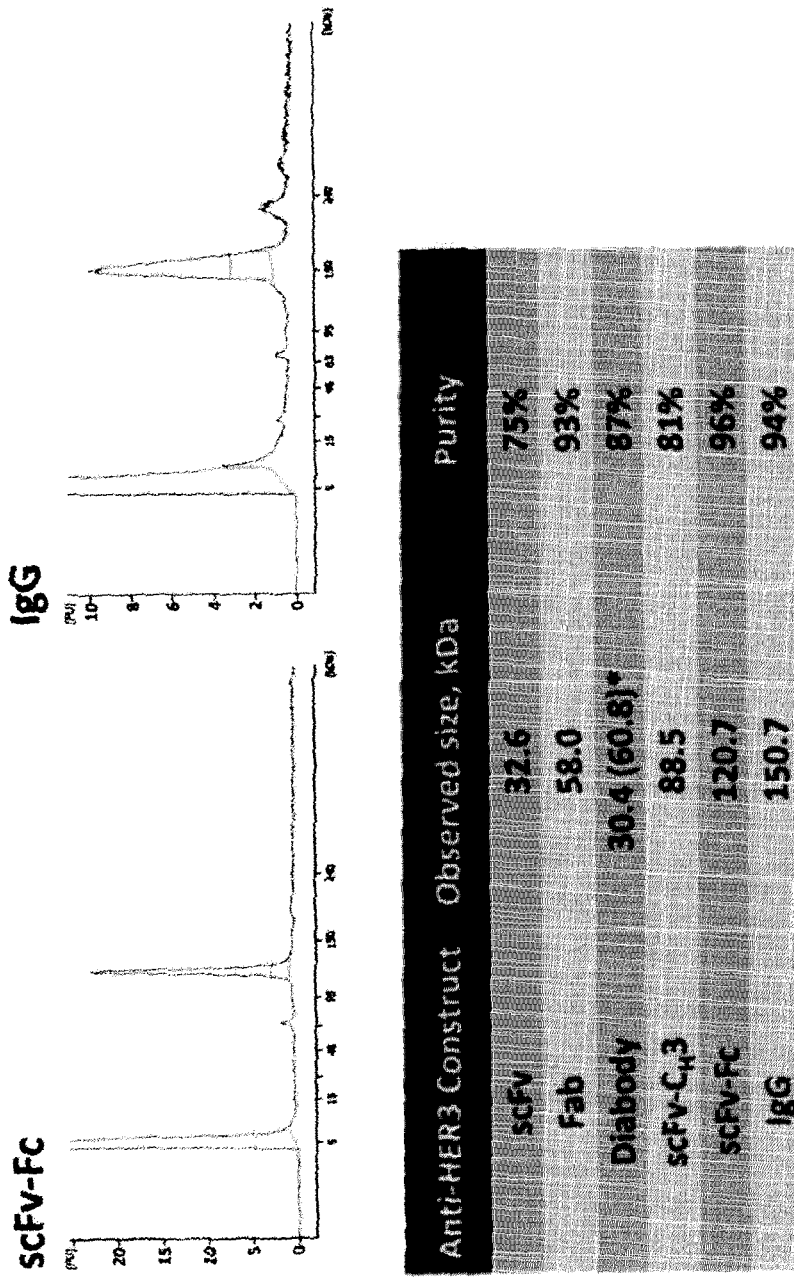
FIGURE 24 CON'T

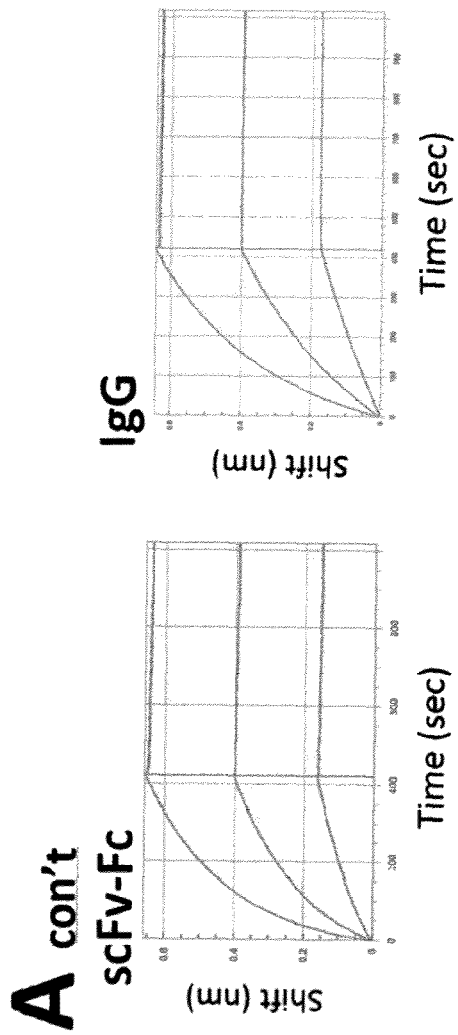
FIGURE 25 CON'T

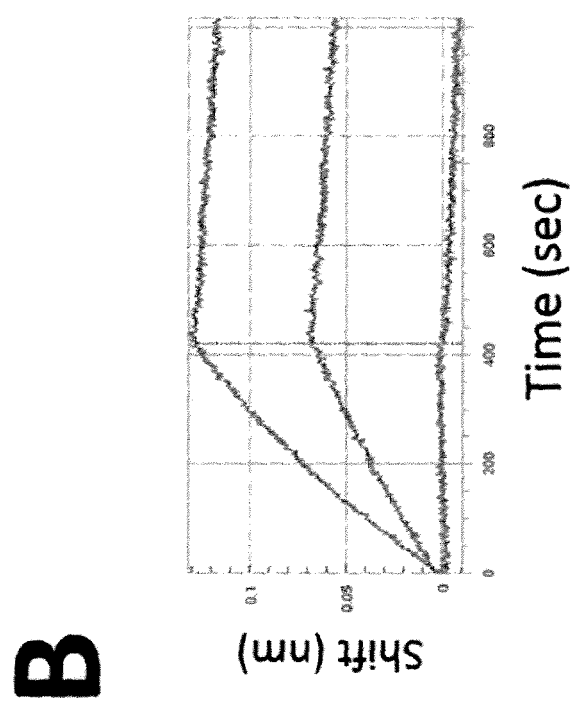
FIGURE 25 CON'T

HER3 BINDING AGENTS AND USES THEREOF

CROSS-REFERENCE TO RELATED APPLICATIONS

This disclosure is a national phase entry of PCT/CA2018/050965 filed Aug. 9, 2018 (which designates the U.S.), which claims the benefit of U.S. provisional application No. 62/543,132 filed Aug. 9, 2017 and U.S. provisional application No. 62/697,288 filed Jul. 12, 2018, the contents of both of which are incorporated herein by reference in their entirety.

INCORPORATION OF SEQUENCE LISTING

A computer readable form of the Sequence Listing "13764-P53452US02_SequenceListing.txt" (69,632 bytes), submitted via EFS-WEB and amended on Jan. 24, 2022, is herein incorporated by reference.

FIELD

This disclosure relates generally to HER3 binding agents, and to methods and uses of these binding agents.

BACKGROUND

The advent of in vitro selection technologies such as phage display, yeast display, and ribosome display have enabled the generation, identification, and engineering of human antibodies without the use of animals (Geyer et al., 2012). Phage display is the most robust and well-established of these methods and has produced antibodies for research and clinical applications (Mahon et al., 2013; Nixon et al., 2014; Frenzel et al., 2016). Phage display is primarily used to isolate either antigen-binding fragments (Fab) or single-chain variable fragments (scFv) from Fab or scFv phage libraries. In contrast to the classical hybridoma technology used for monoclonal antibody production, phage display provides direct access to antibody genes, offers precise control over antibody selection conditions, and allows high-throughput generation and engineering of antibodies (Michnick and Sidhu, 2008; Sidhu, 2012).

Recombinant antibody libraries used in phage display are classified into natural, synthetic, and semisynthetic libraries (Shim, 2016). The fundamental difference between these libraries lies in the source of the diversity. Natural libraries are derived from donor B-lymphocytes (biological diversity), whereas synthetic libraries are assembled from synthetic genes and oligonucleotides (chemical diversity). Semi-synthetic libraries incorporate diversity from a combination of these two approaches (Ponsel et al., 2011). In synthetic libraries, rational design of antibody frameworks enables the incorporation of desirable features for subsequent display and characterization and complementarity determining regions (CDRs) diversities encoded by synthetic oligonucleotides are not limited to the scope of the natural immune system. The use of optimal antibody frameworks and tailored CDR diversity makes synthetic antibody libraries ideal for therapeutic antibody discovery (Harel-Inbar and Benhar, 2012; Adams and Sidhu, 2014).

Synthetic repertoires are classified into libraries built on multiple antibody frameworks or a single antibody framework (Ponsel et al., 2011). Although both library types are used antibody discovery programs, single-framework libraries offer many advantages. First, libraries can be built on a single, clinically-validated, human antibody framework that has optimal biophysical and pharmacokinetic properties. Second, CDR diversities can be designed based on known framework structures, increasing the number of functional members in the antibody library. Third, single framework libraries are well suited for high-throughput antibody generation pipelines, as the defined nature of the framework enables rapid sequence analysis and downstream characterization, and facile reformatting between different vector systems for affinity maturation and antibody expression (Miersch and Sidhu, 2012; Adams and Sidhu, 2014).

Upregulation of human epidermal growth factor receptor HER3 (also known as ErbB3) is commonly seen in various cancers including breast cancer, non-small cell lung cancer, head and neck squamous cell carcinoma and colon cancer. A need remains for antibodies and binding fragments that bind HER3 with high affinity and specificity. In particular, a need remains for anti-HER3 antibodies and binding fragments useful for detecting HER3 expression and for conjugating to effector agents such as cytotoxins.

SUMMARY

The disclosure provides an antibody or binding fragment thereof that specifically binds HER3 comprising:

a light chain variable region and a heavy chain variable region, the light chain variable region comprising complementarity determining region CDR-L3 and the heavy chain variable region comprising complementarity determining region CDR-H3, wherein (i) CDR-L3 comprises the amino acid sequence $YX_1X_2L$ (SEQ ID NO: 123), wherein $X_1$ is G or S and $X_2$ is W or Y and/or comprises an amino acid sequence selected from the amino acid sequences set out in Table 1 (SEQ ID NOs: 9-18); and (ii) CDR-H3 comprises an amino acid sequence selected from SEQ ID NO: 6, SEQ ID NO: 122 or the amino acid sequences set out in Table 2 (SEQ ID NOs: 19-57).

In one embodiment, CDR-L3 comprises the amino acid sequence set out in SEQ ID NO: 3 and/or CDR-H3 comprises the amino acid sequence set out in SEQ ID NO: 6 or SEQ ID NO: 122.

In another embodiment, the light chain variable region further comprises complementarity determining regions CDR-L1 and CDR-L2 and the heavy chain variable region further comprises complementarity determining regions CDR-H1 and CDR-H2, wherein CDR-L1 comprises the amino acid sequence set out in SEQ ID NO: 1 or SEQ ID NO: 117, CDR-L2 comprises the amino acid sequence set out in SEQ ID NO: 2 or SEQ ID NO: 118, CDR-H1 comprises the amino acid sequence set out in SEQ ID NO: 4 or SEQ ID NO: 120 and CDR-H2 comprises the amino acid sequence set out in SEQ ID NO: 5 or SEQ ID NO: 121.

In another embodiment, the HER3 is human HER3.

In another embodiment, the light chain variable region comprises (a) the amino acid sequence of SEQ ID NO: 7 or an amino acid sequence having at least 70% sequence identity to the framework regions of SEQ ID NO: 7 or (b) the amino acid sequence of SEQ ID NO: 8 or an amino acid sequence having at least 70% sequence identity to the framework regions of SEQ ID NO: 8.

In another embodiment, antibody or binding fragment thereof specifically binds HER3 with a dissociation constant ($K_D$) less than or about 2.14 nM.

In another embodiment, the antibody or binding fragment thereof does not inhibit the growth of HER3 expressing cells.

In another embodiment, the binding fragment is selected from the group consisting of a fragment antigen-binding Fab, a single-chain Fv (scFv), a (svFv)2, a scFv-CH3, a scFv-Fc, a diabody, a bispecific antibody, a phage-Fab and a phage-scFv.

In another embodiment, the binding fragment is a Fab.

In another embodiment, the antibody or binding fragment is an IgG molecule.

The disclosure also provides an antibody or binding fragment thereof that competes with the antibody or binding fragment described above for binding HER3.

The disclosure also provides an immunoconjugate comprising (1) the antibody or binding fragment described above attached to (2) an effector agent.

In one embodiment, the effector agent is a detection agent.

In another embodiment, the effector agent is an antineoplastic agent.

In another embodiment, the effector agent is a toxin.

The disclosure also provides a composition comprising the antibody or binding fragment or the immunoconjugate as described above and a carrier.

The disclosure also provides a method of detecting a HER3 expressing cell in a sample, the method comprising:
 a) contacting the sample with
  (i) the antibody or binding fragment described above,
  (ii) an antibody or binding fragment that specifically binds HER3 with a $K_D$ less than or about 2.14 nM and does not inhibit the growth of HER3 expressing cells, or
  (iii) the immunoconjugate described above
 under conditions to form an antibody:HER3 complex; and
 b) detecting the antibody:HER3 complex.

The disclosure also provides a method for screening for, for diagnosing or for detecting a HER3 expressing cancer, the method comprising:
 (a) contacting a sample from a subject using
  (i) the antibody or binding fragment described above,
  (ii) an antibody or antigen-binding fragment that specifically binds HER3 with a $K_D$ less than or about 2.14 nM and does not inhibit the growth of HER3 expressing cells, or
  (iii) the immunoconjugate described above,
 under conditions to form an antibody:HER3 complex; and
 (b) comparing the level of HER3 in the sample with a control,
wherein an increased level of HER3 in the sample compared to the control is indicative that the subject has a HER3 expressing cancer.

In one embodiment, the contacting is in vivo.

The disclosure also provides a method of detecting a HER3 expressing cell in a subject, the method comprising:
 a) administering
  (i) the antibody or binding fragment described above,
  (ii) an antibody or antigen-binding fragment that specifically binds HER3 with a $K_D$ less than or about 2.14 nM and does not inhibit the growth of HER3 expressing cells, or
  (iii) the immunoconjugate described above, and
 b) subjecting said subject to imaging.

In one embodiment, the imaging comprises SPECT or PET imaging.

In another embodiment, the antibody or binding fragment or immunoconjugate is administered by intravenous injection.

In another embodiment, the antibody or binding fragment is conjugated to a fluorescent compound or a radionuclide.

The disclosure also provides a method of delivering a toxin selectively to a HER3-expressing cell, the method comprising contacting the cell with the immunoconjugate described above.

The disclosure also provides a method of treating a HER3 expressing cancer comprising administering an effective amount of an immunoconjugate disclosed herein to a subject in need thereof, optionally wherein the HER3 expressing cancer is a breast cancer, gastric cancer, non-small cell lung cancer, head and neck squamous cell carcinoma or colon cancer.

DRAWINGS

Embodiments are described below in relation to the drawings in which:

FIG. 1 shows multiple sequence alignments. (A) and (B) are multiple sequence alignments of relevant 4D5 framework sequences including the variable light chain region and the variable heavy chain region respectively. The following sequences were included in the alignment: anti-HER2 murine 4D5 Fab (Mu4D5), Hu4D5-1 (fully humanized form of Mu4D5), Hu4D5-8 (humanized form of Mu4D5 and Herceptin Fab), Library-F (4D5 framework used in library-F) and Library-S (4D5 framework used in library-S). Hyphen indicates diversified positions in Library-F and Library-S. Asterisk, colon, and period indicate identical residues, conservative substitutions, and semi-conservative substitutions, respectively. Sequences were aligned using the Clustal Omega program. The Kabat scheme was used for numbering amino acids.

FIG. 2 shows sequence logos used for designing fixed CDRs in Library-S. Sequence conservation within (A) CDRL1, (B) CDRL2, (C) CDRH1, and (D) CDRH2 regions of Vκ1 (n=100) and VH3 (n=500) antibody sequences. Sequence logos were generated using the WebLogo server. The Kabat scheme was used for numbering amino acids.

FIG. 3 shows the four fixed CDRs (L1, L2, H1, and H2) and two diversified CDRs (L3 and H3) of Library-S. Z denotes a mixture of thirteen amino acids: Y (20%), S (20%), G (20%), T (6.5%), A (6.5%), P (6.5%), H (3.5%), R (3.5%), E (3.5%), F (2.5%), W (2.5%), V (2.5%) or L (2.5%). X denotes a mixture of nine amino acids: Y (25%), S (20%), G (20%), A (10%), F (5%), W (5%), H (5%), P (5%) or V (5%). CDRH3 length was varied by altering the number of X and Z amino acids. The Vκ and Jκ regions within CDRL3 are indicated. The $V_H$, $D_H$, and $J_H$ regions within CDRH3 are indicated. The Kabat scheme was used for numbering amino acids.

FIG. 4 shows various sequencing analyses. (A) is a sequencing analysis of the naïve Library-S diversity depicting overall frequency of correct and incorrect CDRH3 sequences in sub-libraries (SL) 1-20. The Kabat scheme was used for numbering amino acids. (B) and (C) are sequencing analyses of the naïve Library-S diversity depicting CDRL3 length distribution and CDRH3 length distribution respectively. The Kabat scheme was used for numbering amino acids. (D), (E) and (F) are sequencing analyses of the naïve Library-S diversity depicting the sequence logos showing the positional amino acid composition of CDRL3 sequences, containing 9 residues, $J_H4$ CDRH3 sequences, containing 15 residues, and $J_H6$ CDRH3 sequences, containing 23 residues respectively. The Kabat scheme was used for numbering amino acids. (G), (H), and (I) are sequencing analyses of the naïve Library-S diversity depicting the programmed and observed amino acid composition of the CDRL3 random region, the CDRH3 random $D_H$ segment for lengths 7-16, and the CDRH3 random $D_H$ segment for lengths 16-25 respectively. The Kabat scheme was used for numbering amino acids.

FIG. 5 shows an NGS analysis of the Library-S selection against HER3. (A) Cumulative distribution plots for CDRL3 and CDRH3 sequence counts from the round 4 selection against HER3-ECD. (B) CDRL3 length distribution. (C) CDRH3 length distribution. Sequence logos showing the positional amino acid composition of (D) CDRL3 sequences, (E) JH4 CDRH3 sequences, and (F) and JH6 CDRH3 sequences. Total amino acid composition of the (G) CDRL3 random region, (H) the CDRH3 random DH segment for lengths 7-16, and (I) the CDRH3 random DH segment for lengths 16-25. The Kabat scheme was used for numbering amino acids.

FIG. 6 shows characterization of anti-HER3 Fabs. (A) Diversified CDR sequences of two anti-HER3 Fabs isolated from Library-S. The frequency and rank of Fabs in the round-4 phage selection pool are also given. (B) Kinetic analysis of HER3-ECD binding to sensor immobilized Fab HER3-3. (C) Kinetic analysis of HER3-ECD binding to sensor immobilized Fab HER3-10. KD values were obtained by fitting the association and dissociation data points to 1:1 binding model. (D) Binding specificity of Fabs HER3-3 and HER3-10 to HER3 and EGFR. In panels B-D, affinity and specificity analyses of Fabs were conducted using bio-layer interferometry. (E) Flow cytometry analysis of Fab HER3-3 binding to cell-surface HER3. Flow histograms showing the binding of Fab HER3-3 (100 pmoles) to HER3-overexpressing HEK293T cells (dark gray) relative to unstained (dashed) and untransfected (light grey) HEK293T cells. Binding was assessed using IRDYE 8000W conjugated to Fab HER3-3.

FIG. 7 shows characterization of HER3-3 IgG. (A) Kinetic analysis of HER3-ECD binding to sensor-immobilized HER3-3 IgG using bio-layer interferometry. (B) Immunofluorescent staining of HER3 using HER3-3 IgG. Left panel: untransfected HEK293T cells stained with HER3-3 IgG. Right panel: HER3-overexpressing HEK293T cells stained with HER3-3 IgG. (C) Flow cytometry analysis of HER3-3 IgG binding to HER cell lines. Binding was assayed using a phycoerythrin (PE)-conjugated anti-human IgG secondary antibody. Cell lines are ordered from lowest to highest change in mean fluorescence intensity (ΔMFI) of HER3. ΔMFI is calculated as the difference in fluorescence between cells treated with HER3-3 IgG and an isotype control antibody. Values were as follows: TrR1=0, HCC202=200, BT474=1000, AU565=1400, SKBR3=2200, HCC1419=2300.

FIG. 8 shows imaging of the FaDu murine xenograft model with Fab HER3-3. (A) Flow cytometry histograms showing the binding of HER3-3 Fab to FaDu cells (light gray: unstained FaDu cells and dark gray: FaDu cells stained with 50 pmoles of HER3-3 Fab labeled with IRDye-8000W). (B) Representative near-infrared posterior whole-body images merged with white light images of CD-1 nude mice bearing FaDu xenografts (right dorsum) at 6 and 24 h post-intravenous injection with 0.5 nmole of HER3-3 Fab-IRDye 800CW (top), or anti-MBP Fab-IRDye 800CW (bottom). Xenografts and kidneys are indicated with white arrows and arrow heads, respectively.

FIG. 9 shows a binding analysis of purified Fabs HER3-3 and HER3-10 to the HER3-ECD-Fc construct using Fab-ELISA. Bovine Serum Albumin (BSA) and the Fc protein were used as controls. The target and control proteins were immobilized on Maxisorp plates, and the binding of Fabs to immobilized proteins were assessed using a horseradish peroxidase (HRP)-conjugated anti-HIS antibody.

FIG. 10 shows anti-HER3 antibody fragments. (A) and (B) show anti-HER3 antibody fragments expressed in bacteria and in mammalian cells respectively.

FIG. 11 shows anti-HER3 fragments. (A) shows the characterization of anti-HER3 fragments using Bioanalyzer under reducing conditions. (B) shows the characterization of anti-HER3 scFV-$C_H3$ using Bioanalyzer under reducing vs. non-reducing conditions.

Figure 18:
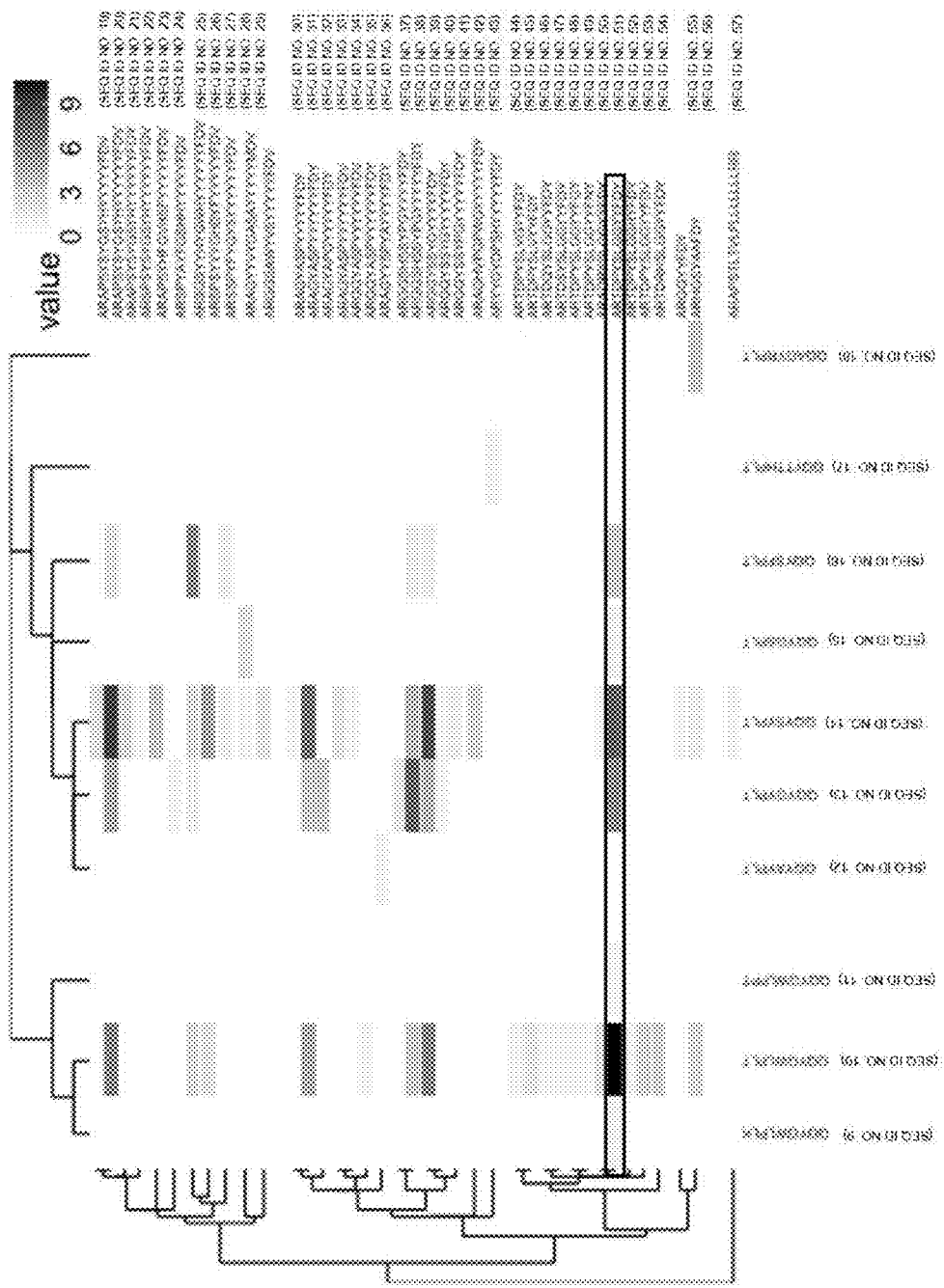

FIG. 18 shows a selection performed for antibodies that bind HER3. The heavy chain CDR-H3 sequence is shown in the y-axis and the corresponding light chain CDR-L3 sequence is shown in the x-axis. The fill intensity represents the number of times the sequence was observed in base 2 ($2^n$). The CDR-L3 and CDR-H3 sequences are set out in Tables 1 and 2.

FIG. 19 shows a schematic representation of anti-HER3 IgG and antibody fragments with their calculated molecular weights. (A) Anti-HER3 antibody fragments expressed in bacteria (scFv, Fab, and diabody). (B) Anti-HER3 IgG and fragments expressed in mammalian cells (scFv-$C_H3$, scFv-Fc, and IgG). $C_H1$, constant heavy domain 1; $C_H2$, constant heavy domain 2; $C_H3$, constant heavy domain 3; $C_L$, constant light domain; $V_H$, variable heavy domain; $V_L$, variable light domain, dotted line indicates disulphide bond.

Figure 20:
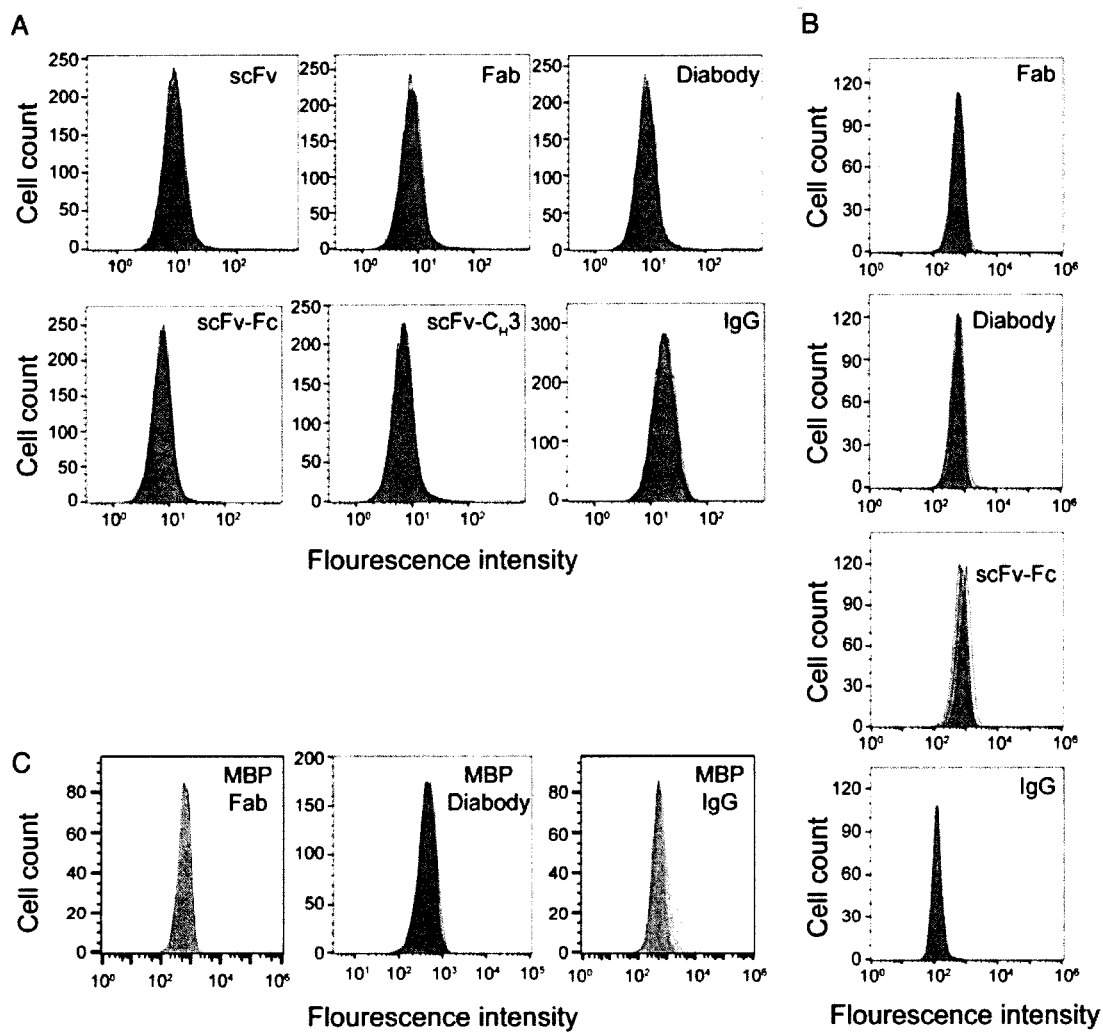

FIG. 20 shows binding of anti-HER3 and anti-MBP probes to cell-lines. (A) Flow cytometry histograms showing the binding of anti-HER3 scFv, Fab, diabody, scFv-$C_H3$, scFv-Fc, and IgG to FaDu cells. Light gray: unstained FaDu cells. Dark gray: FaDu cells stained with 0.5 μM (in triplicate) of IgG or antibody fragments labeled with IRDye800CW. (B) Flow cytometry histograms showing the binding of anti-HER3 Fab, diabody, scFv-Fc, and IgG to TrR1 cell line. Dark gray histogram: unstained TrR1 cells. Light gray: TrR1 cells stained with 0.1, 0.3, and 1 μM of anti-HER3 IgG or antibody fragments labeled with IRDye8000W. (C) Flow cytometry histograms showing the binding of anti-MBP control Fab, diabody, and IgG to FaDu cells. Dark gray: unstained FaDu cells. Light gray: FaDu cells stained with 0.1, 0.3, and 1 μM of IgG or antibody fragments labeled with IRDye8000W.

Figure 21:
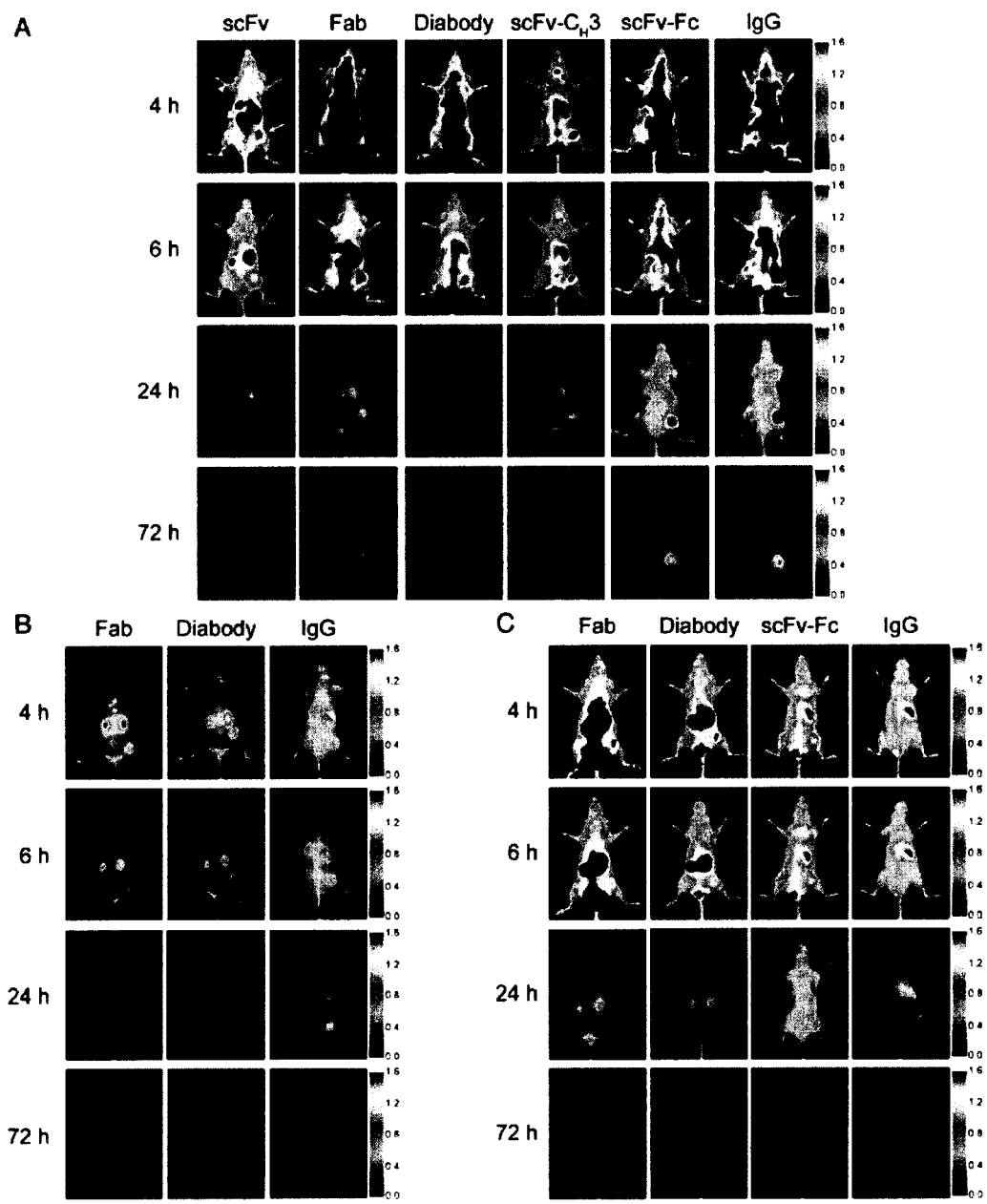

FIG. 21 shows near-infrared imaging of the anti-HER-IRDye8000W probes to murine xenograft models. Representative near-infrared posterior whole-body images merged with white light images of CD-1 nude mice bearing subcutaneous xenografts (right hind flank) at 4, 6, 24, and 72 h post-intravenous injection with 0.5 nmol of imaging probe. (A) HER3$^+$ (FaDu) xenografts imaged with anti-HER3 scFv, Fab, diabody, scFv-$C_H3$, scFv-Fc, and IgG labeled with IRDye8000W, or (B) HER3$^+$ (FaDu) xenografts imaged with control anti-MBP Fab, diabody, and IgG. (C) HER3- (TrR1) xenografts imaged with anti-HER3 Fab, diabody, scFv-Fc, and IgG labeled with IRDye8000W. The fluorescence scale is shown on the right of the images. Xenografts are indicated with white arrows and kidneys (K) and background forelimb muscle (B) are indicated with arrow heads. Contralateral site (C) is indicated with dotted circles.

Figure 22:
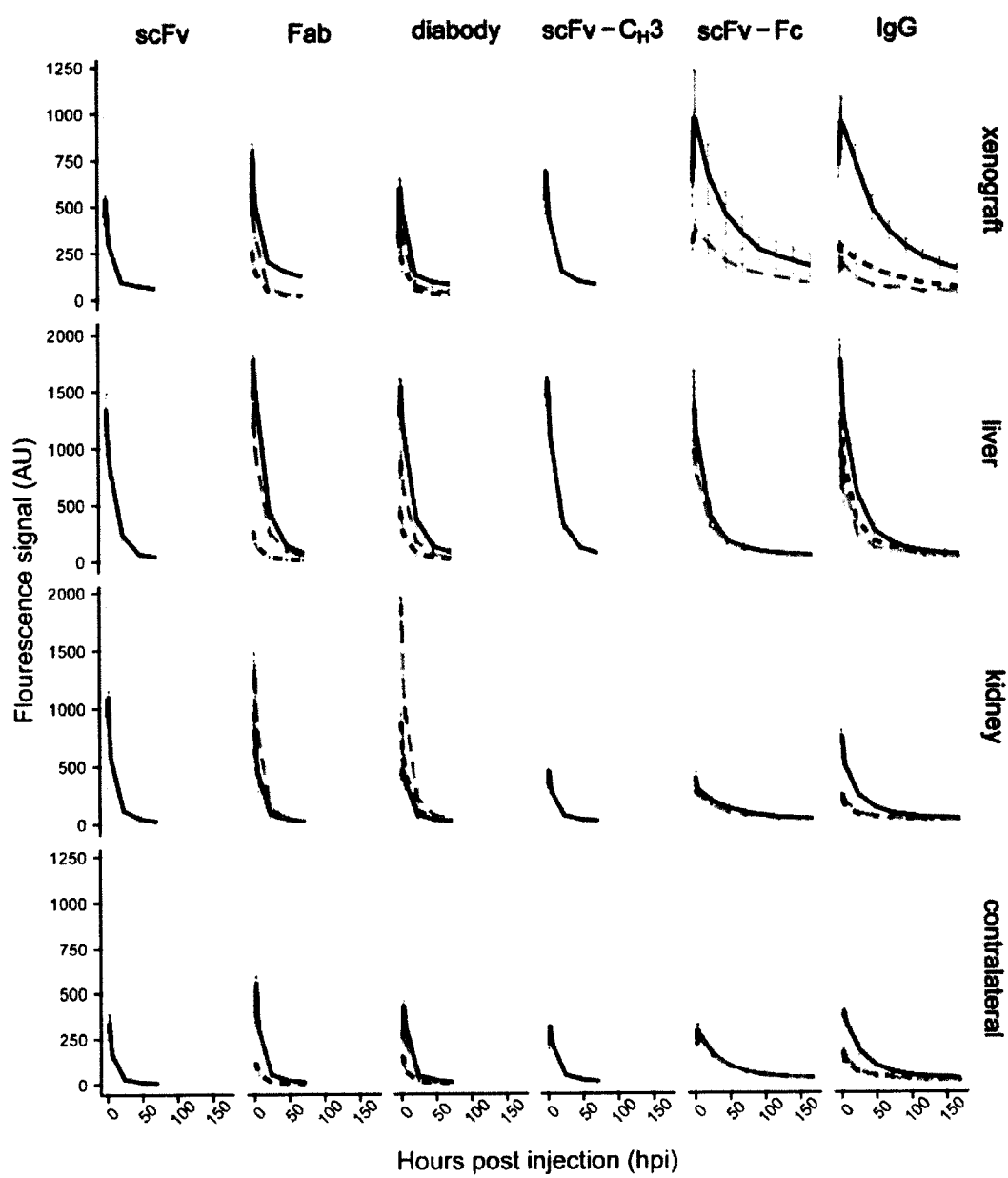

FIG. 22 shows a biodistribution analysis of IRDye8000W-labeled IgG and antibody fragments in mice bearing FaDu xenografts. Mean fluorescence signal (arbitrary units) for control anti-MBP Fab, diabody, and IgG in HER3+ (FaDu) xenograft (dotted blue lines), anti-HER3 scFv, Fab, diabody, scFv-$C_H$3, scFv-Fc, and IgG in HER3+ (FaDu) xenograft (solid red lines), and HER3− (TrR1) xenograft (dashed green lines) in liver, kidney, and contralateral site. Data are the average from three mice and error bars represent standard error of the mean.

Figure 23:
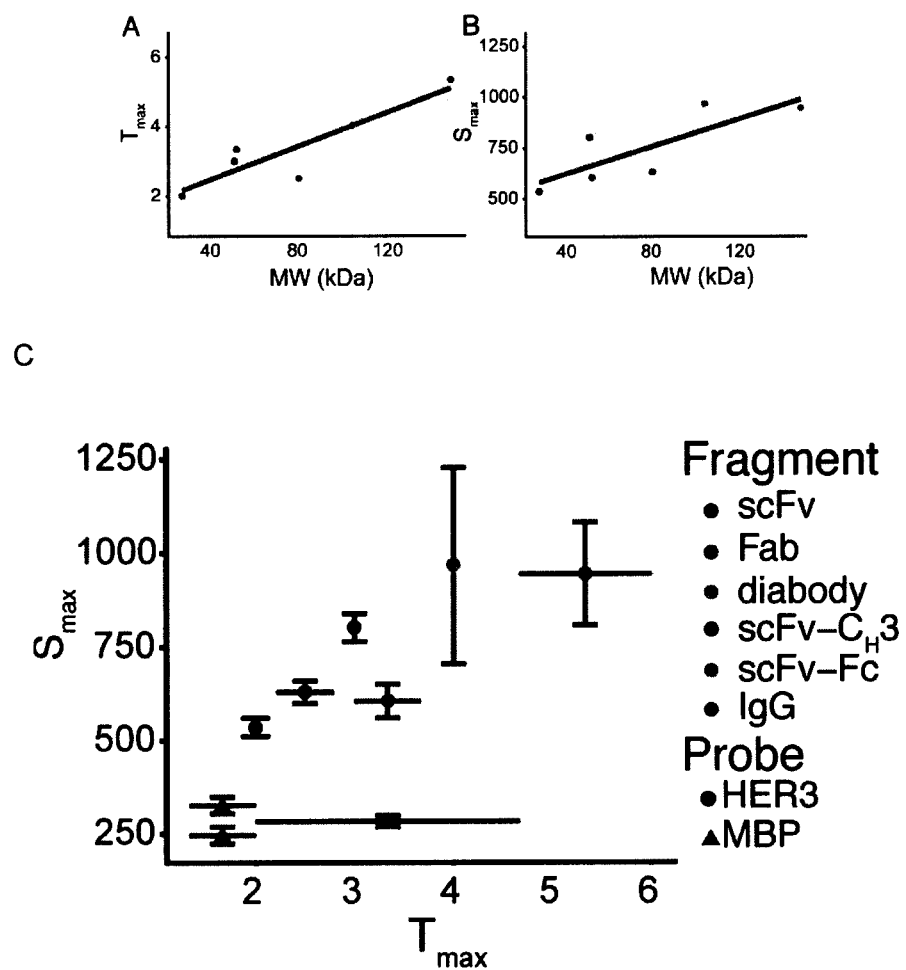

FIG. 23 shows a summary of IRDye8000W-labeled IgG and antibody fragments imaging parameters. (A) Anti-HER3 IgG and antibody fragments time to reach maximum fluorescence signal in FaDu xenograft (Tmax, Y-axis), against molecular weight of the IgG and antibody fragments (MW, kDa, X-axis). (B) Anti-HER3 IgG and antibody fragments value of maximum fluorescence signal in FaDu xenograft (Smax, Y-axis), against molecular weight of the IgG and antibody fragments (MW, kDa, X-axis). Straight line is linear fitting of data points and gray zone represents 95% confidence interval of fitting. (C) The maximum fluorescence signal (Smax) in FaDu xenografts at the maximum time (Tmax) post injection of anti-HER3 IgG and antibody fragments and control anti-MBP antibody fragments labeled with IRDye8000W. (D) Tumor to background ratio of xenograft signal compared to mouse forelimb muscle signal at 1, 4, 6, 24, 48 and 72 h post-intravenous injection of 0.5 nmol of anti-HER3 or anti-MBP probe in HER3+ (FaDu) or HER3− (TrR1) xenografts. Error bars represent standard error of the mean.

Figure 24:
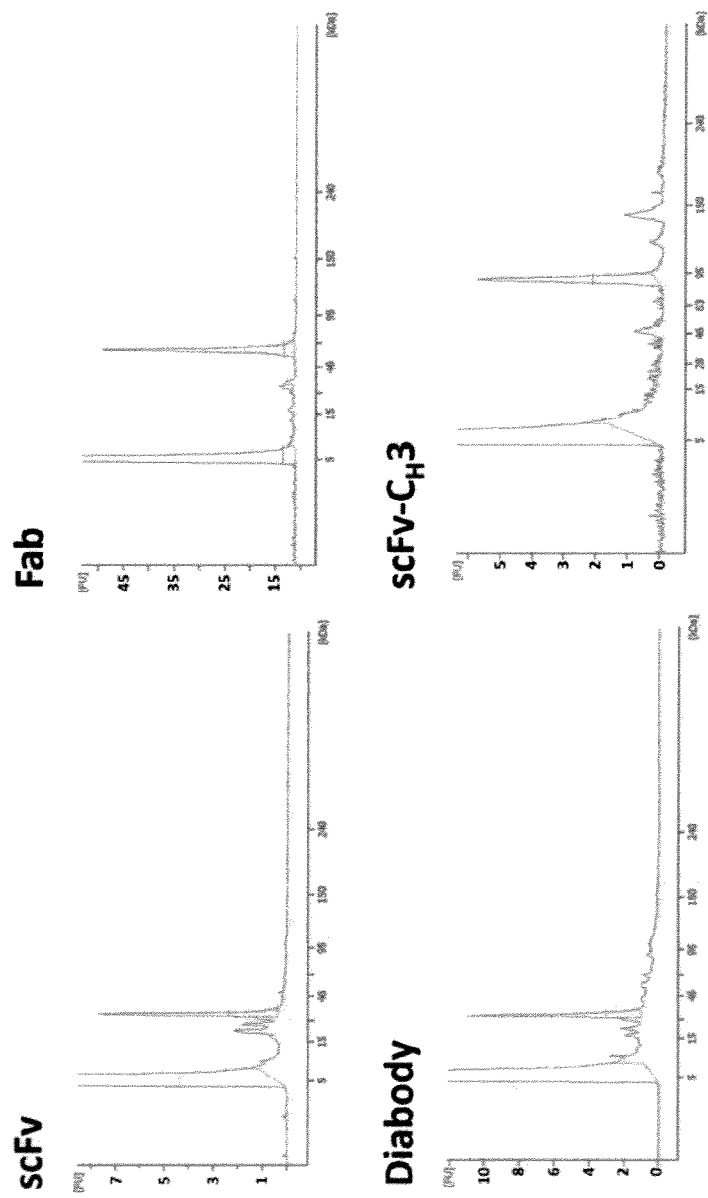

FIG. 24 shows a characterization of anti-HER3 antibody fragments using the Agilent Bioanalyzer 2100. Representative Bioanalyzer electropherograms of anti-HER3 scFv, diabody, Fab, scFv-$C_H$3, scFv-Fc, and IgG under non-reducing conditions. Molecular weight and purity of the IgG and antibody fragments (%) were calculated based on protein standards from an Agilent High Sensitivity Protein 250 kit and are summarized in the table.

Figure 25:
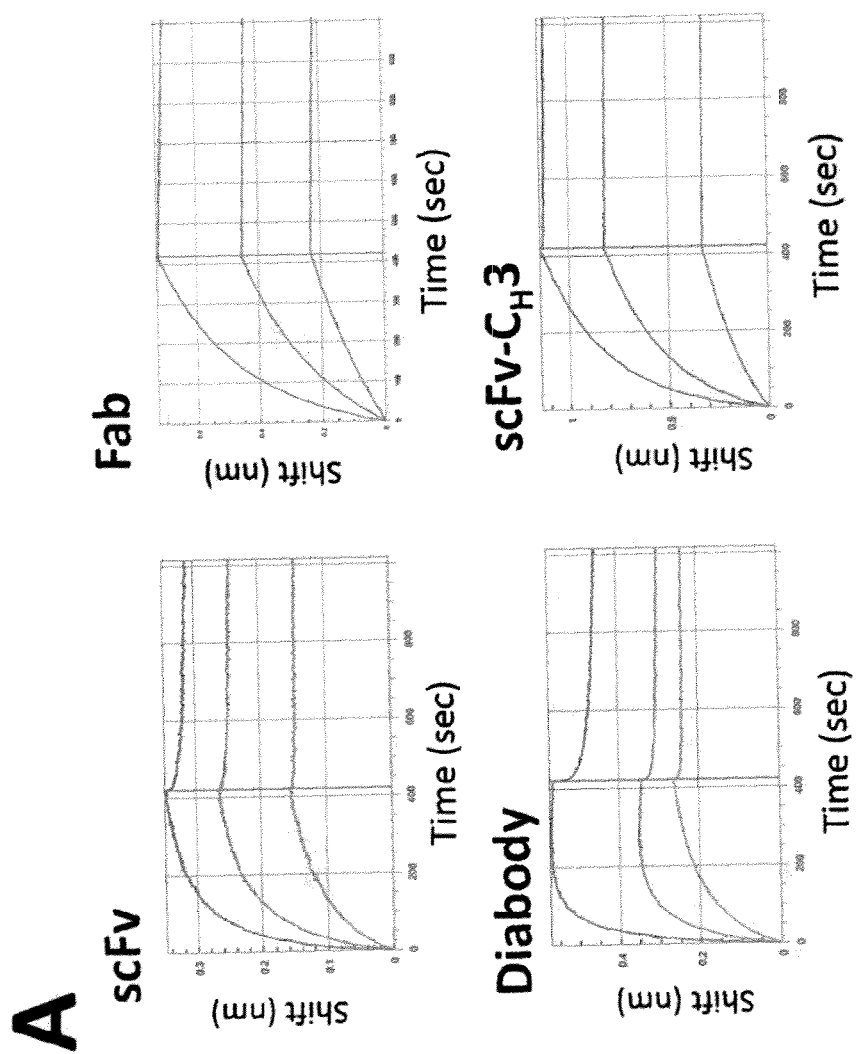

FIG. 25 shows biolayer interferometry analysis of binding kinetics of anti-HER3 antibody fragments. (A) Binding kinetics anti-HER3 scFv, diabody, Fab, scFv-$C_H$3, scFv-Fc, and IgG against recombinant human HER3 extracellular domain. Lines represent the three concentrations of target tested; 52.6, 131.6, and 263.2 nM (B) Binding kinetics anti-HER3 IgG against recombinant mouse HER3 extracellular domain. Lines represent the three concentrations of target tested; 10.5, 131.6, and 263.2 nM.

Figure 26:
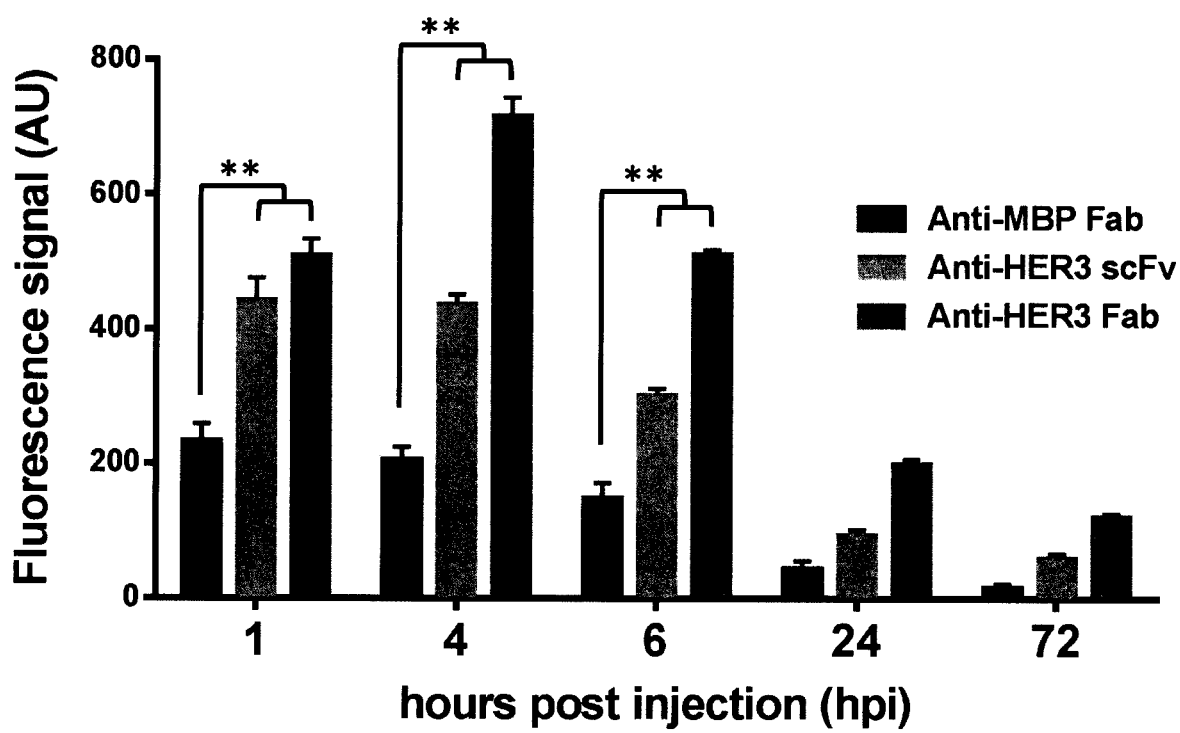

FIG. 26 shows a biodistribution analysis of IRDye800CW-labeled monovalent antibody fragments in mice bearing FaDu xenografts. Mean fluorescent signal (arbitrary units) for control anti-MBP Fab (black) anti-HER3 scFv (light gray), and Fab (dark gray) in FaDu xenografts at 1, 4, 6, 24 and 72 hours post injection (hpi). **=p value <0.01, AU represents arbitrary units. Error bars represent standard error of the mean.

Figure 27:
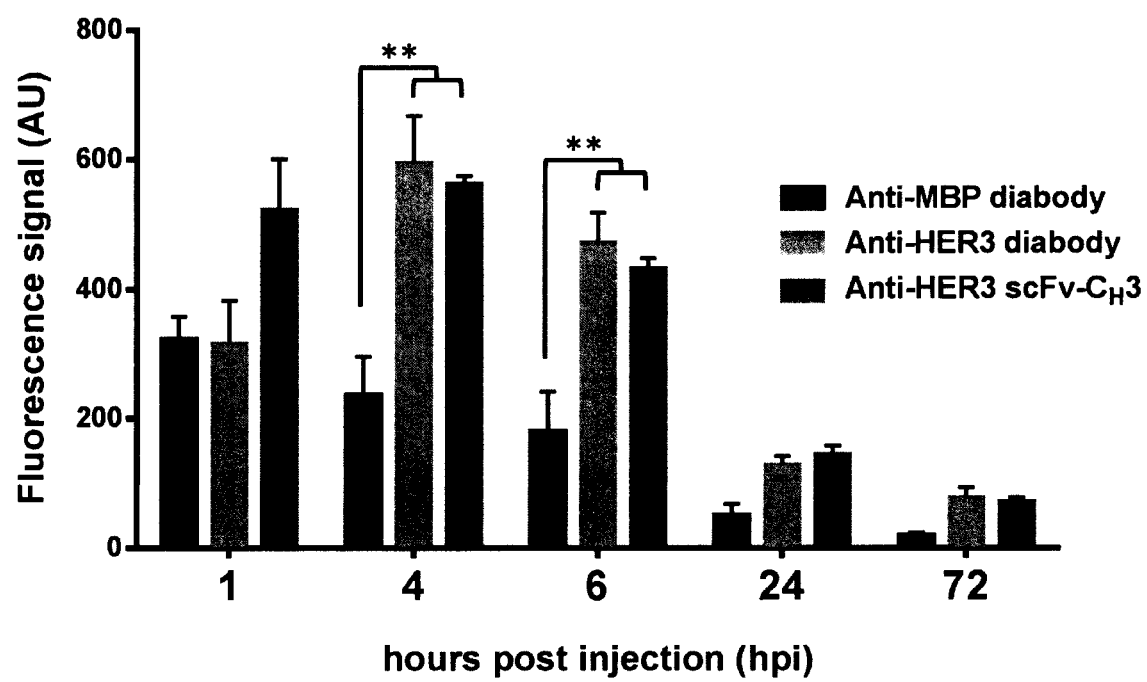

FIG. 27 shows a biodistribution analysis of IRDye800CW-labeled bivalent antibody fragments lacking Fc domain in mice bearing FaDu xenografts. Mean fluorescent signal (arbitrary units) for control anti-MBP diabody (black) anti-HER3 diabody (light gray), and scFv-$C_H$3 (dark gray) in FaDu xenografts at 1, 4, 6, 24 and 72 hours post injection (hpi). **=p value<0.01, AU represents arbitrary units. Error bars represent standard error of the mean.

Figure 28:
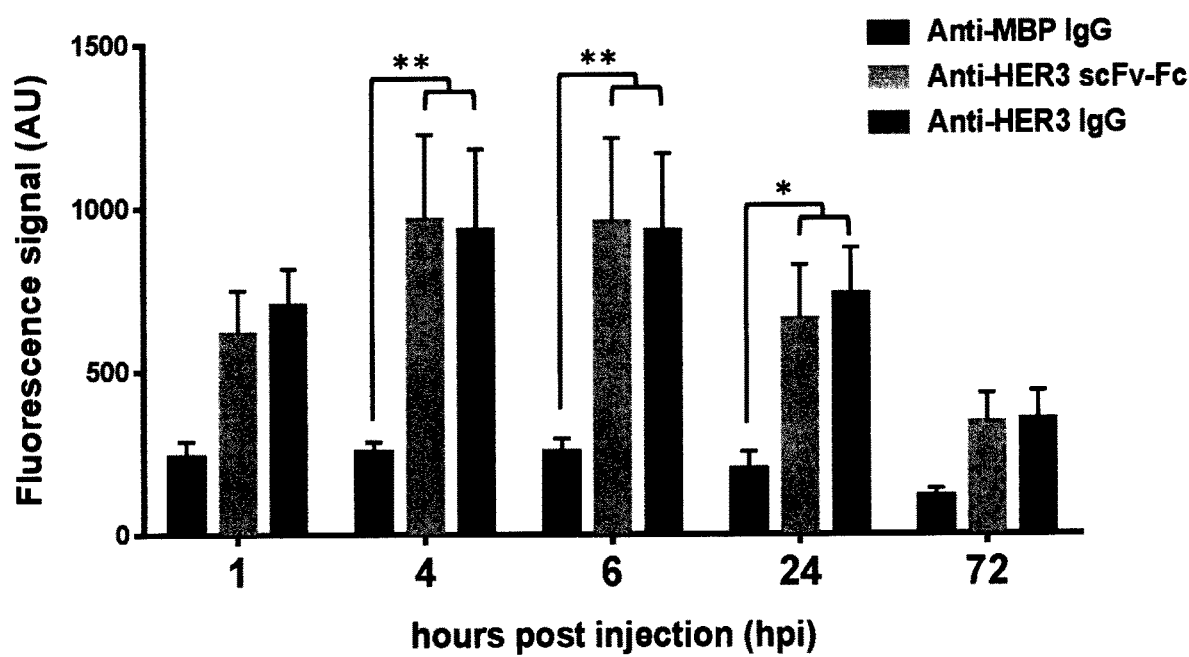

FIG. 28 shows a biodistribution analysis of IRDye800CW-labeled bivalent antibody and fragments containing Fc domain in mice bearing FaDu xenografts. Mean fluorescent signal (arbitrary units) for control anti-MBP IgG (black) anti-HER3 scFv-Fc (light gray), and IgG (dark gray) in FaDu xenografts at 1, 4, 6, 24 and 72 hours post injection (hpi). *=p value<0.05, **=p value <0.01, AU represents arbitrary units. Error bars represent standard error of the mean.

Figure 29:
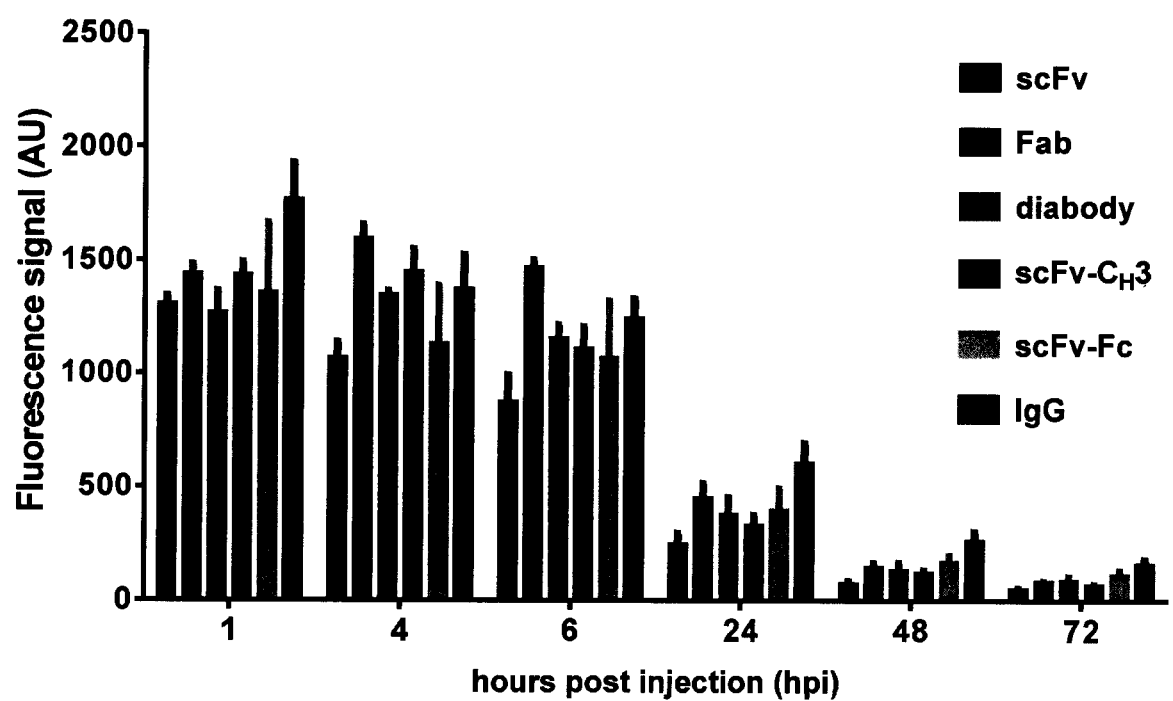

FIG. 29 shows liver fluorescence of IRDye800CW-labeled anti-HER3 IgG and antibody fragments in mice bearing FaDu xenografts. Mean fluorescent signal (arbitrary units) for (from left to right) anti-HER3scFv, Fab, diabody, scFv-$C_H$3, scFv-Fc and IgG in liver at 1, 4, 6, 24, 48 and 72 hours post injection (hpi). AU represents arbitrary units. Error bars represent standard error of the mean.

Figure 30:
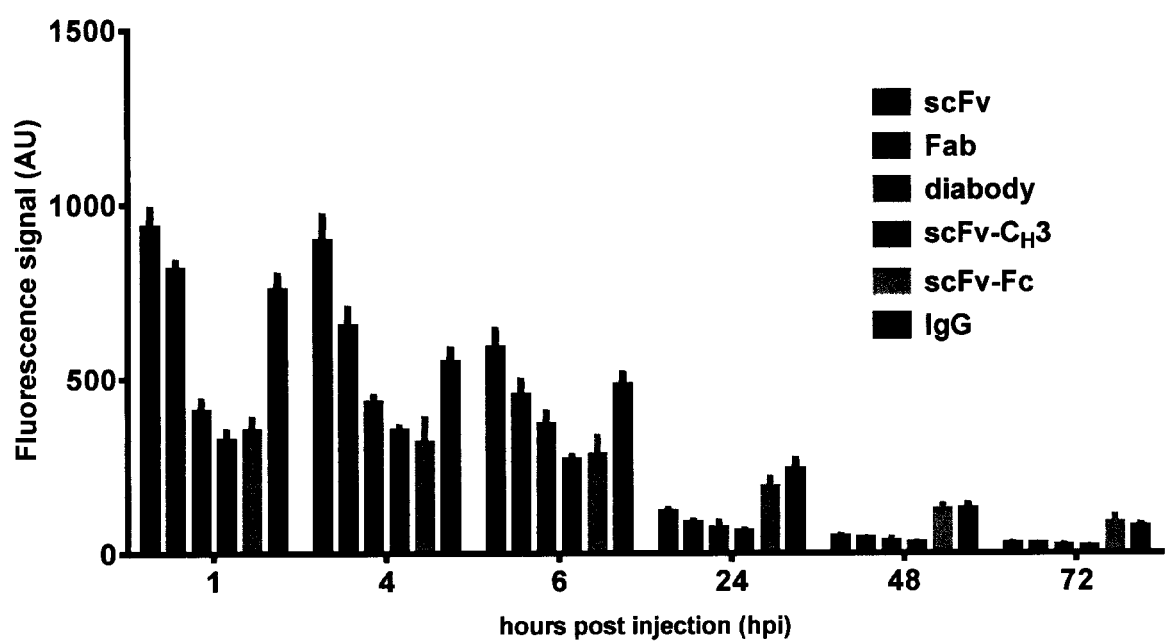

FIG. 30 shows kidney fluorescence of IRDye800CW-labeled anti-HER3 IgG and antibody fragments in mice bearing FaDu xenografts. Mean fluorescent signal (arbitrary units) for (left to right) anti-HER3scFv, Fab, diabody, scFv-$C_H$3, scFv-Fc and IgG in kidney at 1, 4, 6, 24, 48 and 72 hours post injection (hpi). AU represents arbitrary units. Error bars represent standard error of the mean.

Figure 31:
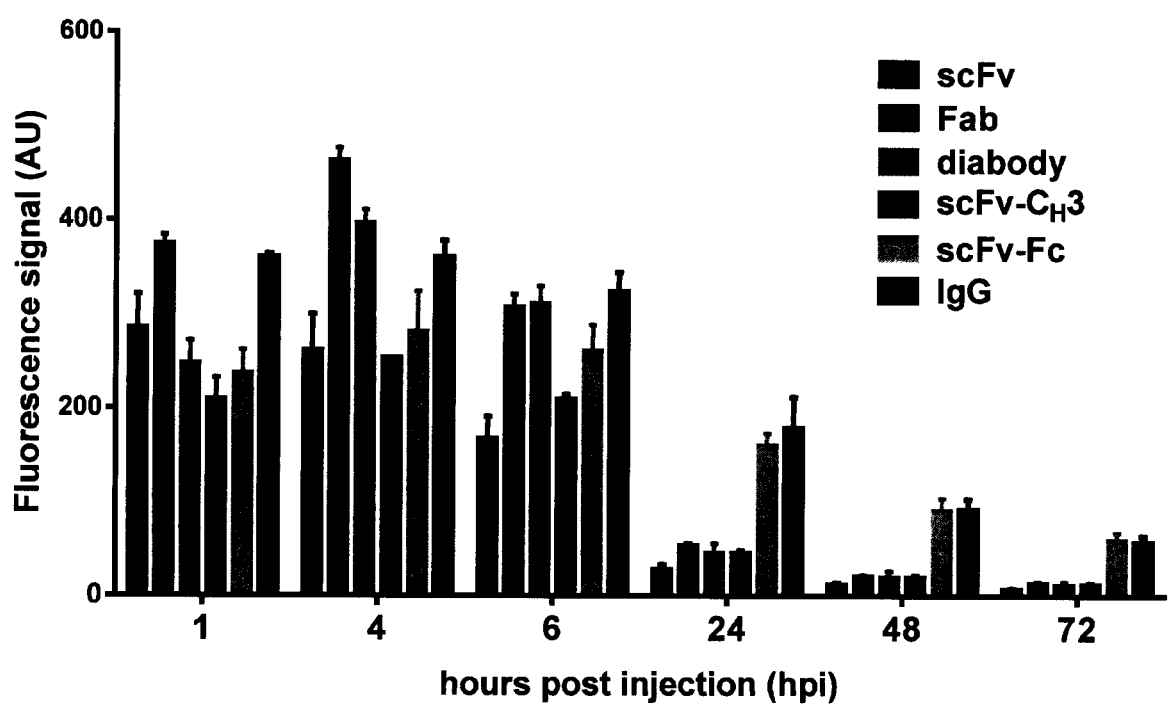

FIG. 31 shows contralateral site fluorescence of IRDye8000W-labeled anti-HER3 IgG and antibody fragments in mice bearing FaDu xenografts. Mean fluorescent signal (arbitrary units) for (left to rights) anti-HER3scFv, Fab, diabody, scFv-$C_H$3, scFv-Fc and IgG in contralateral site at 1, 4, 6, 24, 48 and 72 hours post injection (hpi). **=p value <0.01, ns=p value >0.05, AU represents arbitrary units. Error bars represent standard error of the mean.

DESCRIPTION OF VARIOUS EMBODIMENTS

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Further, the definitions and embodiments described in particular sections are intended to be applicable to other embodiments herein described for which they are suitable as would be understood by a person skilled in the art. For example, in the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Antibody and/or Binding Fragment Thereof

The inventors constructed a phage-displayed, synthetic Fab library built on a modified trastuzumab framework. The library diversity was engineered within CDR-L3 and CDR-H3. A solid phase selection was conducted against the HER3 ectodomain (HER3-ECD). CDRs were identified as shown in Example 1 and FIG. 18.

A frequent Fab sequence in the anti-HER3 ECD pool was designated Fab HER3-3. The CDR regions of Fab HER3-3 are set out in Example 1. Fab HER3-3 bound tightly to recombinant HER3-ECD ($K_D$=2.14 nM) and cell-surface HER3. However, Fab HER3-3 did not inhibit the growth of HER3 positive cell-lines (Example 1). Imaging data showed specific tumor uptake in HER3 positive cell line xenografts. The anti-HER3 antibodies and binding fragments disclosed herein can be used as detection agents and in methods for detecting HER3 levels. They can also be conjugated to effector agents such as labels, tags and cytotoxins.

Accordingly, the present disclosure provides antibodies and binding fragments thereof which specifically bind HER3.

The term "HER3" as used herein refers to the human epidermal growth factor receptor-3 (also referred to as receptor tyrosine-protein kinase; erbB-3) and includes all known and naturally occurring HER3 molecules including full length HER3 protein, fragments thereof such as the extracellular domain (ECD), as well as nucleic acids encoding said protein and fragments, as determinable from the context used. HER3 includes, but is not limited to, mammalian HER3 such as human HER3. In humans, HER3 is encoded by the ERBB3 gene.

As used herein, an antibody or binding fragment which "specifically binds HER3" is an agent which binds HER3, for example HER3-expressing cells as opposed to cells not expressing HER3 (as determined, e.g. via flow cytometric analysis) with a minimum affinity. The term "anti-HER2" antibody or binding fragment is also used herein for the same purpose.

As used herein, and unless otherwise specified, the term "antibody" refers to an immunoglobulin (Ig) molecule. The antibody may be from recombinant sources and/or produced in transgenic animals. The basic antibody structural unit is known to comprise a tetramer. Each tetramer is composed of two identical pairs of polypeptide chains, each pair having one light ("L") (about 25 kDa) and one heavy ("H") chain (about 50-70 kDa). The amino-terminal portion of each chain includes a variable region of about 100 to 110 or more amino acids primarily responsible for antigen recognition, and described in more detail below. The carboxy-terminal portion of each chain defines a constant region primarily responsible for effector function. The term "antigen-binding site" or "binding portion" refers to the part of the binding protein that participates in antigen binding. In an antibody, the antigen binding site is formed by amino acid residues of the N-terminal variable ("V") regions of the heavy and light chains. Three highly divergent stretches within the V regions of the heavy and light chains are also referred to as "hypervariable regions". In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs". Accordingly, the antibody in an embodiment comprises a heavy chain variable region or a heavy chain comprising a heavy chain complementarity determining region 1 (CDR-H1), heavy chain complementarity determining region 2 (CDR-H2) and heavy chain complementarity determining region 3 (CDR-H3), as well as a light chain variable region or light chain comprising a light chain complementarity determining region 1 (CDR-L1), light chain complementarity determining region 2 (CDR-L2) and light chain complementarity determining region 3 (CDR-L3). The CDRs are interposed between more conserved flanking stretches known as "framework regions", or "FRs". Thus, the term "FR" refers to amino acid sequences which are naturally found between, and adjacent to, hypervariable regions in immunoglobulins.

All CDRs and framework regions (FRs) disclosed herein, amino acid sequences of CDRs and FRs disclosed herein, and CDR-encoding or FR-encoding nucleic acid sequences disclosed herein, are intended to be defined in accordance with the Kabat numbering system (Kabat et al., 1991) unless otherwise indicated. Another system alternately employed in the art for such definitions is IMGT numbering (Lefranc et al., 2003).

In one embodiment, the present disclosure provides an antibody or binding fragment thereof comprising:
  (a) a light chain variable region and a heavy chain variable region, the light chain variable region comprising complementarity determining region CDR-L3 and the heavy chain variable region comprising complementarity determining region CDR-H3, wherein
     (i) CDR-L3 comprises an amino acid sequence having the formula YX$_1$X$_2$L (SEQ ID NO: 123), wherein X$_1$ is G or S and X$_2$ is W or Y and/or CDR-L3 comprises or consists of an amino acid sequence selected from the amino acid sequences set out in Table 1 (SEQ ID NOs: 9-18); and
     (ii) CDR-H3 comprises or consists of an amino acid sequence selected from SEQ ID NO: 6, 58-61 or the amino acid sequences set out in Table 2 (SEQ ID NOs: 19-57).

Accordingly, in one embodiment, an antibody or binding fragment thereof is provided comprising a light chain variable region and a heavy chain variable region, the light chain variable region comprising complementarity determining region CDR-L3 and the heavy chain variable region comprising complementarity determining region CDR-H3, wherein
  (i) CDR-L3 comprises or consists of the amino acid sequence QQYGWLPLT (SEQ ID NO: 3); and
  (ii) CDR-H3 comprises or consists of the amino acid sequence (SEQ ID NO: 6)
TDPYSLGGYYFDY.

Accordingly, in one embodiment, an antibody or binding fragment thereof is provided comprising a light chain variable region and a heavy chain variable region, the light chain variable region comprising complementarity determining region CDR-L3 and the heavy chain variable region comprising complementarity determining region CDR-H3, wherein
  (i) CDR-L3 comprises or consists of the amino acid sequence QQYGWLPLT (SEQ ID NO: 119); and
  (ii) CDR-H3 comprises or consists of the amino acid sequence (SEQ ID NO: 122)
TDPYSLGGYYFDY.

In another embodiment, an antibody or binding fragment thereof is provided comprising a light chain variable region and a heavy chain variable region, the light chain variable region comprising complementarity determining region CDR-L3 and the heavy chain variable region comprising complementarity determining region CDR-H3, wherein
(i) CDR-L3 comprises or consists of the amino acid sequence QQYSYPLT (SEQ ID NO: 91); and
(ii) CDR-H3 comprises or consists of the amino acid sequence

```
                                      (SEQ ID NO: 92)
ARAPSYSYGSYHYYYYYFDV.
```

In a further embodiment, the light chain variable region further comprises complementarity determining region CDR-L1 and/or CDR-L2 and/or the heavy chain variable region further comprises complementarity determining region CDR-H1 and/or CDR-H2, wherein
(iii) CDR-L1 comprises or consists of the amino acid sequence RASQGISNYLA (SEQ ID NO: 1);
(iv) CDR-L2 comprises or consists of the amino acid sequence AASSLQS (SEQ ID NO: 2);
(v) CDR-H1 comprises or consists of the amino acid sequence SY (SEQ ID NO: 4); and/or
(vi) CDR-H2 comprises or consists of the amino acid sequence

```
                                      (SEQ ID NO: 5)
VISYDGSNKYYADSVKG.
```

In another embodiment, the light chain variable region further comprises complementarity determining region CDR-L1 and/or CDR-L2 and/or the heavy chain variable region further comprises complementarity determining region CDR-H1 and/or CDR-H2, wherein
(iii) CDR-L1 comprises or consists of the amino acid sequence QGISNY (SEQ ID NO: 117);
(iv) CDR-L2 comprises or consists of the amino acid sequence AAS (SEQ ID NO: 118);
(v) CDR-H1 comprises or consists of the amino acid sequence GFTFSSYG (SEQ ID NO: 120); and/or
(vi) CDR-H2 comprises or consists of the amino acid sequence ISYDGSNK (SEQ ID NO: 121).

In another embodiment, the light chain variable region comprises the amino acid sequence set forth below:

```
                                      (SEQ ID NO: 7)
DIQMTQSPSSLSASVGDRVTITCRASQGISNYLAWYQQKPGKAPKLLIYA

ASSLQSGVPSRFSGSRSGTDFTLTISSLQPEDFATYYCQQYGWLPLTFGQ

GTKVEIK,
``` or an amino acid sequence having at least 70%, 75%, 80%, 85%, 90%, 95% or 99% sequence identity to SEQ ID NO: 7 or the framework regions of SEQ ID NO: 7.

In another embodiment, the light chain variable region consists of the amino acid sequence of SEQ ID NO: 7.

In another embodiment, the heavy chain variable region comprises the amino acid sequence set forth below:

```
                                      (SEQ ID NO: 8)
EVQLVESGGGLVQPGGSLRLSCAASGFTFSSYGMHWVRQAPGKGLEWVAV

ISYDGSNKYYADSVKGRFTISRDNSKNTLYLQMNSLRAEDTAVYYCARTD

PYSLGGYYFDYWGQGTLVTVSS,
``` or an amino acid sequence having at least 70%, 75%, 80%, 85%, 90%, 95% or 99% sequence identity to SEQ ID NO: 8 or the framework regions of SEQ ID NO: 8.

In another embodiment, the light chain variable region consists of the amino acid sequence of SEQ ID NO: 8.

In another embodiment, the light variable region comprises (i) the amino acid sequence of SEQ ID NO: 7 or an amino acid sequence having at least 70%, 75%, 80%, 85%, 90%, 95% or 99% sequence identity to the framework regions of SEQ ID NO: 7, and (ii) the heavy variable region comprises the amino acid sequence of SEQ ID NO: 8 or an amino acid sequence having at least 70%, 75%, 80%, 85%, 90%, 95% or 99% sequence identity to the framework regions of SEQ ID NO: 8.

Also provided is an antibody or antibody fragment comprising or consisting of the amino acid sequence of SEQ ID No: 83, 84, 85, 86, 87, 88, 89 or 90, or an amino acid sequence having at least 70%, 75%, 80%, 85%, 90%, 95% or 99% sequence identity to SEQ ID No: 83, 84, 85, 86, 87, 88, 89 or 90 or a fragment thereof. Further provided is an antibody or antibody fragment comprising or consisting of the amino acid sequence of SEQ ID No: 85 and 86 or SEQ ID NO: 89 and 90, or an amino acid sequence having at least 70%, 75%, 80%, 85%, 90%, 95% or 99% sequence identity to SEQ ID No: 85 and 86 or SEQ ID NO: 89 and 90, or a fragment thereof.

As used herein, the term "epitope" refers to the specific site or specific combination of sites/amino acids on an antigen that are bound by an antibody for example an antibody or binding fragment described herein. The HER3 epitope recognized by the antibodies and binding fragments described herein is comprised within the HER3 extracellular domain.

The present disclosure also provides an antibody or binding fragment that competes with an antibody or binding fragment as described herein for binding to HER3. Various methods are known in the art for determining if two antibodies and/or binding fragments compete for binding to the same antigen. For example, if the antibody or binding fragment being tested competes with the anti-HER3 antibody or binding fragment, is a decrease in binding to HER3 by the anti-HER3 antibody or binding fragment is seen. Methods for the testing binding to antigens include, but are not limited to, enzyme linked immunosorbent assay (ELISA) and other immunologically mediated techniques known within the art.

The present disclosure also provides an antibody or binding fragment thereof, wherein the antibody or binding fragment
(a) specifically binds HER3 with a dissociation constant ($K_D$) of less than or about 2.14 nM, and
(b) does not detectably inhibit growth of a HER3 expressing cell or cell line, or does not inhibit growth of a HER3 expressing cell or cell line by more than about 1, 5, 10, 15 or 25%.

In one embodiment, the antibody or binding fragment thereof does not inhibit growth of a HER3 expressing cell or cell line by more than about 1, 5, 10, 15 or 25% compared to a HER3 expressing cell or cell line not contacted with the antibody or fragment thereof.

In another embodiment, the antibody or binding fragment specifically binds HER3 with a $K_D$ of less than or about 4.0 nM, 3.8 nM, 3.6 nM, 3.4 nM, 3.2 nM, 3.0 nM, 2.8 nM, 2.6 nM, 2.4 nM, 2.2 nM, 2.0 nM, 1.8 nM, 1.6 nM, 1.4 nM, 1.2 nM, 1.0 nM, 0.8 nM, 06 nM, 0.4 nM, 0.3 nM, 0.2 nM, 0.1 nM, 50 µM, 10 µM or 1 µM. In a further embodiment, the antibody or binding fragment specifically binds HER3 with a $K_D$ of 1 µM to 3.0 nM, optionally 0.1 nM, 50 µM, 10 µM or 1 µM to 3.0 nM.

In one embodiment, the "antibody or binding fragment" is selected from a fragment antigen-binding (Fab), single-chain Fv (scFv), single-chain Fab (scFab), Fab', Fv, chemically linked F(ab')₂, dsFv, dsFv', sc(Fv)₂, ds-scFv, (dsFv)2, scFv-Fc, scFV-C$_H$3, single-chain immunoglobulin (e.g. scIgG), single-domain antibody (sdAb, nanobody), scFv-Fc, minibody (scFv-C$_H$3), diabody, tribody, tetrabody, multimeric antibody (e.g. scFv dimer, bivalent diabody), multispecific antibody (e.g. bispecific antibody, trispecific antibody, di-scFv, tri-scFv, bispecific Fab₂, trispecific Fab₂, trispecific triabody, trispecific Fab₃), multimeric/multispecific antibody (e.g. scFv dimer, bispecific diabody, dsFv-dsFv'), heavy-chain antibody, Fab₃, divalent VHH, pentavalent VHH (pentabody), (scFv-SA)₄ or [sc(Fv)2]₂.

In another embodiment, the "antibody or binding fragment" is selected from a scFv, Fab, diabody, scFv-C$_H$3, scFv-Fc or IgG.

In another embodiment, the "antibody or binding fragment" is selected from a Fab, sc(Fv)₂, scFv-C$_H$3, scFv-Fc or IgG.

Fab, Fab' and F(ab')2, scFv, dsFv, ds-scFv, scFv-C$_H$3, scFv-Fc, IgG, dimers, minibodies, diabodies, bispecific antibody fragments and other fragments can be synthesized by recombinant techniques.

Antibodies can also be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments.

In one embodiment, the antibody or binding fragment is an antibody, such as a human antibody, containing engineered variable regions (e.g. containing variable regions selected from a phage display library displaying engineered antibody variable regions, e.g. a phage-Fab library or a phage-scFv library,), or a chimeric antibody comprising human constant regions and an antibody variable region of a non-human mammal. The antibody or binding fragment may be a humanized antibody, e.g. an antibody comprising human constant regions, human variable region framework regions, and HER3-binding CDRs generated in a non-human mammal. The non-human mammal may be a rodent, such as a mouse, rat, rabbit, guinea pig or hamster. Alternately, the non-human mammal may be an ungulate, such as a camelid or a bovid.

In another embodiment, the antibody or binding fragment is a human antibody, such as an IgG1 antibody, wherein the heavy chain constant regions are gamma1 heavy chain constant regions. In other embodiments, the antibody or binding fragment is a human antibody, such as an IgA1, IgA2, IgD, IgG2, IgG3, IgG4, IgE or IgM antibody, wherein the heavy chain constant regions are alpha1, alpha2, delta, gamma2, gamma3, gamma4, epsilon or mu heavy chain constant regions, respectively.

In a further embodiment, the antibody or binding fragment is a monoclonal antibody. As used herein, a "monoclonal" antibody or binding fragment of the disclosure refers to a population of identical antibodies, for example a population of antibodies where the CDRs are identical in all the molecules of the population. Various procedures known within the art may be used for the production of monoclonal antibodies (see, for example, Greenfield, 2013). Monoclonal antibodies are commonly alternatively referred to using the abbreviations "mAb" or "MAb".

The antibody or binding fragment thereof is optionally an isolated antibody or binding fragment. The term "isolated antibody or binding fragment" or "isolated and purified antibody or binding fragment" refers to an antibody or binding fragment thereof that is substantially free of cellular material or culture medium when produced by recombinant DNA techniques, or chemical precursors, or other chemicals when chemically synthesized and/or other antibodies, for example directed to a different epitope.

It can be desirable to modify an antibody or binding fragment disclosed herein with respect to effector function, so as to enhance its effectiveness in binding HER3. For example, where the antibody or binding fragment comprises an antibody Fc region, such as an antibody, cysteine residue(s) can be introduced into the COOH terminal of the Fc region, thereby allowing interchain disulfide bond formation between antibody monomers in this region.

Functional variants of the antibodies and binding fragments described herein are also encompassed by the present disclosure. The term "functional variant" as used herein includes one or more amino acid and/or nucleotide modifications in a sequence (polypeptide or nucleic acid respectively) for example, one or more modifications of a light chain or a heavy chain complementarity determining region (CDR) disclosed herein that perform substantially the same function as the light chain and heavy chain CDRs disclosed herein in substantially the same way. For instance, variants of the CDRs disclosed herein have the same function of being able to specifically bind to the same epitope on HER3 as Fab HER3-3. In one embodiment, variants of CDRs disclosed herein include, without limitation, conservative amino acid substitutions. Variants of the CDRs also include additions and deletions to the CDR sequences disclosed herein. In addition, variant nucleotide sequences and polypeptide sequences include analogs and derivatives thereof.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative amino acid substitutions include:

| Conservative Substitutions | |
| --- | --- |
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

Thus, in one embodiment, the present disclosure includes functional variants to the amino acid sequences disclosed herein.

In particular, the disclosure provides functional variants of the CDR sequences disclosed herein. In one embodiment, functional variants of the CDR sequences of the light and heavy chains disclosed herein have at least 70%, 75%, 80%, 85%, 90%, 95% or 99% sequence identity with the CDR sequences disclosed herein. In another embodiment, functional variants of the CDR sequences disclosed herein comprise at least 1, 2, 3 or 4 amino acid substitutions, optionally conservative substitutions, in the CDR sequences disclosed herein.

The disclosure also provides functional variants of the amino acid sequences of the light chain and heavy chain of HER3-3. In one embodiment, the variant amino acid sequences of the amino acid sequences disclosed herein comprise sequences having at least 70%, 75%, 80%, 85%, 90%, 95% or 99% sequence identity to SEQ ID NOS: 7 and 8 or sequences having at least 70%, 75%, 80%, 85%, 90%, 95% or 99% to the framework regions of SEQ ID NOS: 7 or 8.

The term "sequence identity" as used herein refers to the percentage of sequence identity (also referred to herein as "percent identity") between two amino acid sequences or two nucleic acid sequences. To determine the percent identity of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence). For antibodies, percentage sequence identities can be determined when antibody sequences maximally aligned by IMGT or Kabat or other numbering convention. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions·times·100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul, 1990, modified as in Karlin and Altschul, 1993. Such an algorithm is incorporated into the NBLAST and XBLAST programs of Altschul et al., 1990. BLAST nucleotide searches can be performed with the NBLAST nucleotide program parameters set, e.g. for score=100, wordlength=12 to obtain nucleotide sequences homologous to a nucleic acid molecules of the present disclosure. BLAST protein searches can be performed with the XBLAST program parameters set, e.g. to score-50, wordlength=3 to obtain amino acid sequences homologous to a protein molecule of the present invention. To obtain gapped alignments for comparison purposes, Gapped BLAST can be utilized as described in Altschul et al., 1997. Alternatively, PSI-BLAST can be used to perform an iterated search which detects distant relationships between molecules. When utilizing BLAST, Gapped BLAST, and PSI-Blast programs, the default parameters of the respective programs (e.g. of XBLAST and NBLAST) can be used (see, e.g. the NCBI website). Another non-limiting example of a mathematical algorithm utilized for the comparison of sequences is the algorithm of Myers and Miller, 1988. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

Also provided in the present disclosure are nucleic acids encoding the antibodies, binding fragment, variable regions and CDRs described herein. As used herein, the term "nucleic acids" includes isolated nucleic acids as well as single stranded nucleic acid sequences, double stranded nucleic acid sequences and cDNA.

In particular the present disclosure provides nucleic acids encoding the CDR regions of disclosure herein (for example, CDRs corresponding to SEQ ID Nos 1-6 and 9-57), and functional variants thereof; and nucleic acids encoding the amino acid sequences of the light chain and heavy chain variable domain of HER3-3 as set out in SEQ ID NOs: 7 and 8, respectively, and functional variants thereof.

In another embodiment, the present disclosure includes functional variants to the nucleic acid sequences that encode the amino acid sequences disclosed herein. In addition, the functional variants include nucleotide sequences that hybridize to the nucleic acids encoding the amino acid sequences of the present disclosure, or the complement thereof, under at least moderately stringent hybridization conditions.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature ($Tm=81.5°$ C.$-16.6$ (Log 10 [Na+])$+0.41$(% (G+C)$-600/l$), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

Antibodies and binding fragments disclosed herein can be expressed by a vector containing a nucleic acid encoding the polypeptide of interest using methods which are well known and routinely practiced in the art. Accordingly, the present disclosure also provides a vector expressing any of the nucleic acids described herein.

The antibodies and binding fragments can be prepared by constructing a nucleic acid encoding an antibody or binding fragment, inserting the construct into an expression vector, and then expressing it in appropriate host cells. Vectors useful for expressing the antibodies and binding fragments disclosed herein are well known in the art. In one embodiment, the vector includes suitable translation initiation and termination signals in operable reading phase with a functional promoter and can comprise one or more phenotypic selectable markers and an origin of replication to ensure maintenance of the vector and, if desirable, to provide amplification within the host. In addition to vectors, the nucleic acids of the present disclosure can be delivered to a cell or a subject via any other method known in the art including, but not limited to, liposomes, naked DNA, adjuvant-assisted DNA, gene gun, catheters, etc.

Non-covalent interactions occur between an antibody or binding fragment thereof and an antigen for which the antibody or binding fragment is specific. The strength, or affinity of immunological binding interactions can be expressed in terms of the dissociation constant ($K_D$) of the interaction, wherein a smaller $K_D$ represents a greater affinity. Immunological binding properties of specific polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation (see, e.g. Malmqvist, 1993). The ratio of $K_{off}/K_{on}$ enables the cancellation of all parameters not related to affinity, and is equal to the dissociation constant $K_D$ (see, e.g. Davies et al., 1990).

As described in Example 1, Fab HER3-3 binds HER3 with a $K_D$ of 2.14 nM.

Accordingly, in one embodiment, the antibody or binding fragment thereof has a $K_D$ for HER3 specific binding of about or less than 4.0 nM, 3.8 nM, 3.6 nM, 3.4 nM, 3.2 nM, 3.0 nM, 2.8 nM, 2.6 nM, 2.4 nM, 2.2 nM, 2.0 nM, 1.8 nM, 1.6 nM, 1.4 nM, 1.2 nM, 1.0 nM, 0.8 nM, 06 nM, 0.4 nM, 0.3 nM, 0.2 nM, 0.1 nM, 50 µM, 10 µM or 1 µM. In another embodiment, the antibody or binding fragment specifically binds HER3 with a $K_D$ of 1 µM to 3.0 nM, optionally 0.1 nM, 50 µM, 10 µM or 1 µM to 3.0 nM Immunoconjugates The present disclosure also provides an immunoconjugate comprising
(1) an antibody or binding fragment thereof that specifically binds HER3,
(2) an effector agent, optionally linked directly or indirectly to the antibody or binding fragment thereof; and
(3) optionally a linker linking the antibody or binding fragment thereof and the effector agent.

In one embodiment, the effector agent is a label or a tag, which can generate a detectable signal, directly or indirectly (also referred to herein as a detectable moiety). Examples of labels include radioactive isotopes such as 3H, 14C, 32P, 35S, 123I, 125I, 131I. Other examples of labels include, but are not limited to, peptide tags, enzymes (for example, beta-galactosidase, HRP or alkaline phosphatase), proteins (for example phycoerythrin or biotin/streptavidin), magnetic particles, chromophores, fluorescent molecules, chemiluminescent molecules (or example, fluorescein isothiocyanate, rhodamine or luciferin), imaging agents, metal ions and dyes. One exemplary label is the fluorescent compound IRDye 8000W. Other fluorescent compound contemplated herein include, but are not limited to IRDye700DX, Cy5/7 and FITC. In another embodiment, the label is a radionuclide. Examples of radionuclides include, but are not limited to, 89Zr, 111Im, 68Ga, Tc99m, 11C, 13N, 15O, 18F, 124I, 68Ga, 62Cu, 64Cu, 99mTc, 123I, 212Bi, 131I, 131In, 90Y, and 186Re. The tag can also be a purification tag such as a His-tag, a HA-tag, a GST-tag, biotin or a FLAG-tag.

In another embodiment, the effector agent is a therapeutic agent. Therapeutic agents include, but are not limited to, cancer therapeutic agents (chemotherapeutic)/antineoplastic agents.

In another embodiment, the therapeutic agent is a toxin, for example, a cytotoxin. The toxin may be an enzymatically active toxin of bacterial, fungal, plant, or animal origin, or a fragment thereof. Toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, the toxin is a microtubule stabilizer, a microtubule destabilizer, an auristatin, a dolastatin, a maytansinoid, a tubulysin, a cryptophycins, a methionine aminopeptidase, a calicheamicin, an inhibitor of nuclear export of proteins CRM1, a DPPIV inhibitor, a proteasome inhibitor, an inhibitor of phosphoryl transfer reactions, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a pro-apoptotic agent, a Bcl2 inhibitor, an MCL1 inhibitor, a HSP90 inhibitor, an IAP inhibitor, an mTor inhibitor, N(2')-deacetyl-N(2')-(3-mercapto-1-oxopropyl)-maytansine (DM1), or N(2')-deacetyl-N2-(4-mercapto-4-methyl-1-oxopentyl)-maytansine (DM4).

Radioconjugated antibody or binding fragments of the disclosure, may be employed to bind radionuclides to HER3-expressing cells as a cytotoxic treatment of the cells. described above, a variety of radionuclides are available for the production of radioconjugated antibodies. Examples include 89Zr, 111Im, 68Ga, Tc99m, 11C, 13N, 15O, 18F, 124I, 68Ga, 62Cu, 64Cu, 99mTc, 123I, 212Bi, 131I, 131In, 90Y, and 186Re.

Conjugation may be accomplished by any chemical reaction that will bind an effector agent and an antibody or binding fragment thereof of the disclosure, so long as these retain their respective activities/characteristics for the intended use thereof. This linkage can include many chemical mechanisms, for instance covalent binding, affinity binding, intercalation, coordinate binding and complexation. In embodiments in which the immunoconjugate includes a linker, the linker may be stable or labile.

For example, immunoconjugates of an antibody or binding fragment thereof of the disclosure and an effector agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987).

Carbon-14-labeled 1-isothiocyanatobenzyl-3-methyldiethylene triaminepentaacetic acid (MX-DTPA) is an exemplary chelating agent for conjugation of radionucleotide to the antibody (see, e.g. WO94/11026).

Compositions

The disclosure also provides compositions including pharmaceutical compositions comprising an antibody or binding fragment thereof described herein or an immunoconjugate described herein as an active ingredient and a pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin.

A pharmaceutical composition is formulated to be compatible with its intended route of administration. Examples of routes of administration include parenteral, e.g. intravenous, intradermal, subcutaneous, oral (e.g. inhalation), transdermal (i.e., topical), transmucosal, and rectal administration.

In one embodiment, the active ingredient is prepared with a carrier that will protect it against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In one embodiment, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms are dictated by and directly dependent on the unique characteristics of the active ingredient and the particular therapeutic effect to be achieved, and the limitations inherent in the art of preparing such an active ingredient for the treatment of individuals.

The formulation can also contain more than one active ingredient as necessary for the particular indication being treated, optionally those with complementary activities that do not adversely affect each other. Alternatively, or in addition, the pharmaceutical composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

Method and Uses

Another aspect of the disclosure is a method for producing antibody and/or binding fragment thereof as disclosed herein.

In one embodiment, the antibody is isolated from an antibody library. For example, the antibody library can be an antibody phage-display library. In one embodiment, the antibody phage-display library is a single framework synthetic Fab library.

As described below, high throughput, phage-display technology was used to generate Fab HER3-3. A phage-displayed synthetic Fab library was screened against the antigen (HER3 extracellular domain) using established methods. The CDR regions randomized in the synthetic antibody library used were light chain 3 (CDR-L3) and heavy chain 3 (CDR-H3).

In another embodiment, the isolated and purified antibody and/or binding fragment thereof is affinity matured.

A person skilled in the art will appreciate that several methods can be used to produce antibodies and/or binding fragments thereof as described herein. A method that can be used is a phage display method.

In another embodiment, a nucleic acid encoding an antibody described herein is expressed in a host cell to make the antibody and/or binding fragment thereof. In an embodiment, the method comprises:
  (a) expressing in a host cell a nucleic acid encoding an antibody and/or binding fragment thereof herein disclosed;
  (b) culturing the host cell to produce the antibody and/or binding fragment thereof; and
  (c) isolating and/or purifying the antibody and/or binding fragment thereof from the host cell.

In some embodiments, a nucleic acid encoding a single chain antibody is expressed. In other embodiments, multiple nucleic acids are expressed, for example encoding a nucleic acid encoding an antibody light chain and a nucleic acid encoding an antibody heavy chain.

Suitable host cells and vectors are described above. Vectors and nucleic acids encoding an antibody described herein may be introduced into mammalian cells via conventional techniques such as calcium phosphate or calcium chloride co-precipitation, DEAE-dextran mediated transfection, lipofectin and other liposome based transfection agents, electroporation or microinjection.

Nucleic acid encoding an antibody described herein may be directly introduced into mammalian cells using delivery vehicles such as retroviral vectors, adenoviral vectors and DNA virus vectors.

The disclosure also provides uses and methods relating to the antibodies and binding fragments thereof described herein.

Detecting HER3-Expressing Cells

The antibodies and binding fragments thereof, immunoconjugates and compositions of the present disclosure are useful for detecting cells that express HER3. Accordingly, the disclosure provides a use of the antibodies and binding fragments thereof, immunoconjugates and compositions described herein for targeting, binding and/or detecting HER3-expressing cells, optionally cells that express HER3 on the cell surface. In one embodiment, the HER3-expressing cells are cancer cells, including, but not limited to, breast cancer cells, gastric cancer cells, non-small cell lung cancer cells, head and neck squamous cell carcinoma cells and colon cancer cells.

The antibodies and binding fragments thereof, immunoconjugates and compositions of the present disclosure are useful for detecting and/or quantitating levels of expression of HER3. Accordingly, the disclosure provides a use of the antibodies and binding fragments thereof, immunoconjugates and compositions described herein for detecting and/or quantitating levels of expression of HER3 in a sample, optionally a cell sample. In one embodiment, the expression is cell-surface expression of HER3.

In general, the use of binding agents for detection and/or quantitation of analytes, such HER3 protein, optionally surface-expressed HER3 is well known in the art and may be achieved through the application of numerous approaches. These methods are generally based upon the detection of a label or marker, such as radioactive, fluorescent, biological and enzymatic tags. Examples of methods include, but are not limited to, Western blotting, enzyme linked immunosorbent assay (ELISA), immunofluorescence, immunohistochemistry, flow cytometry and in vivo imaging techniques such as PET or SPECT imaging.

Accordingly, in one embodiment, the disclosure provides a method of detecting a HER3 expressing cell in a sample, the method comprising:
   a) contacting the sample with an antibody or binding fragment, immunoconjugate or pharmaceutical composition described herein under conditions to form an antibody:HER3 complex; and
   b) detecting the presence of the antibody:HER3 complex.

In one embodiment, the method further comprises determining the amount of the antibody:HER3 complex.

In another embodiment, the disclosure provides a method of detecting a HER3 expressing cell in a sample, the method comprising:
   (a) contacting the sample with an antibody or binding fragment, immunoconjugate or pharmaceutical composition described herein; and
   (b) detecting binding of the antibody or binding fragment, immunoconjugate or pharmaceutical composition to the sample.

In one embodiment, an increase in binding of the antibody or binding fragment, immunoconjugate or pharmaceutical composition to the sample as compared to binding of the antibody or binding fragment, immunoconjugate or pharmaceutical composition to a control sample detects a HER3 expressing cell in the sample.

The "control sample" is optionally a sample from a healthy individual and/or a sample comprising cells that do not detectably express HER3.

In another embodiment, the method further comprises determining the amount of antibody or binding fragment, immunoconjugate or pharmaceutical composition bound to the sample.

In one embodiment, the sample is a patient sample, such as a cancer sample from a cancer patient. Alternately, the sample may be a control sample. Embodiments of the sample include but are not limited to, a sample of cultured cells, cultured cell supernatant, cell lysate, serum, blood plasma, biological fluid or biological tissue. In other embodiments, the sample is obtained from a cancer. In certain embodiments, the sample is a biopsy sample.

In an embodiment, the complex is detected directly for example wherein the antibody is labeled with a detectable tag or fusion moiety. In an embodiment, the complex is detected indirectly using a secondary antibody specific for the antibody:HER3 complex.

In an embodiment, detecting is performed using Western blotting, enzyme linked immunosorbent assay (ELISA), immunofluorescence, immunohistochemistry, flow cytometry, immunoprecipitation, immunoblot, immunocytochemistry proximity ligation assay (PLA), mass spectroscopy-based techniques and fluorescence-activated cell sorting (FACS), proximity ligation assay (PLA), mass spectroscopy-based techniques and in vivo imaging techniques such as PET or SPECT imaging.

Detecting can be performed using methods that are qualitative or measured using quantitative methods, for example by comparing to a control value, a standard or standard curve.

The detection of HER3-expressing cells can be used in a number of applications, including, but not limited to, patient imaging (for example, PET or SPECT imaging) and image-guided surgery.

Accordingly, in one embodiment, a method of detecting a HER3 expressing cell in a subject is provided, the method comprising:
   a) administering an antibody or binding fragment, immunoconjugate or pharmaceutical composition described herein said subject and
   b) subjecting said subject to imaging.

In another embodiment, a use of an antibody or binding fragment, immunoconjugate or pharmaceutical composition described herein for use in imaging a subject is provided.

In one embodiment, the antibody or binding fragment is labelled with a detectable moiety such as a fluorescent compound or a radionuclide.

As used herein, the term "subjecting a subject to imaging" refers to performing imaging on the subject to allow visualization of the antibody or binding fragment of interest. In one embodiment, the imaging comprises SPECT (Single-photon Emission Computed Tomography) or PET (Positron Emission Tomography) imaging. Other methods of imaging include, but are not limited to, fluorescence imaging, magnetic resonance imaging (MRI), scintigraphy, gamma camera, a β+ detector, a γ detector or a combination thereof. In another embodiment, the imaging comprises image guided surgery.

In one particular embodiment, the antibody or binding fragment is labelled with radionuclide 89Zr and the imaging is PET imaging. In another particular embodiment, the antibody or binding fragment is labelled with radionuclide 89Zr and Tc99m and the imaging is SPECT imaging. In a further embodiment, the antibody or binding fragment is labelled with IRDye800CW or IRDye700DX and the imaging comprises image guided surgery.

In one embodiment, antibody or binding fragment or immunoconjugate is administered to the subject by intravenous injection or is formulated for administration to the subject by intravenous injection.

Diagnostic Methods

As described above, the antibodies and binding fragments thereof, immunoconjugates and pharmaceutical compositions described herein are useful in the detection and/or quantitation of HER3-expressing cells in patient samples or in control samples of healthy individuals and accordingly may be useful diagnostics. For example, the antibodies and binding fragments thereof, immunoconjugates and pharmaceutical compositions of the disclosure can be used to detect and/or quantitate total cellular expression of HER3 and/or cell-surface expressed HER3. As used herein, the term "diagnostics" encompasses screening, stratification, monitoring and the like.

In one embodiment, the disclosure provides a method for screening, for diagnosing or for detecting a HER3 expressing cancer, the method comprising:
   (a) measuring the level of HER3 in a sample from a subject optionally using an antibody or assay herein disclosed; and
   (b) comparing the level of HER3 in the sample with a control, wherein an increased level of HER3 in the sample compared to the control is indicative that the subject has a HER3 expressing cancer.

In an embodiment, the control is a control value derived from a group of subjects without a HER3 expressing cancer e.g. normal controls.

The HER3 expressing cancer is optionally breast cancer, gastric cancer, non-small cell lung cancer, head and neck squamous cell carcinoma or colon cancer.

Treatment of Cancer

HER3 has been shown to play an important role in various cancers.

As described above, the present disclosure provides immunoconjugates comprising:
(1) an antibody or binding fragment thereof that specifically binds HER3,
(2) an effector agent, optionally linked directly or indirectly to the antibody or binding fragment thereof; and
(3) optionally a linker linking the antibody or binding fragment thereof and the effector agent.

where the effector agent is optionally a toxin or an anti-neoplastic agent.

Accordingly, the present disclosure provides a method of using an immunoconjugate disclosed herein for treating a HER3 expressing cancer, the method comprising administering an effective amount of an immunoconjugate disclosed herein to an animal or cell in need thereof, optionally wherein the HER3 expressing cancer is breast cancer, non-small cell lung cancer, head and neck squamous cell carcinoma or colon cancer.

In one embodiment, an effective amount of an immunoconjugate disclosed herein is used for treating a HER3 expressing cancer, optionally wherein the HER3 expressing cancer is breast cancer, gastric cancer, non-small cell lung cancer, head and neck squamous cell carcinoma or colon cancer. In another embodiment, an immunoconjugate disclosed herein is used in the preparation of a medicament for treating or preventing a cancer, optionally wherein the cancer is breast cancer, non-small cell lung cancer, head and neck squamous cell carcinoma or colon cancer.

As used herein, the terms "subject" and "animal" include all members of the animal kingdom, in one embodiment the subject is a mammal. In a further embodiment the subject is a human being. In one embodiment, the subject is a patient having a disease, such as a cancer, associated with HER3-expressing cells.

An effective amount of an immunoconjugate or pharmaceutical composition of the disclosure relates generally to the amount needed to achieve a therapeutic objective. Common ranges for therapeutically effective dosing of an immunoconjugate or pharmaceutical composition of the disclosure may be, by way of non-limiting example, from about 0.1 mg kg body weight to about 50 mg/kg body weight. Common dosing frequencies may range, for example, from twice daily to once a week.

Efficaciousness of treatment is determined in association with any known method for diagnosing or treating the particular cancer. Alleviation of one or more symptoms of the cancer indicates that the antibody confers a clinical benefit.

As used herein, "treating a cancer" includes, but is not limited to, reversing, alleviating or inhibiting the progression of the cancer or symptoms or conditions associated with the cancer. "Treating the cancer" also includes extending survival in a subject. Survival is optionally extended by at least 1, 2, 3, 6 or 12 months, or at least 2, 3, 4, 5 or 10 years over the survival that would be expected without treatment with an immunoconjugate or pharmaceutical composition as described herein. "Treating the cancer" also includes reducing tumour mass and/or reducing tumour. Optionally, tumour mass and/or tumour burden is reduced by at least 5, 10, 25, 50, 75 or 100% following treatment with an immunoconjugate or pharmaceutical composition as described herein. "Treating the cancer" also includes reducing the aggressiveness, grade and/or invasiveness of a tumour.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

EXAMPLES

The following non-limiting examples are illustrative of the present disclosure:

Example 1

The design, construction, and validation of a phage-displayed, single-framework, synthetic Fab library is described. The new library, named Library-S, was built on a modified trastuzumab framework. CDRs L1, L2, H1, and H2 were fixed to preserve the most-frequent 'canonical' CDR conformation preferred by the modified trastuzumab Fab framework. The library diversity was engineered within CDR-L3 and CDR-H3 using custom-designed trinucleotide phosphoramidite mixes and biased towards human antibody CDR diversities. The library was validated by conducting a solid-phase selection against the human epidermal growth factor receptor-3 ectodomain (HER3-ECD). Next generation sequencing (NGS) analysis was used to compare the diversity of the naïve library and the anti-Her3-ECD selection pool. Binding studies indicated that the most-frequent Fab sequence from the anti-Her3-ECD selection pool bound very tightly to recombinant HER3-ECD and cell-surface HER3. This anti-HER3 antibody however did not inhibit the viability of HER3 positive cell-lines. This property makes the HER3 binder useful as a molecular imaging reagent, and imaging studies showed selective accumulation of anti-HER3 Fab to HER3-positive xenografts in a mouse model.

Library-S Design

The Hu4D5-8 Fab framework was used to construct a new single-framework, synthetic Fab library (FIG. 1). Hu4D5-8 is based on the anti-HER2 antibody trastuzumab (Carter et al., 1992). It is thermostable (Tm 80° C.) and present in several approved antibody-based therapeutics (Na et al., 2016). Hu4D5-8 has been used successfully in other single framework phage-displayed Fab libraries (Fellouse et al., 2007; Persson et al., 2013). The variable light and heavy chain germ line sequences of Hu4D5-8 Fab framework are VK1-1 and VH3-23, respectively and are frequently seen in human antibody responses (Lee et al., 2004a)

Hu4D5-8 is the humanized version of the anti-HER2 mouse monoclonal antibody (Mu4D5) (FIG. 1). Humanization of Mu4D5 $V_L$ and $V_H$ domains requires 24 and 36 amino acid changes, respectively. The fully humanized antibody (Hu4D5-1) binds to HER2 with 80-fold lower affinity than Mu4D5 and does not inhibit HER2-overexpressing cells. To regain binding and anti-proliferative activity, two positions (E55Y and G66R) in the $V_L$ domain and five positions (R71A, D73T, L78A, A93S and V102Y) in the $V_H$ domain are reverted to the Mu4D5 sequences. These substitutions are in CDR anchor residues (positions 55 in $V_L$, 93 and 102 in $V_H$) and framework residues (positions 66 in $V_L$, and 71, 73, and 78 in $V_H$). Incorporation of these mutations results in anti-proliferative activity comparable to Mu4D5 and 3-fold stronger binding than Mu4D5 (Carter et al., 1992; Kelley et al., 1992; Eigenbrot et al., 1993).

Library-F is a well-characterized, single framework, synthetic Fab library built on Hu4D5-8 (Persson et al., 2013) and served as the starting point for Library-S construction (FIG. 1). Library-F has four variable CDRs (CDRH3, CDRH2, CDRH1, and CDRL3). It contains four murine residues in its framework (R66 in $V_L$ and A71, T73, and A78 in $V_H$) and two in CDR anchor residues (positions 55 in $V_L$ and 102 in $V_H$). To increase the functional diversity of Library-S, CDRs L1, L2, H1, and H2 were fixed with preferred canonical sequences. Previous studies showed that CDR sequences can be grouped based on their secondary structures and certain canonical CDR conformations are preferred by a given antibody framework (Martin and Thornton, 1996; Al-Lazikani et al., 1997; Morea et al., 1998). The use of such preferred CDR conformations in the library design improves the success rate and biophysical properties of synthetic Fab libraries (Rothe et al., 2008; Prassler et al., 2011; Tiller et al., 2013). In this work, Library-S was designed to accommodate the most frequent canonical CDR conformations preferred by the 4D5 Fab framework.

The $V_H3$ gene family has more than two-dozen functional genes and CDRH2 of the $V_H3$ family can adopt three different Chothia canonical CDRH2 structures (Chothia et al., 1992). The CDRH2 canonical conformation is determined by the $71^{st}$ residue in the $V_H$ domain (Rothe et al., 2008; Prassler et al., 2011; Tiller et al., 2013; Knappik et al., 2000; North et al., 2011). The $V_H3$-23 human germline gene, which represents 80% of the VH3 rearrangements (Prassler et al., 2011) has 71R in $V_H$ corresponding to Chothia H2-3A or H2-10-2 sequences (North et al., 2011). Since the human A71R residue from HuD45 was introduced into Library-S, T73N, and A78L mutations were also introduced into the FRM3 region of the Hu4D5-8 Fab framework for proper display of H2-10-2/H2-3A CDRH2 canonical loop (Carter et al., 1992; Kelley et al., 1992; Eigenbrot et al., 1993).

Figures 2, 3:
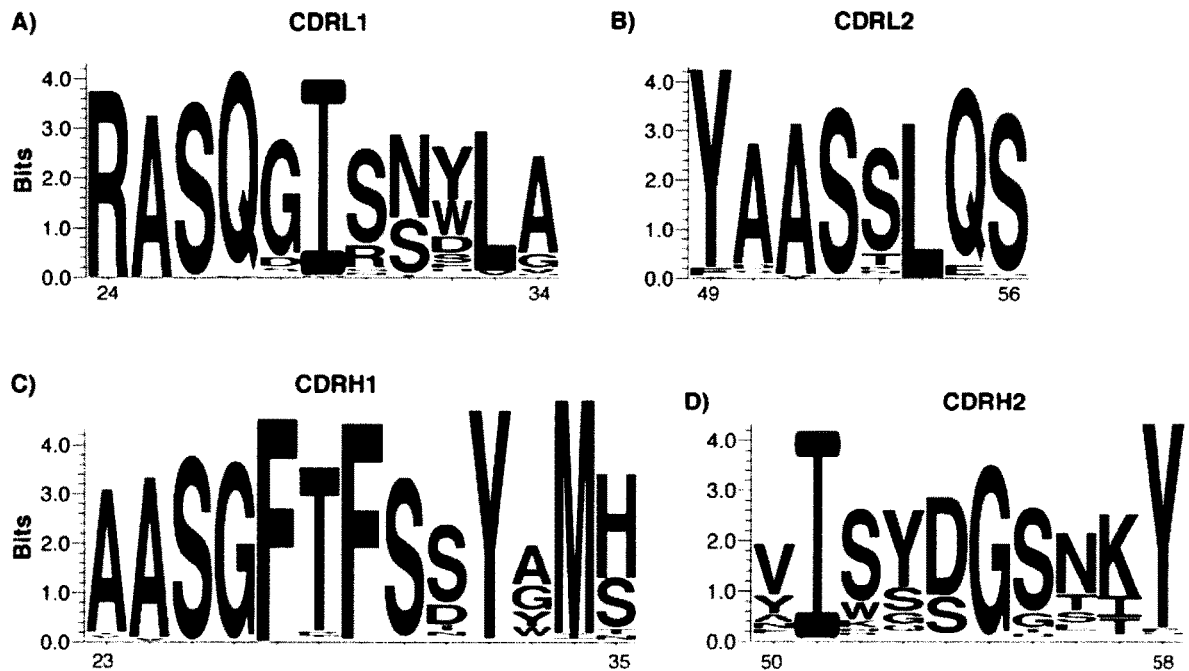

CDR consensus sequences were used to fix CDRs L1, L2, H1, and H2 in the Hu4D5-8 Fab framework. To do this, 100 $V_L$ kappa and 500 $V_H3$ sequences were collected using BLAST with the Hu4D5 sequence (FIG. 1) as an input. The BLAST consensus sequence (FIG. 2) was then compared to clusters identified previously (North et al., 2011). The fixed sequence for each CDR was selected by choosing the most abundant amino acid from the consensus sequence at each position (FIG. 2). These sequences correspond to the following canonical conformations L1-11-1, L2-8-1, H1-13-1, and H2-10-2 (North et al., 2011). Finally, it was verified that a structure containing the proposed fixed CDR sequence existed in the protein data bank (PDB). Relative to Hu4D5-8, which retains seven mouse residues, the 4D5 framework used in Library-S contains only one mouse residue (Arg66 in $V_L$).

To allow better sequence coverage during selections, library diversity was introduced only in two CDRs (L3 and H3). The overall design of Library-S is shown in FIG. 3. The CDRL3 length was fixed at nine amino acids. CDRL3 anchor residues (two at the N-terminus and three at the C-terminus of CDRL3) were fixed to favor the L3-9-cis7-1 canonical conformation (North et al., 2011). The central region (positions 91-94 encoded by the Vκ gene) was diversified using a custom-made codon mix (indicated as Z in FIG. 3) that encoded pre-defined proportions of thirteen amino acids (FIG. 3). The theoretical diversity in CDRL3 was $2.9 \times 10^4$. Since CDRH3 plays a dominant role in antigen recognition, CDRH3 was designed to contain length, amino acid, conformational, and joining-segment ($J_H$-region) diversities. 19 different CDRH3 lengths, ranging from 7 to 25 residues, were used in the Library-S design. Since an increase in $J_H6$ gene usage is observed with increasing CDRH3 lengths during the process of human VDJ-recombination (Zemlin et al., 2003), a $J_H6$ gene segment was incorporated in long CDRH3 sequences (16-25 residues), whereas a $J_H4$ gene segment was used for short CDRH3 sequences (7-16 residues). In CDRH3, amino acid diversity was introduced to the DH region (positions 95-99 encoded by the DH gene) using two different codon-mixes (indicated as Z and X in FIG. 3). For short to medium-sized CDRH3 lengths (7-16 residues), codon Z was used that encoded a pre-defined proportion of thirteen amino acids. For long CDRH3 lengths (16-25 residues), codon X was sued that encoded a pre-defined proportion of nine amino acids. Amino acids and their composition in Codon X were used from Library-F CDR design (Lee et al., 2004) Codon Z was designed to encode four additional amino acids (threonine, arginine, glutamic acid, and leucine). Since charged residues have been shown to be important for high-affinity binding of antibodies (Burkovitch et al., 2016) arginine and glutamic acid were included into the amino acid set. One extra amino acid for the polar group (threonine) and one for the non-polar group (leucine) were also included. To introduce CDRH3 conformational diversity, key anchor residues within $J_H4$ or $J_H6$ segments were soft randomized to favor both the bulged and non-bulged CDRH3 conformations. The theoretical diversity in CDRH3 was $2.6 \times 10^{14}$. The theoretical diversity of Library-S was $7.4 \times 10^{18}$ members.

Library-S Construction and Quality Control

Library-S was constructed using an established M13 bacteriophage system that allows bivalent Fab display (Lee et al., 2004b). The Fab-4D5 encoding phagemid, with NotI restriction enzyme sites present in CDRs, was used as a template to construct Library-S. Kunkel mutagenesis was used to replace NotI sites with CDRs containing fixed or degenerate codons, encoding amino acid compositions shown in FIG. 3. Upon digestion of the non-mutated template DNA by NotI, library DNA from the Kunkel mutagenesis reaction was electroporated into SR320 an *E. coli* strain, which is resistant to lytic phage and suitable for high-efficiency transformation and phage production. To minimize biases in bacterial growth and phage production due to differences in CDRH3 lengths, Library-S was constructed using 20 Kunkel mutagenesis reactions. Each reaction contained an oligonucleotide of one CDRH3 length, resulting in 20 sub-libraries (SL1-SL20).

Figure 4:
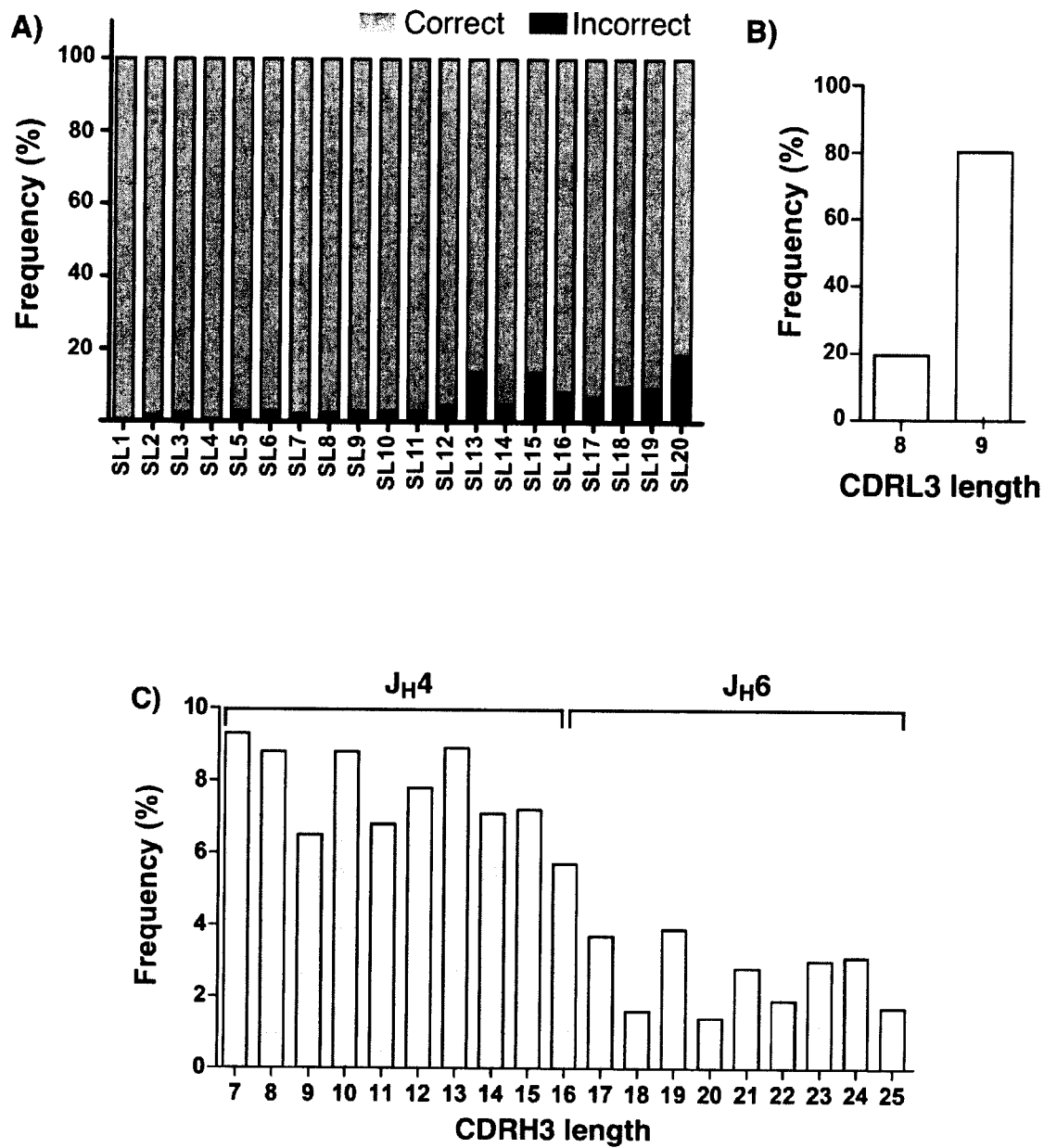

To assess the quality of sub-libraries, their CDRH3 regions were sequenced using Ion Torrent sequencing technology. On average ~1,000 filtered-reads were used per sub-library to determine the overall sequence composition. Except for SL13, SL15, and SL20, the proportion of incorrect sequences (sum of the out-of-frame sequences, template sequences, and sequences with stop codons) in sub-libraries was less than 10%. The average proportion of incorrect sequences present in 20 sub-libraries was only 5.7% (FIG. 4A). An equal number of phages from 20 sub-libraries were combined to make Library-S. To further assess Library-S quality, both diversified L3 and H3 CDRs were sequenced. 13,118 CDRL3 and 13,712 CDRH3 sequences were obtained and their overall sequence composition was determined. The proportion of incorrect CDRL3 and CDRH3 sequences was 1.8% and 3.4%, respectively. Since the library size was higher than the theoretical CDRL3 diversity, the proportion of unique CDRL3 sequences was only 40%. Also, for a few sub-libraries with short CDRH3 lengths, the library size was higher than the theoretical CDRH3 diversity, resulting in a decrease in the proportion of unique CDRH3 sequences to 81%. Considering the randomness in the pairing of CDRs L3 and H3, the actual proportion of unique Fabs is expected to increase in the library. After electroporation of library DNA into *E. coli*, the size of the library was estimated by bacteria titrations to be 9.4 billion. Based on the proportion of correct and unique CDRH3 sequences in sequencing analysis, it is estimated that there were 7.6 billion unique Fabs in the library.

Next, CDRL3 and CDRH3 sequences were analyzed in terms of length distribution. Although CDRL3 length was fixed to 9 residues, two different CDRL3 lengths were observed in the population (FIG. 4B). 20% of CDRL3 sequences had only 8 residues. For CDRL3 with 8 amino acids, one of the four diversified positions in the CDRL3 central region was absent. Considering that the Fab4D5 framework can accommodate CDRL3 lengths ranging from 8 to 12 residues (Persson et al., 2013), the CDRL3 sequences with 8 residues were not eliminated. With respect to CDRH3, 19 loop lengths were included in the design: lengths 7-16 had a $J_H4$ segment and lengths 16-25 had a $J_H6$ segment. Since an equal number of phages from 20 sub-libraries were mixed, it was expected to obtain a flat CDRH3 length distribution. However, the analysis showed that $J_H4$-containing CDRH3 sequences (74%) were more overrepresented than $J_H6$-containing CDRH3 sequences (26%) (FIG. 4C).

Next, the amino acid composition of CDRL3 and CDRH3 were analyzed. Sequence logo indicated that CDR diversification was uniform across variable positions and no major deviations were seen between expected and observed amino acid compositions of anchor residues. Sequence logos, representing CDRL3 (9aa sequences), $J_H4$ (15aa sequences) CDRH3 and $J_H6$ (19aa sequences) CDRH3, are shown in FIGS. 4D-F. To obtain a more detailed amino acid distribution, the frequency of 13 possible amino acids within the CDRL3 central region (FIG. 4G), 13 possible amino acids within the $D_H$ segment of $J_H4$-containing CDRH3 sequences (FIG. 4H), and 9 possible amino acids within the $D_H$ segment of $J_H6$-containing CDRH3 sequences (FIG. 4I) were analyzed. These regions had the highest diversity in the library and were encoded by one of two codon mixtures, X or Z, with predefined proportions of 9 and 13 amino acids, respectively. While the frequency of most residues were close to frequencies predefined in codons X and Z, tyrosine was overrepresented and glycine was underrepresented compared to designed oligonucleotides.

Generation and Characterization of HER3 Binders from Library-S

To test the ability of Library-S to produce high affinity Fabs, the human epidermal growth factor receptor-3 (HER3) was used as a target. HER3 is a member of the epidermal growth factor receptor (ErbB) family of receptor tyrosine kinases. The role of HER3 in disease resistance and prognosis make it a good therapeutic and imaging target (Ma et al., 2014; Zhang et al., 2015). To isolate anti-HER3 Fabs from Library-S four rounds of solid-phase selections against the HER3 ectodomain (HER3-ECD) were conducted. Briefly, the recombinant HER3-ECD-Fc fusion protein was immobilized on maxisorp plates and HER3-ECD-coated wells were incubated with Library-S deselected for binding to the Fc protein. Upon elimination of non-specific phages by washing, bound phages were eluted and amplified in *E. coli* overnight for subsequent rounds of panning. After each selection round, the number of phages eluted from HER3-ECD-coated wells relative to BSA-coated wells was calculated. A ~20-fold enrichment in target-specific phage number was observed after four rounds of selection.

Figure 5:
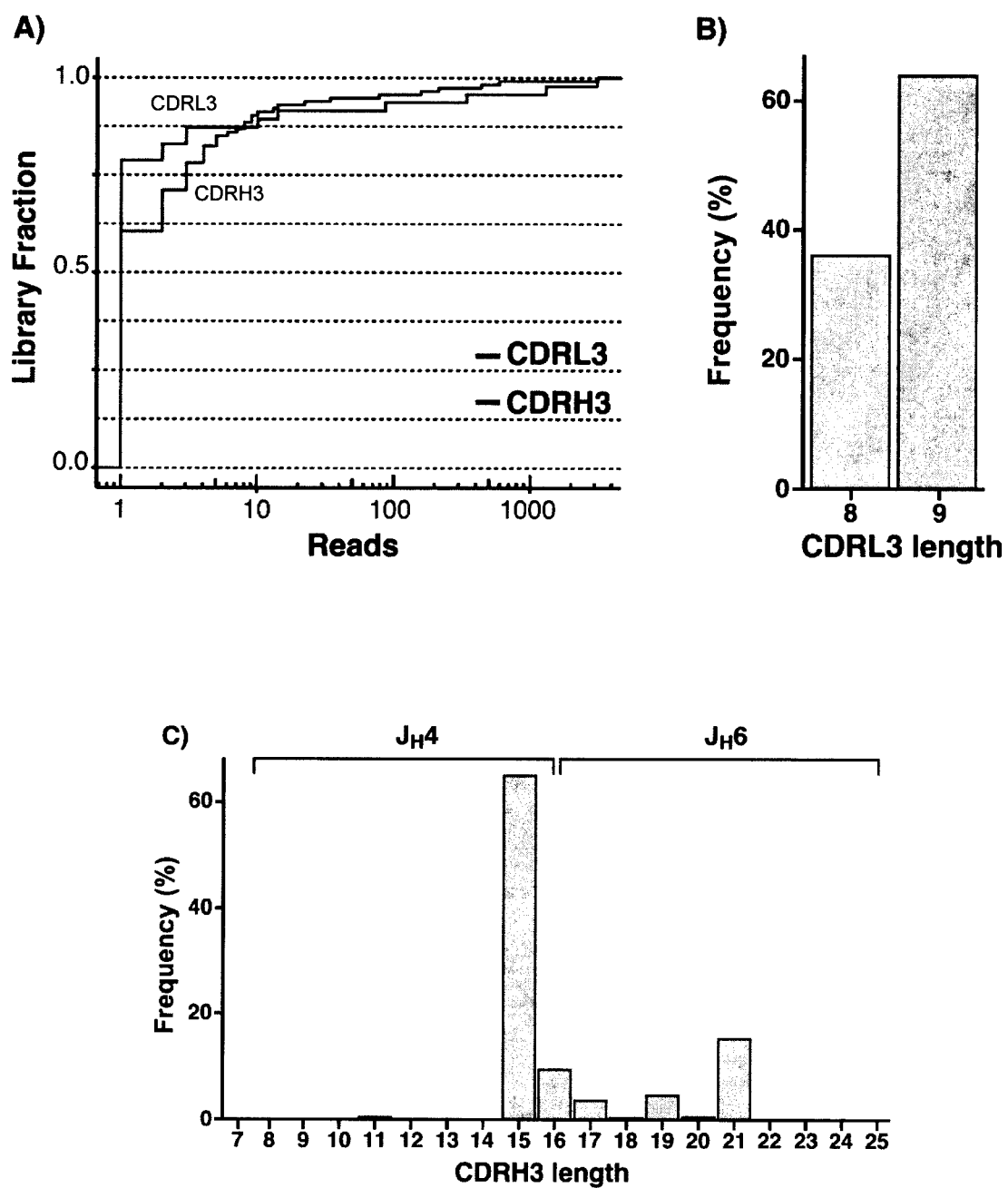

To determine the identity of anti-HER3 CDR sequences and to monitor the changes in library diversity post-selection, diversified CDR regions (CDRL3 and CDRH3) from the round-4 phage pool were subjected to Ion Torrent sequencing. ~4800 reads were obtained after filtering for both heavy and light chains. A plot of the cumulative distribution of read counts showed that the majority of sequences (>50%) occurred once, and a very small fraction of sequences (1 from heavy chain and 2 from light chain) had over 1000 reads (FIG. 5A). This indicated that there was a strong selection for HER3 binding, which resulted in dominant clones. Length analysis showed that both possible CDRL3 lengths were present in the selection pool. The most-frequent CDRL3 sequence had a length of 9 amino acids (FIG. 5B). CDRH3 length analysis showed that only 5 out of 19 possible CDRH3 lengths were present at greater than 4% after 4 rounds of selection. The proportion of JH4- and JH6-containing CDRH3 sequences were 66% and 34%, respectively. Among JH4-containing CDRH3 sequences, a significant enrichment was observed for CDRH3 length of 15 amino acids.

Among JH6-containing CDRH3 sequences, four CDRH3 lengths were seen above 4%. The second most frequent CDRH3 sequence had a length of 21 amino acids and possessed a JH6 segment (FIG. 5C). Sequence logos were generated to visualize the extent of amino acid conservation within diversified CDRs. CDRL3 had the consensus sequence Y(G/S)(W/Y)L (SEQ ID NO: 123) (FIG. 5D). The JH4-containing CDRH3 sequences were dominated by the sequence TDPYSLGGYY (SEQ ID NO: 124) (FIG. 5E). The JH6-containing CDRH3 sequences were diverse with no clear consensus sequences (FIG. 5F). Out of 13 possible amino acids within the CDRL3 central region only five were seen above 1% (FIG. 5G). Out of 13 possible amino acids within the DH segment of JH4-CDRH3 sequences only six were seen above 1%. Interestingly, an amino acid that was not included in the diversity design (aspartic acid) was observed at a frequency of 11% (FIG. 5H). Out of nine possible amino acids within the DH segment of JH6-CDRH3 sequences, only six were seen above 1% (FIG. 5I).

Figure 6:
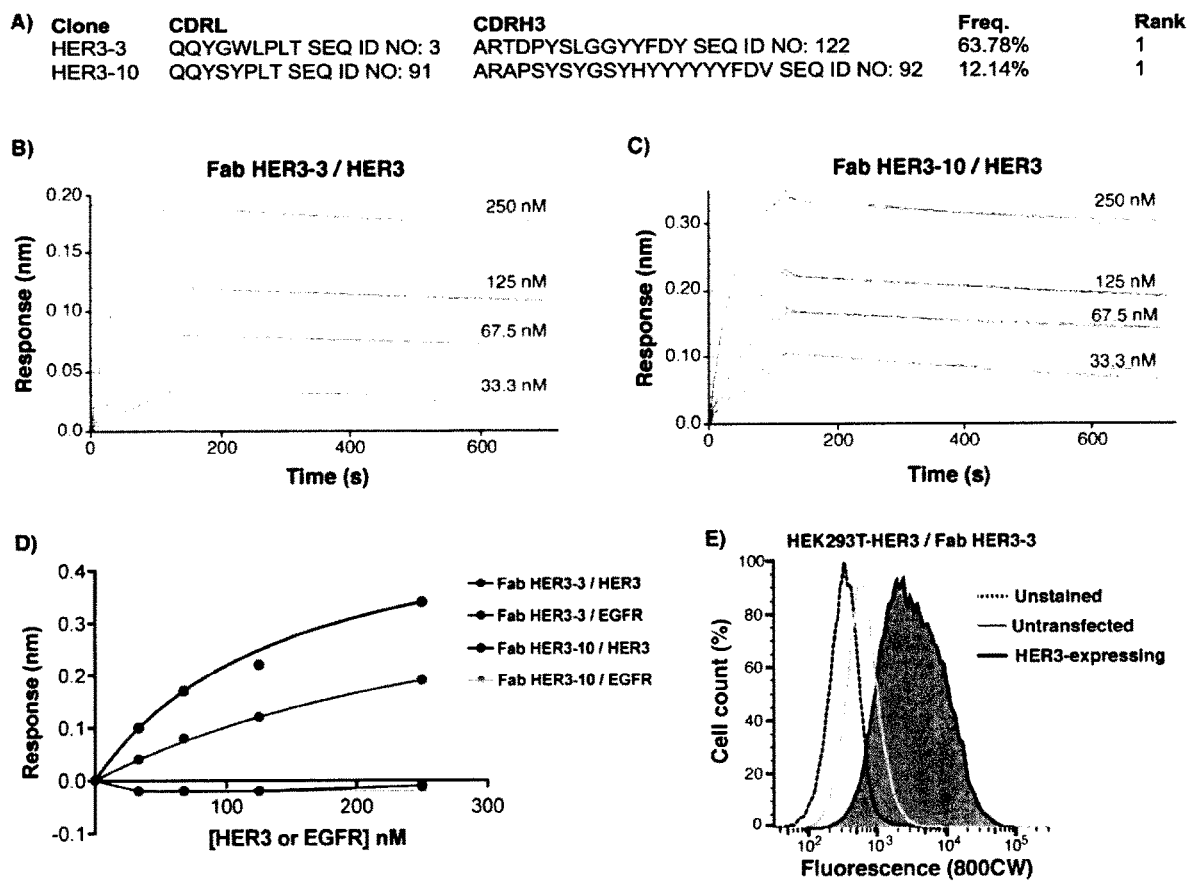
Figure 9:
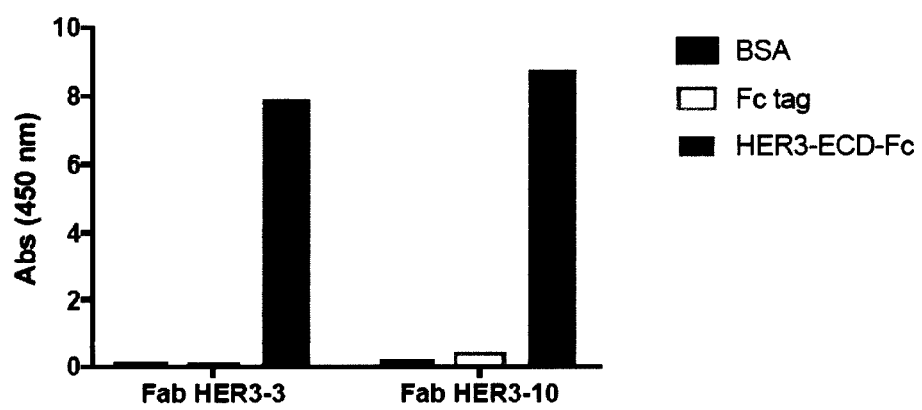

Random clone picking and Sanger sequencing of ten phagemids recovered two abundant Fab clones (HER3-3 and HER3-10) from the round-4 phage pool. Diversified CDR sequences and frequency of two Fab clones in the round-4 phage pool are shown in FIG. 6A. Fab HER3-3 contains a CDRH3 of 15 amino acids and a JH4 gene segment (YFDY; SEQ ID NO: 125) in CDRH3. Fab HER3-10 contains a CDRH3 of 21 amino acids and a JH6 gene segment (YYYYYFDV; SEQ ID NO: 126) in CDRH3. In phage-ELISA, phage-displayed Fabs HER3-3 and HER3-10 bound to HER3-ECD but not to BSA or the Fc protein. HER3-3 and HER3-10 were subcloned from the phagemid vector into a Fab expression vector, and expressed and purified Fabs from *E. coli* using Protein-L affinity chromatography (Fab expression ~10 mg/mL). In Fab-ELISA, purified Fabs HER3-3 and HER3-10 bound to HER3-ECD but not to BSA or the Fc protein (FIG. 9). Fab binding kinetics were next measured to determine the affinity of Fabs HER3-3 and HER3-10 to HER3-ECD. Fabs were immobilized on anti-Fab CH1 biosensors and the binding of HER3-ECD to immobilized Fabs was analyzed using bio-layer interferometry. For Fab HER3-3, association and dissociation rate constants were 8.62E+04 (1.00E+03) M-1s-1 and 1.85E-04 (4.10E-06) s-1, respectively. The equilibrium dissociation constant for the interaction was 2.14±0.05 nM (FIG. 6B). For Fab HER3-10, association and dissociation rate constants were 1.02E+05 (9.78E+02) M-1s-1 and 2.55E-04 (3.60E-06) s-1, respectively. The equilibrium dissociation constant for the interaction was 2.49±0.04 nM (FIG. 6C). The presence of Fc-tag in the HER3-ECD construct can give rise to HER3-ECD dimers and can increase the affinity of Fabs HER3-3 and HER3-10. Association and dissociation data sets were fit using both 1:1 and 1:2 binding models, and meaningful KD values were obtained only for the 1:1 model, suggesting that the chances of two sensor-immobilized Fab ligands interacting with the same HER3-ECD-Fc dimer are low under given experimental conditions. To test the specificity of Fabs HER3-3 and HER3-10, the binding of Fabs to epidermal growth factor receptor (EGFR), an ErbB member, closely related to HER3 was assessed. In BLI analysis, both Fabs bound specifically to HER3-ECD with no observable binding to EGFR-ECD (FIG. 6D). To test whether Fab HER3-3 recognized cell-surface HER3, the binding of fluorescently labeled Fab HER3-3 to HER3-overexpressing HEK293T cells using flow cytometry was assayed. Fab HER3-3 showed significant binding to HER3-positive cells relative to unstained or untransfected cells (FIG. 6E).

To further test the ability of Library-S to produce high-affinity Fabs conducted solid-phase selections against four additional antigens (RAD51, FGFR1, FGFR4 and JAG-GED1) were conducted, and several Fab-encoding phagemids were isolated through random clone-picking and Sanger sequencing. The most frequent Fab from each selection were expressed and purified, and the binding affinity of Fabs was determined using bio-layer interferometry. Diversified CDR sequences of Fabs and their KD values are shown in Table 4. Fabs bound strongly to their targets with sub-nM to mid-nM KD values. The highest-affinity Fab bound to JAGGED1 with a KD of 0.5±0.04 nM. These results confirm the potential of Library-S in generating high-affinity Fabs against multiple antigens.

Figure 7:
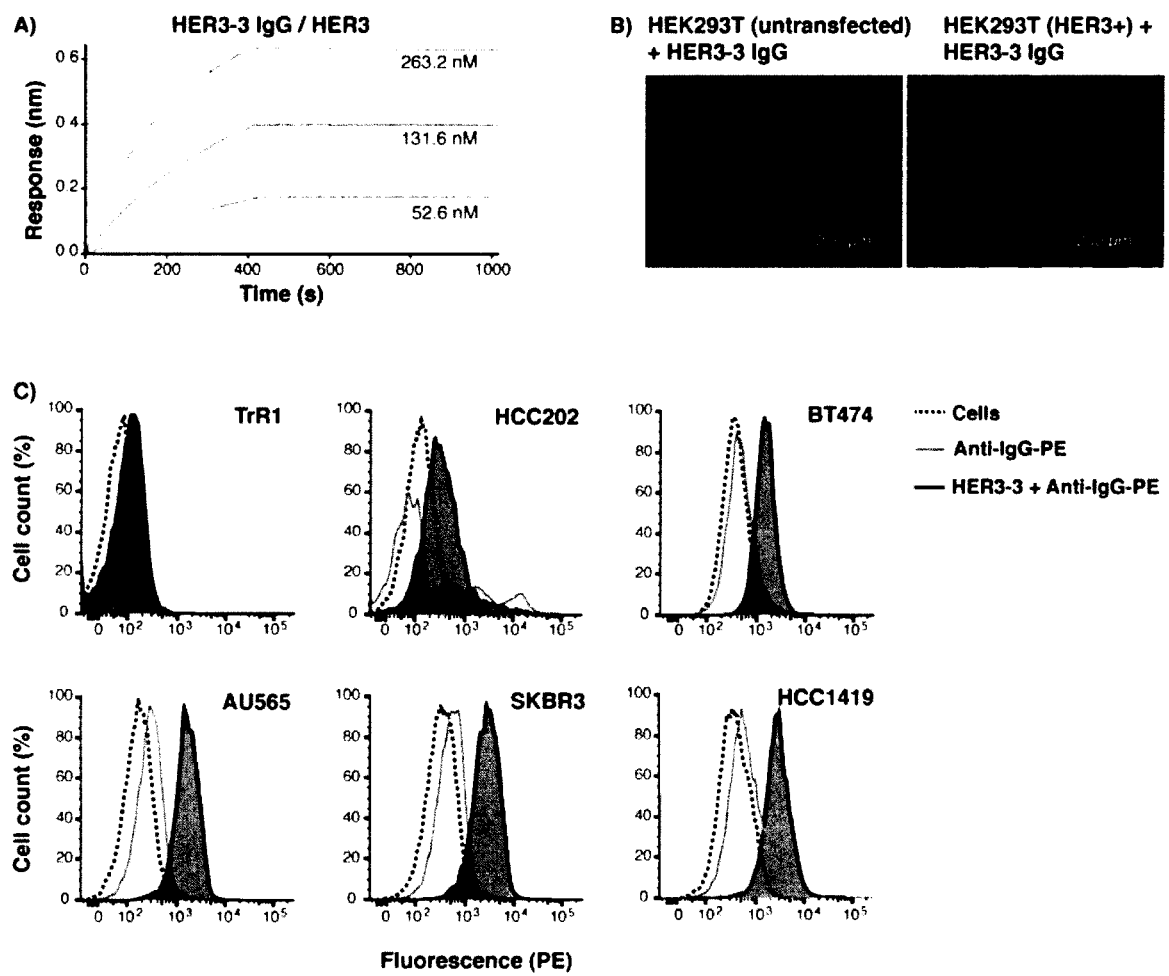

To test whether Library-S Fabs can retain high-affinity binding upon conversion into full-length IgGs, Fab HER3-3 light and heavy chain sequences were subcloned into IgG expression vectors, and expressed and purified HER3-3 IgG from HEK293T cells using Protein-A affinity chromatography. To determine the affinity of HER3-3 IgG to HER3-ECD, HER3-IgG was immobilized on amine reactive generation-2 (ARG-2) biosensors, and assessed the binding of HER3-ECD to immobilized HER3-3 IgG using bio-layer interferometry (FIG. 7A). The association and dissociation rate constants were 1.92E+04 (5.92E+01) M-1s-1 and 8.21E-06 (1.55E-06) s-1, respectively. The equilibrium dissociation constant for the interaction was 0.43±0.08 nM. Next, fluorescence microscopy and flow cytometry was used to assess the binding of HER3-3 IgG to cell-surface HER3.

Indirect immunofluorescence experiments showed that HER3-3 IgG bound strongly to HER3-overexpressing HEK293T cells relative to untransfected HEK293T cells (FIG. 7B). Flow histograms showed that HER3-3 IgG did not bind to trastuzumab-resistant cells (TrR1) and bound weakly to HCC202 cells, suggesting these cell-lines have low or no HER3 expression. Significant staining was observed for BT474, AU565, SKBR3, and HCC1419 cell lines (FIG. 7C).

To test whether HER3-3 IgG has an anti-proliferative effect, we measured the viability of HER3-expressing cells (BT474, AU565, SKBR3 and HCC1419) was measured in the presence and absence of HER-3 IgG or trastuzumab (positive control). While trastuzumab exhibited an anti-proliferative effect, HER3-3 IgG did not inhibit the proliferation of HER3-expressing cells (data not shown). Despite binding to cell surface HER3, HER3-3 IgG did not exhibit an anti-proliferative effect, therefore the potential of HER3-3 as an optical imaging reagent was assessed.

FIG. 18 shows a selection performed for antibodies that bind HER3. The light chain/heavy chain were sequenced from the selection as pairs in the same construct. HER3-3 (CDH-H3-ARTDPYSLGGYYFDY (SEQ ID NO: 58); CDR-L3-QQYGWLPLT (SEQ ID NO: 3) represented the most sequences. However, the heavy chain was also found frequently with QQYSYPLT (SEQ ID NO: 14)>QQYGY-PLT (SEQ ID NO: 13)>QQYSFPLT (SEQ ID NO: 16). In addition, some variations in H3 were observed including ARTDPYSLGGHYFDY (SEQ ID NO: 59), ARTDPYSLG-GYYFDV (SEQ ID NO: 60), and ARTDRHSLGGYYFDY (SEQ ID NO: 61).

TABLE 1

L3 sequences set out on the x-axis of FIG. 18.

| L3 Sequences | SEQ ID NO: |
|---|---|
| QQYGWLPLK | 9 |
| QQYGWLPLT | 10 |
| QQYGWLPPT | 11 |
| QQYAYPLT | 12 |
| QQYGYPLT | 13 |
| QQYSYPLT | 14 |
| QQYGSPLT | 15 |
| QQYSFPLT | 16 |
| QQYTTHPLT | 17 |
| QQAGYRPLT | 18 |

TABLE 2

H3 sequences set out on the y-axis of FIG. 18.

| H3 | SEQ ID NO: |
|---|---|
| ARAPSYSYGSYHYYYYYFDV | 19 |
| ARAPSYSYGSYHYYYYYFDV | 20 |
| ARAPSYSYGSYHYYYYYFDY | 21 |
| ARSPSYSYGSYHYYYYYFDV | 22 |
| ARAPSYHFGVHSFYYYYYFDV | 23 |
| ARSPYAYFGSHHYYYYYFDV | 24 |
| ARSGSYYHYGWHYYYYYFDV | 25 |
| ARSPSYYYGHDYFYYYYYFDV | 26 |
| ARSSPYFYGYSYYYYYFDV | 27 |
| ARAGYYVYGASAYYYYYMDV | 28 |
| ARGGSAWYVSYYYYYFDV | 29 |
| ARAGYASPYYYYYFDY | 30 |
| ARAGYASPYYYYYFDY | 31 |
| ARAGYAPGYYYYYFDY | 32 |

TABLE 2 -continued

H3 sequences set out on the y-axis of FIG. 18.

| H3 | SEQ ID NO: |
|---|---|
| ARAGYASPYYYYYYFDV | 33 |
| ARGGYASPYYYYYYFDV | 34 |
| ARGGYASPYYYYYYFDY | 35 |
| ARAGYYSPYAYYYYFDY | 36 |
| ARGGSHSSYPGYYYYFDY | 37 |
| ARGGSHSSYPGYYYYYYFDY | 38 |
| ARGGYSSYGYYYYFDY | 39 |
| ARGGYSSYGYYYYYFDY | 40 |
| ARGGYSSYPGYYYYYFDY | 41 |
| ARAGHVPGPWGYYYYYFDY | 42 |
| ARYYGYDPSHYYYYYFDY | 43 |
| ARTDPYSLVGYYFDY | 44 |
| ARTDPYSLVYYFDY | 45 |
| ARTDQYSLGGYYFDY | 46 |
| ARTDSYSLGGYYFDY | 47 |
| ARTDPYSLGGYYFGY | 48 |
| ARTDPYSLGGYYFNY | 49 |
| ARADPYSLGGYYFDY | 50 |
| ARTDPYSLGGYYFDY | 51 |
| ARTDPYSLGGHYFDY | 52 |
| ARTDPYSLGGYYFDV | 53 |
| ARTDRHSLGGYYFDY | 54 |
| ARGGYYFDY | 55 |
| ARHGSYAAFDY | 56 |
| ARAPSTLTVLPLLLLLLLRR | 57 |

Fab HER3-3 has the amino acid sequences set out below:

1. Entire light chain (HER3-3_LightChain). CDR sequences are underlined.

(SEQ ID NO: 7)
DIQMTQSPSSLSASVGDRVTIT<u>CRASQGISNYLA</u>WYQQKPGKAPKLLIY

<u>AASSLQS</u>GVPSRFSGSRSGTDFTLTISSLQPEDFATYYC<u>QQYGWLPLT</u>F

GQGTKVEIK

2. Entire Heavy chain (HER3-3_HeavyChain). CDR sequences are underlined.

(SEQ ID NO: 8)
EVQLVESGGGLVQPGGSLRLSCAASGFTFS<u>SY</u>GMHWVRQAPGKGLEWVA

<u>VISYDGSNKYYADSVKG</u>RFTISRDNSKNTLYLQMNSLRAEDTAVYYCAR

<u>TDPYSLGGYYFDY</u>WGQGTLVTVSS

3. Complementarity-determining region one in the light chain as defined by Kabat (HER3-3_CDRL1_L24-34_Kabat)

(SEQ ID NO: 1)
RASQGISNYLA

4. Complementarity-determining region two in the light chain as defined by Kabat (HER3-3_CDRL2_L50-56_Kabat)

(SEQ ID NO: 2)
AASSLQS

5. Complementarity-determining region three in the light chain as defined by Kabat (HER3-3_CDRL3_L89-97_Kabat)

(SEQ ID NO: 3)
QQYGWLPLT

6. Complementarity-determining region one in the heavy chain as defined by Kabat (HER3-30CDRH1_H31-H35B_Kabat)

(SEQ ID NO: 4)
SY

7. Complementarity-determining region two in the heavy chain as defined by Kabat (HER3-3_CDRH2_H50-H65_Kabat)

(SEQ ID NO: 5)
VISYDGSNKYYADSVKG

8. Complementarity-determining region three in the heavy chain as defined by Kabat (HER3-3 CDRH3_H95-H102_Kabat)

(SEQ ID NO: 6)
TDPYSLGGYYFDY

Table 8 provides the Fab HER3-3 CDR sequences as defined by IGMT numbering.

Figure 8:
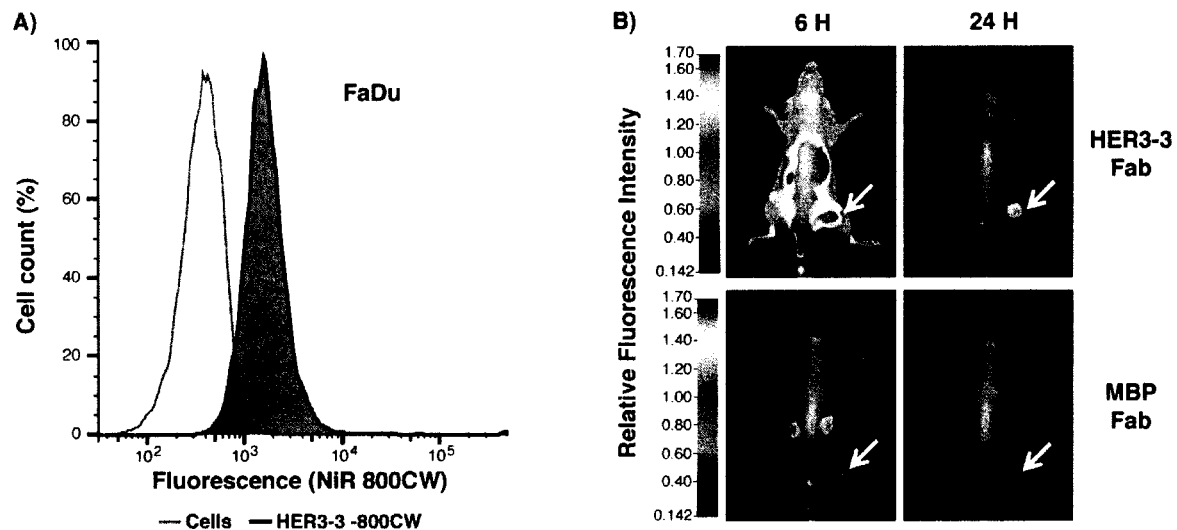

Near infrared (NIR) in vivo imaging was performed using CD-1 athymic nude mice bearing FaDu cell line xenografts. The FaDu cell line was used since it engrafts well in immunocompromised mice and expresses HER3 (Mirschberger et al., 2013). The HER3-3 Fab and a control Fab targeting the unrelated protein, maltose binding protein (anti-MBP), were conjugated to the NIR dye IRDye800CW. Binding of the HER3-3 Fab-IRDye800CW construct to FaDu cells was analyzed by flow cytometry (FIG. 8A). A significant shift in fluorescence was observed following HER3-3 Fab-IRDye800CW addition, which agrees with previous reports indicating that the FaDu cell line expresses HER3 (Terwisscha Van Scheltinga et al., 2014). Posterior whole body images of FaDu-xenografted mice were acquired at 6-h and 24-h post injection of 0.5 nmole of either HER3-3 Fab-IRDye800CW or a control antibody (anti-MBP Fab-IRDye8000W) (FIG. 8B). NIR Imaging showed that HER3-3 Fab-IRDye800CW accumulated at the FaDu xenograft, resulting in higher fluorescence intensity in the xenograft compared to the contralateral side, lacking a xenograft at both time points. The control anti-MBP Fab- IRDye800CW showed a very slight accumulation at 6-h and no accumulation 24-h post injection, consistent with non-specific tumor uptake. This indicated the selective binding of HER3-3 Fab-IRDye800CW to xenografts expressing HER3 in vivo. Images taken at 6-h post injection also show fluorescence in the kidneys for both Fabs. This is consistent with previous reports that the Fabs are preferentially catabolized and excreted through the kidneys (Tang et al., 2005 and Covell et al, 1986) The relatively high tumor to background signal of HER3-3 Fab-IRDye800CW, particularly at 24-h time point, suggests that Fab HER3-3 may be useful as an imaging reagent to detect HER3-positive tumors. Previous studies have shown that Fabs are preferred over IgGs for imaging tumors within 24-h post injection (Goldenburg et al., 1990).

Methods

Library-S Construction

To create the template phagemid for library-S construction, the pHP153 phagemid encoding the anti-maltose binding protein Fab as the starting phagemid was used (Persson et al., 2013). Desired mutations were incorporated into the Hu4D5-8 Fab framework and CDRs by oligonucleotide-directed mutagenesis as described previously (Kunkel et al., 1987). In the first round of mutagenesis, five oligonucleotides were used to incorporate mutations into the following regions: CDRL1, CDRL2, CDRH1, CDRH2 and FRM3. In the second round of mutagenesis, two oligonucleotides were used to incorporate NotI restriction sites into CDRL3 and CDRH3. The resulting phagemid was sequence verified and used as the template phagemid for library-S mutagenesis. The variable light and heavy chain sequences of the library-S phagemid are included in FIG. 1. Library-S was constructed and stored, using previously established protocols (Fellouse and Sidhu, 2006; Rajan and Sidhu, 2012). Briefly, Kunkel mutagenesis was used to replace the NotI sites and replace CDRL3 and CDRH3 positions with fixed or degenerate codons encoding the amino acid composition shown in FIG. 3. Custom-designed mutagenic oligonucleotides synthesized from trinucleotide phosphoramidites purchased from Tri-Link Biotechnologies (Table 3). DNA from the mutagenesis reaction was electroporated into SR320 (Lytic phage resistant clone from SS320, Gift from Sidhu lab). Double-stranded phagemid DNA library was extracted from SR320 *E. Coli* cells and digested with NotI to remove unmutated template DNA. Purified library DNA was electroporated into M13KO7-infected SR320 *E. coli* cells for phage production. Phages were purified from the culture supernatant, resuspended in PBS and stored at −80° C. in the presence of protease inhibitors (2%) and sterile glycerol (25%). Twenty different Kunkel mutagenesis reactions were required for Library-S construction with each reaction representing a specific CDRH3 length. Phages from twenty sub-libraries were recovered separately and equal number of phages from each sub-library were mixed together to create the Library-S.

TABLE 3

Table of synthetic oligonucleotides used for library-S diversification

|  |  | SEQ ID NO: |
|---|---|---|
| L3-09 | TTCGCAACTTATTACTGTCAGCAAZZZZCCTCTGACGTTCGGACAGGGTACC | 62 |
| H3-JH4-07 | CCGTCTATTATTGTGCTCGCZBTTCGACTACTGGGGTCAAGGAAC | 63 |
| H3-JH4-08 | CCGTCTATTATTGTGCTCGCZZBTTCGACTACTGGGGTCAAGGAAC | 64 |
| H3-JH4-09 | CCGTCTATTATTGTGCTCGCZZZBTTCGACTACTGGGGTCAAGGAAC | 65 |
| H3-JH4-10 | CCGTCTATTATTGTGCTCGCZZZZBTTCGACTACTGGGGTCAAGGAAC | 66 |
| H3-JH4-11 | CCGTCTATTATTGTGCTCGCZZZZZBTTCGACTACTGGGGTCAAGGAAC | 67 |
| H3-JH4-12 | CCGTCTATTATTGTGCTCGCZZZZZZBTTCGACTACTGGGGTCAAGGAAC | 68 |
| H3-JH4-13 | CCGTCTATTATTGTGCTCGCZZZZZZZBTTCGACTACTGGGGTCAAGGAAC | 69 |
| H3-JH4-14 | CCGTCTATTATTGTGCTCGCZZZZZZZZBTTCGACTACTGGGGTCAAGGAAC | 70 |
| H3-JH4-15 | CCGTCTATTATTGTGCTCGCZZZZZZZZZBTTCGACTACTGGGGTCAAGGAAC | 71 |
| H3-JH4-16 | CCGTCTATTATTGTGCTCGCZZZZZZZZZZBTTCGACTACTGGGGTCAAGGAAC | 72 |
| H3-JH6-16 | CCGTCTATTATTGTGCTCGCXXXXXXXXTACTACTACTACTTTGACTACTGGGGTCAAGGAACCCT | 73 |
| H3-JH6-17 | CCGTCTATTATTGTGCTCGCXXXXXXXXXTACTACTACJOGACUTGGGGTCAAGGAACCCT | 74 |

TABLE 3 -continued

Table of synthetic oligonucleotides used for library-S diversification

| | | SEQ ID NO: |
|---|---|---|
| H3-JH6-18 | CCGTCTATTATTGTGCTCGCXXXXXXXXXXTACTACTACJOGACUTGGG GTCAAGGAACCCT | 75 |
| H3-JH6-19 | CCGTCTATTATTGTGCTCGCXXXXXXXXXXTACTACTACTACJOGACUTG GGGTCAAGGAACCCT | 76 |
| H3-JH6-20 | CCGTCTATTATTGTGCTCGCXXXXXXXXXXTACTACTACTACJOGACGT TTGGGGTCAAGGAACCCT | 77 |
| H3-JH6-21 | CCGTCTATTATTGTGCTCGCXXXXXXXXXXXTACTACTACTACJOGACG TTTGGGGTCAAGGAACCCT | 78 |
| H3-JH6-22 | CCGTCTATTATTGTGCTCGCXXXXXXXXXXXXTACTACTACTACJOGAC GTTTGGGGTCAAGGAACCCT | 79 |
| H3-JH6-23 | CCGTCTATTATTGTGCTCGCXXXXXXXXXXXXXTACTACTACTACGGAO GACGTTTGGGGTCAAGGAACCCT | 80 |
| H3-JH6-24 | CCGTCTATTATTGTGCTCGCXXXXXXXXXXXXXXTACTACTACTACGGA OGACGTTTGGGGTCAAGGAACCCT | 81 |
| H3-JH6-25 | CCGTCTATTATTGTGCTCGCXXXXXXXXXXXXXXXTACTACTACTACGG AATGGACGTTTGGGGTCAAGGAACCCT | 82 |

Codon Z denotes any of the following thirteen amino acids introduced at different proportions: Y (20%), S (20%), G (20%), T (6.5%), A (6.5%), P (6.5%), H (3.5%), R (3.5%), E (3.5%), F (2.5%), W (2.5%), V (2.5%) or L (2.5%). Codon X denotes any of the following nine amino acids introduced at different proportions: Y (25%), S (20%), G (20%), A (10%), F (5%), W (5%), H (5%), P (5%) or V (5%). Codon B encodes for four amino acids A, G, D or Y at 25% each. Codon J encodes for two amino acids G or Y at 50% each. Codon U encodes for two amino acids V or Y at 50% each. Codon O encodes for two amino acids M or F at 50% each.

Phage Display Selections

The recombinant Fc-tag-fused human HER3 ectodomain (HER3-ECD) fused to Fc was purchased from Sino Biological Inc. Solid-phase panning of Library-S was conducted against HER3-ECD according to previously described protocols (Fellouse and Sidhu, 2006; Rajan and Sidhu, 2012). Briefly, phages from the frozen master library were precipitated, deselected for binding to the Fc protein and cycled through rounds of binding selection with HER3-ECD coated on 96-well Maxisorp plates and amplification of HER3-ECD-bound phage in XL1-Blue E. coli cells. After four rounds of selections, phage clones were plated as individual colonies for isolation, sequencing, and manipulation of phagemid DNA.

Ion Torrent Sequencing and Data Analysis

Ion Torrent sequencing of the diversified CDR regions was accomplished in three steps: PCR amplification of CDR, emulsion PCR on Ion sphere particles (ISPs) and sequencing enriched ISPs on an Ion semiconductor chip. To PCR amplify CDRs from phage pools; primers that hybridize to the fixed framework regions of the phagemid that flank the CDR region were designed. Primers contain barcodes for multiplexing purposes and adapter sequences to facilitate emulsion PCR. The CDR of interest was PCR-amplified from phage samples, the purity, concentration and length of PCR products were checked using a 2100 bio-analyzer (Agilent Technologies), the template for emulsion PCR was prepared by pooling multiple PCR products, emulsion amplification of the amplicon library was performed on the Ion OneTouch 2 instrument (Life Technologies), the enriched ISPs were loaded into an Ion 314 Semiconductor chip, and the loaded ISPs were sequenced on the V2 Ion Personal Genome Machine (Thermo Scientific), according to manufacturer's instructions. A custom workflow was built for NGS data processing and analysis. Sequences were base called and separated by barcode on the Ion PGM Torrent Server and exported in FASTQ format. Sequences were imported into the Galaxy server, where they were trimmed based on quality score (>17), converted to FASTA and then run on a custom R script (R Core Team, 2013), to parse the CDR, translate, and perform sequence counts. The RGalaxy package was used to run the function on Galaxy, the Biostrings package was used to process the sequences, plots were generated using the ggplot2 package, and sequence logos were generated with the RWebLogo package, using the WebLogo program.

Fab Expression and Purification

Fabs HER3-3 and HER3-10 was sub-cloned from the phagemid into the pCW-LIC Fab expression vector (Addgene) using standard molecular biology procedures. Briefly, Fab sequences were amplified from phagemids by PCR, and ligated into the SacI/XhoI-digested pCW-LIC vector using Gibson assembly. Fab expression plasmids were sequence verified and electroporated into BL21 E. coli cells. Transformed E. coli cells were grown to mid-log phase in 2YT media supplemented with 100 μg/mL carbenicillin. For expressing Fabs, 4 mL of the starter culture was transferred into 400 mL of Overnight Express Instant TB auto-induction media (EMD Millipore) supplemented with 100 μg/mL carbenicillin and incubated for 16 hours at 25° C. Cells were pelleted by centrifugation and lysed in Protein-L binding buffer (20 mM $Na_2HPO_4$, 0.15 M NaCl, pH 8) containing 1:100 dilution of protease inhibitor cocktail (sigma) using a cell disruptor (Constant Systems). Clarified supernatant was loaded into a Protein-L column (GE healthcare) and washed with 10 column volumes of Protein-L binding buffer (AKTA prime plus). Fabs were eluted with IgG elution buffer (Thermo-Scientific) and neutralized with 1M Tris-HCl (pH 9). Eluted Fabs were dialyzed against PBS and stored at −20° C. Fab purity was verified using 2100 bio-analyzer (Agilent Technologies) and Fab concentration was determined by UV-visible spectrometry.

Biolayer Interferometry (BLI)

To measure the equilibrium dissociation constants of Fabs and IgGs, the ForteBio Octet Red384 BLI system was used (Pall Corporation). Fabs were immobilized on anti-Fab-CH1 biosensors, and IgGs were immobilized on amine-reactive generation-2 (ARG2) biosensors according to manufacturer's instructions. Immobilized antibodies were exposed to increasing concentrations of HER3-ECD-Fc, and association and dissociation rates were measured by the shift in wavelength (nm). All reactions were performed at 25° C. in PBS. Data was collected with Octet Data Acquisition version 7,1.0.87 (ForteBio), and globally fit to 1:1 binding model using Octet Data Analysis version 7.1 (ForteBio).

Labelling with IRDye800CW

HER3-3 and anti-MBP Fabs were labeled using IRDye 8000W-NHS (LI-COR Biosciences, Lincoln, Nebr.) following the manufacturer's instructions. Fabs in PBS, pH 7.4 were mixed with 5-fold molar excess of IRDye 8000W-NHS in DMSO and allowed to react for 2 h at 20° C. followed by overnight incubation at 4° C. protected from light. Excess unbound dye was removed using 5 mL Zeba Spin Desalting Columns, 5 mL, 7K MWCO (Thermo Scientific, Catalog number 89892). The dye to protein ratio was determined by measuring the absorbance of labeled Fabs in PBS at 280 and 789 by UV visible spectrometry as per the manufacturer's recommendation and as reported previously. Samples were sterilized by filtration and stored protected from light at 4° C. for short-term storage or at −80° C. for long-term storage.

Cell Lines

All cell lines were purchased from the American Type Culture Collection (ATCC, Manassas, Va.). The human hypopharyngeal squamous cell carcinoma FaDu cell line (ATCC #HTB-43) over-expressing HER3 were propagated by serial passage in MEM/EBSS medium (HyClone Laboratories, Logan Utah), supplemented with 10% fetal bovine serum (FBS). HEK 293T cells were grown in DMEM (Sigma) with 10% FBS. Human breast tumor cell lines, BT-474, and SK-BR3 were grown in DMEM supplemented with 10% FBS; while HCC202, HCC1419, and AU565 cell lines were cultured in RPMI 1640 with 10% FBS and 1% PSG. Trastuzumab-resistant cell-line (TrR1) derived from MDA-MB-231 stably expressing HER2 (duManoir et al., 2006). All cells were maintained at 37° C. in a humidified atmosphere of 5% C02. HEK 293T cells were transiently transfected with plasmid pCMV-SPORT6-ERBB3 (OpenBiosystems, MHS1010-98051190) to express HER3 using polyethylenimine as described previously (Dahabieh et al., 2014).

IgG Expression and Purification

HER3-3 was subcloned into pFUSEss-CHIg-hG1 and pFUSEss-CLIg-hK (Invivogen) following manufacturer's instructions. HER3-3 IgG was expressed using Expi293F Expression System Kit (Life Technologies) following manufacturer's protocol. Briefly, DNA and ExpiFectamine™ 293 reagent were incubated separately for 5 min in Opti-MEM I. Then combined and incubated for an additional 20 minutes at room temperature. The complexed DNA was then added to Expi293™ cells at $2.9 \times 10^6$ cells/mL in Expi293 Expression Medium. After 20 hours ExpiFectamine™ 293 Enhancer 1 and 2 were added to each flask and incubated for an additional 4 days. The supernatant was collected and purified on a MabSelect Protein A column (GE healthcare), and eluted in IgG elution buffer (Thermo-Scientific) and immediately neutralized with 1M Tris-HCl (pH 9). Eluted IgG was dialyzed against PBS and stored at −80° C. Purity and MW were determined using a Bioanalyzer 2100 (Agilent) with a high sensitivity protein chip (5067-1575, Agilent). Concentration was determined by UV with MW (150,554 Da) and extinction coefficient (224,320 $M^{-1}$ $cm^{-1}$) calculated using ProtParam (Expasy).

Flow Cytometry and Immunofluorescence

Flow cytometry was used to assess the binding of fluorescently-labeled Fab HER3-3 to HER3-expressing HEK293T cells and FaDu cells. Cells were split into equal fractions (~2×105 cells) and incubated with 50-100 pmoles of 800CW labeled Fab HER3-3 and incubated for 60 min in dark at RT. Cells were washed three times with ice cold PBS (pH 7.4), and analyzed using a Gallios flow cytometer (Beckman Coulter, Inc.) on the FL8 channel (excitation: 640 nm and emission 745-825 nm), resulting in a weak but measurable shift for binding. A minimum of 10,000 viable cell events was acquired for each experiment. Flow cytometry data were analyzed using FlowJo software, V10.1 (FlowJo, LLC). IgG flow cytometry was performed as above, except, the cells were washed and suspended in a 1:50 dilution of FITC labelled Goat F(ab')2 fragment anti-human IgG (H+L) antibody (Beckman Coulter) and incubated for 30 minutes on ice. Cells were washed and suspended in 1×PBS+2% FBS and analyzed using a Gallios flow cytometer (Beckman Coulter) on the FL1 channel (excitation: 488 nm and emission: 505-545 nm). For Immunohistochemistry, HER3-3 IgG-stained HEK293T cells were imaged on a digital inverted fluorescent microscope (EVOS).

In Vivo Animal Imaging

All animals used in imaging experiments were cared for and maintained under the supervision and guidelines of the University of Saskatchewan Animal Care Committee. Female CD-1 nude mice were obtained from Charles River Canada (St-Constant, Quebec, Canada) at 4 weeks of age and housed in a 12 h light, 12 h dark cycle in a temperature and humidity controlled vivarium. Animals had ad libitum access to mouse diet (Lab Diet, St. Louis, Mo.) and water. After one week of acclimatization, mice were subcutaneously injected with a suspension of $5 \times 10^6$ FaDu cells in 100 μL of a 1:1 mixture of serum-free MEM/EBSS medium (HyClone Laboratories, Logan, Utah) and Matrigel matrix basement membrane (Discovery Laboware, Inc. Bedford, Mass.) at the hind limb of each mouse. Tumor growth was followed with caliper measurements. 0.5 nmole of each labeled Fab fragment was injected intravenously through the mouse tail vein (3 mice per group) when xenografts measured 150-300 mm³ in volume. Mice were anesthetized with 2.5% isoflurane and imaged at different time points using the Pearl Impulse Imager (LI-COR). Excitation/emission settings for the 800 nm channel were 785/820 nm. The anti-maltose-binding protein (MBP) Fab labeled with 800CW-NHS served as non-specific binding.

TABLE 4

Diversified CDR sequences and KD values of Fabs

| Target | CDRL3 | SEQ ID NO: | CDRH3 | SEQ ID NO: | $K_D$ (nM) |
|---|---|---|---|---|---|
| RAD51 | QQGTYLPLT | 93 | ARTYSYAS RGWYFDY | 94 | 8.1 +/- 0.2 |
| FGFR1 | QQSYRSPLT | 95 | ARSGRYGT YKGDFDY | 96 | 22.4 +/- 1.6 |
| FGFR2 | QQSGSSPLT | 97 | ARSHSYVY TAGYFDY | 98 | 6.5 +/- 0.4 |
| JAGGED1 | QQSLATPLT | 99 | ARSEYGTA GYFDY | 100 | 0.5 +/- 0.04 |

Human RAD51 protein was expressed and purified from E. coli. Full-length extracellular regions of human FGFR1 and FGFR4 were obtained from Sino Biological Inc. Full-length extracellular region of human JAGGED1 was obtained from R&D Systems. Four rounds of solid-phase selections were performed against protein targets, and phagemid harboring Fab sequences were isolated by random clone picking and Sanger sequencing. Phage-ELISA positive Fab clones were sub-cloned into the pCW-LIC Fab expression vector and Fabs were purified using Protein-L affinity chromatography. KD values for protein targets binding to sensor-immobilized Fabs were measured using bio-layer interferometry. Diversified CDR residues are underlined.

Discussion

Synthetic antibody technology has been successful in generating antibodies against a wide variety of antigens with desirable biophysical, biochemical and pharmacological properties (Ponsell et al. 2011). As of July 2016, 13 synthetic antibody-based drugs (12 IgGs and one IgG-drug conjugate) have been undergoing phase II clinical studies and three synthetic antibodies (IgGs) have been undergoing phase III clinical studies. These 16 synthetic antibodies were derived from phage displayed synthetic Fab or scFv libraries (Frenzel et al., 2016).

Given that synthetic antibody libraries are increasingly used to generate novel leads for developing antibody-based therapeutics, a new phage-displayed single-framework synthetic Fab library was designed and constructed, named library-S. The library was built on a modified Hu4D5 framework that contained three point mutations in the FRM3 region to accommodate the new CDRH2 loop. Four CDRs were fixed to preserve the most-frequent canonical CDR conformation preferred by the chosen Fab framework, improving library quality by eliminating CDR sequences that would not result in functional Fabs.

Library diversity, biased towards human antibody CDR sequences, was focused at CDRs L3 and H3, allowing better sequence coverage during selections. Length, amino acid, and conformational diversities were engineered within CDRL3 and CDRH3 using custom-designed tri-nucleotide mixes.

Library-S was constructed using an established M13 phagemid system that displays Fabs in a bivalent format (Lee et al., 2004b). During CDR diversification, template retention was reduced to <1% by restriction enzyme digestion of the phagemid library. The quality of the phage library was assessed in terms of overall sequence composition, length, and amino acid distributions. The library contained ~7.6 billion unique Fabs and >95% of the library correctly encoded both the diversified CDR sequences. Library-S function was validated by generating HER3 binders with high affinity and specificity. Library-S was also used to produce Fabs against four additional antigens with a range of KD values, providing more evidence in support of Library-S design and function.

In recent years, several NGS platforms have been used successfully to analyze antibody libraries and selection output. In this work, Ion Torrent sequencing was used to interrogate the CDR diversity in Library-S and the HER3 phage selection output. This NGS information can be useful for identification and reconstruction of diverse HER3 binders from the selection output. Here, two HER3 Fabs were selected and isolated from the HER3 selection output. The most abundant clone, Fab HER3-3, had a CDRH3 with 15 amino acids and a JH4 gene segment. The second most frequent clone, Fab HER3-10, had a long CDRH3 with 21 amino acids and a JH6 gene segment. While JH segment diversity is typically not seen in single-framework synthetic Fab libraries, incorporated two JH segments were incorporated in Library-S and isolated both JH4- and JH6-containing Fabs against HER3. The use of different JH segments based on CDRH3 lengths could decrease the proportion of nonfunctional CDRH3 sequences and could increase the conformational diversity in CDRH3.

During binding kinetic analysis, Fabs HER3-3 and HER3-10 bound to HER3-ECD with KD values of 2.14 nM and 2.49 nM, respectively. Despite possessing very similar KD values, HER3-10 was ~5-fold less frequent than HER3-3 in the round-4 phage selection output. This could have resulted from the underrepresentation of JH6-containing CDRH3 sequences in Library-S. HER3-3 IgG bound to HER3-ECD with a KD value of 0.43 nM, confirming that Library-S Fabs can retain high-affinity binding upon conversion into full-length IgGs. The association rate of HER3-3 IgG was slower than HER3-3 Fab. The addition of Fc domain could have influenced the association rate of IgG its target (Sela-Culang et al., 2013). The dissociation rate of HER3-3 IgG was 10-fold slower than HER3-3 Fab, likely resulting from the bivalent nature of IgG (Mackenzie et al., 1996). Overall, HER3-3 IgG bound ~5-fold tighter than Fab HER3-3. Fabs containing surface-exposed aromatic residues in their CDRs could bind to off-targets in a non-specific manner. In this work, Fabs HER3-3 and HER3-10 did not interact with EGFR-ECD, an ErbB receptor closely-related to HER3, highlighting the specificity of anti-HER3 binders isolated from Library-S.

Further, HER3-3 Fab and IgG bound significantly to HER3-expressing HEK293T cells relative to untransfected HEK293T cells. Despite binding to cell-surface HER3, HER3-3 IgG did not exhibit an anti-proliferative effect on HER3-expressing cells, therefore the potential of HER3-3 as an optical imaging reagent was assessed. Near Infrared (NIR) imaging showed that Fab-HER3-3-IRDye8000W selectively accumulated to HER3-positive xenografts in a mouse model. Given that antibody fragments (Wu 2014) and peptides (Abbineni, 2010) are increasingly used in diagnostic imaging, and that HER-3 is an attractive target for developing diagnostic probes (Ma 2014 and Zhang 2015), Fab HER3-3 can serve as a lead fragment for developing HER3-targeted optical imaging and nuclear imaging products.

Example 2

Imaging of Various Anti-HER3 Antibody Fragments

Anti-HER3 antibody fragments were expressed in bacteria (FIG. 10A) and mammalian cells (FIG. 10B).

Anti-HER3 fragments were characterized using Bioanalyzer under reducing conditions (FIG. 11A). Anti-HER3 fscFv-$C_H3$ fragments were characterized using Bioanalyzer under reducing vs. non-reducing conditions (FIG. 11B).

Figure 12:
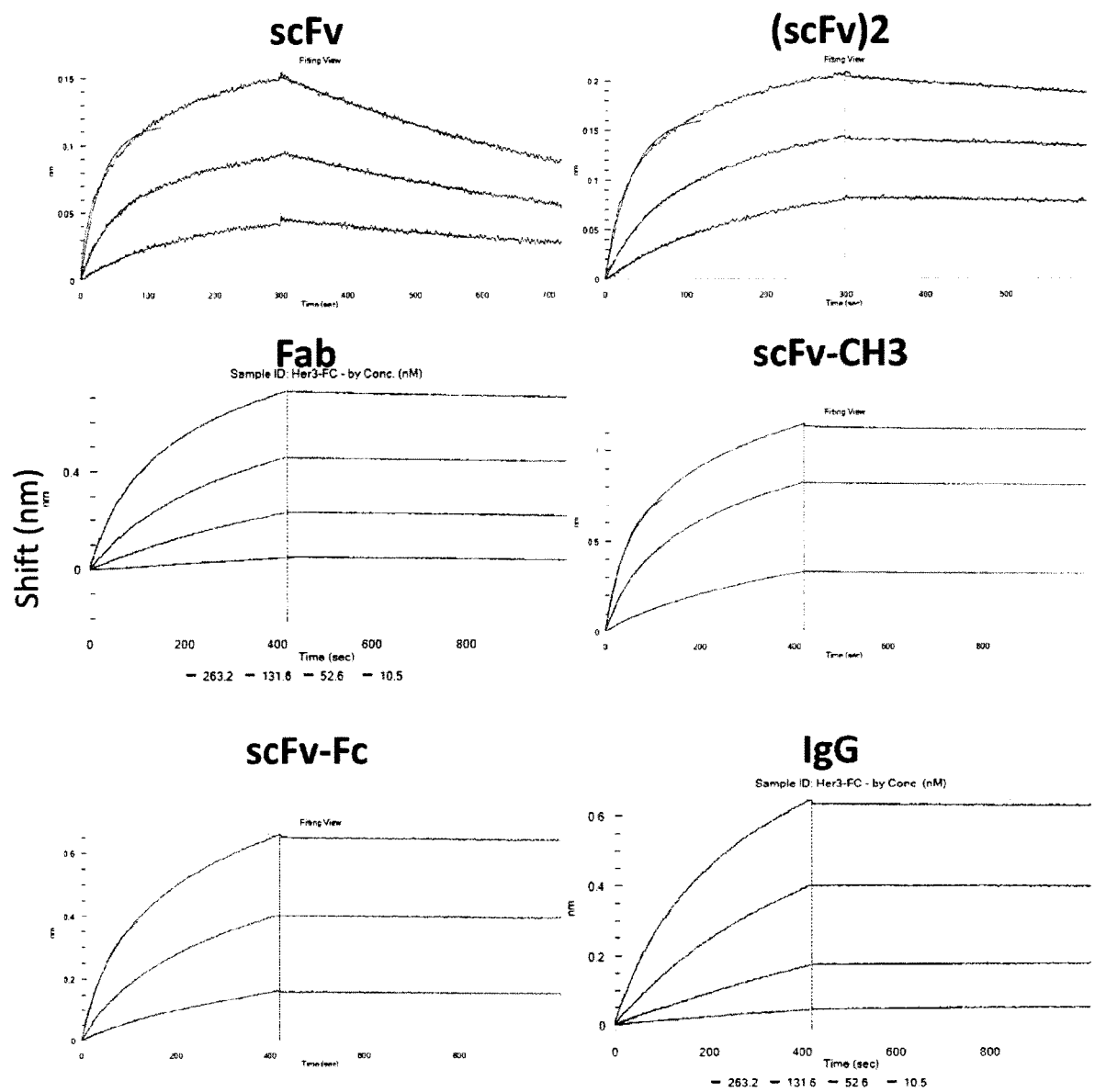
FIG. 12 shows the association and dissociation of anti-HER3 fragments as shown by bio-layer interferometry.

Anti-HER3 fragments association to HER3 and dissociation were shown by bio-layer interferometry (FIG. 12).

Table 5 shows ANTI-HER3 fragments affinity constants by biolayer interferometry.

Figure 13:
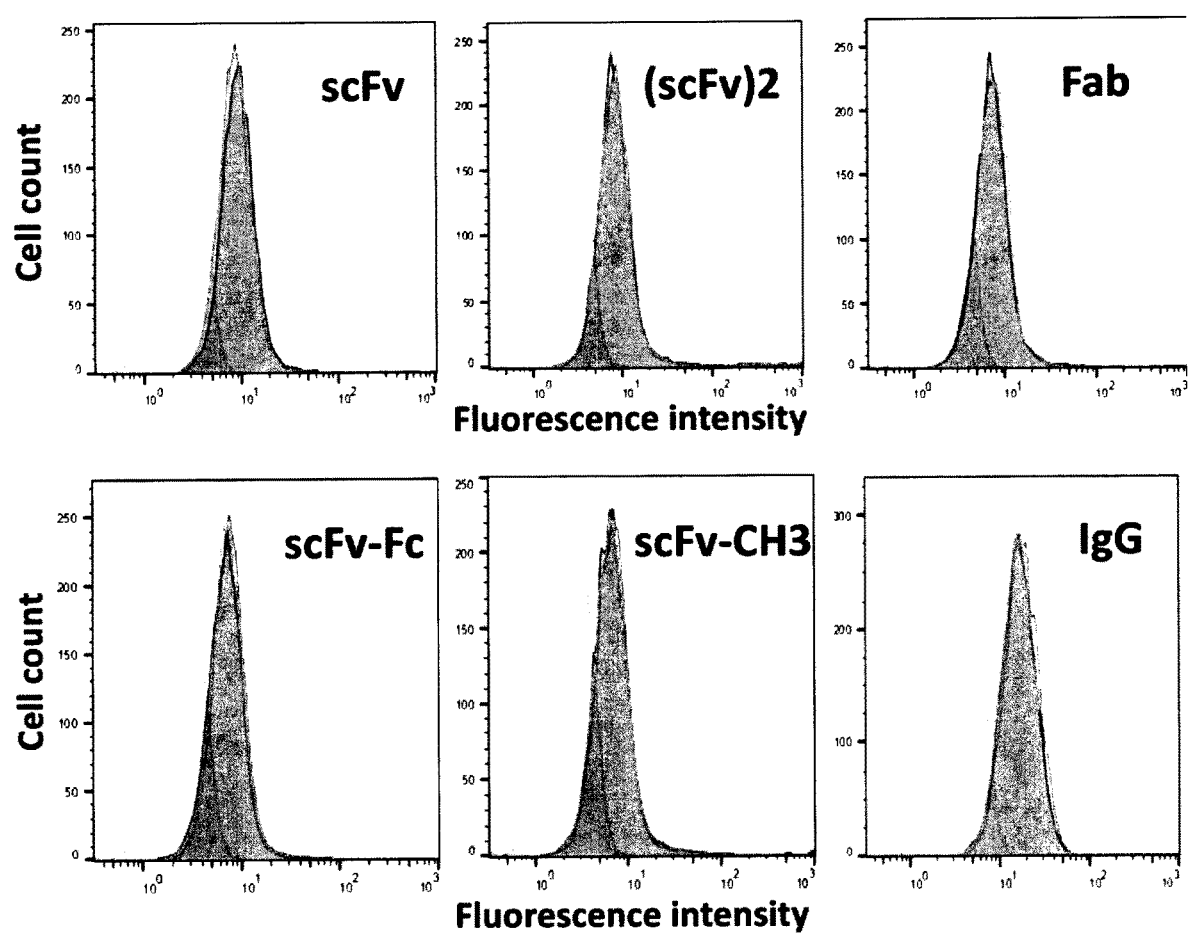
FIG. 13 shows anti-HER3 fragment flow cytometry on FaDu cells.

Flow cytometry was performed on anti-HER3 binding to FaDu (HER3+ expressing) cells (FIG. 13).

Figure 14:
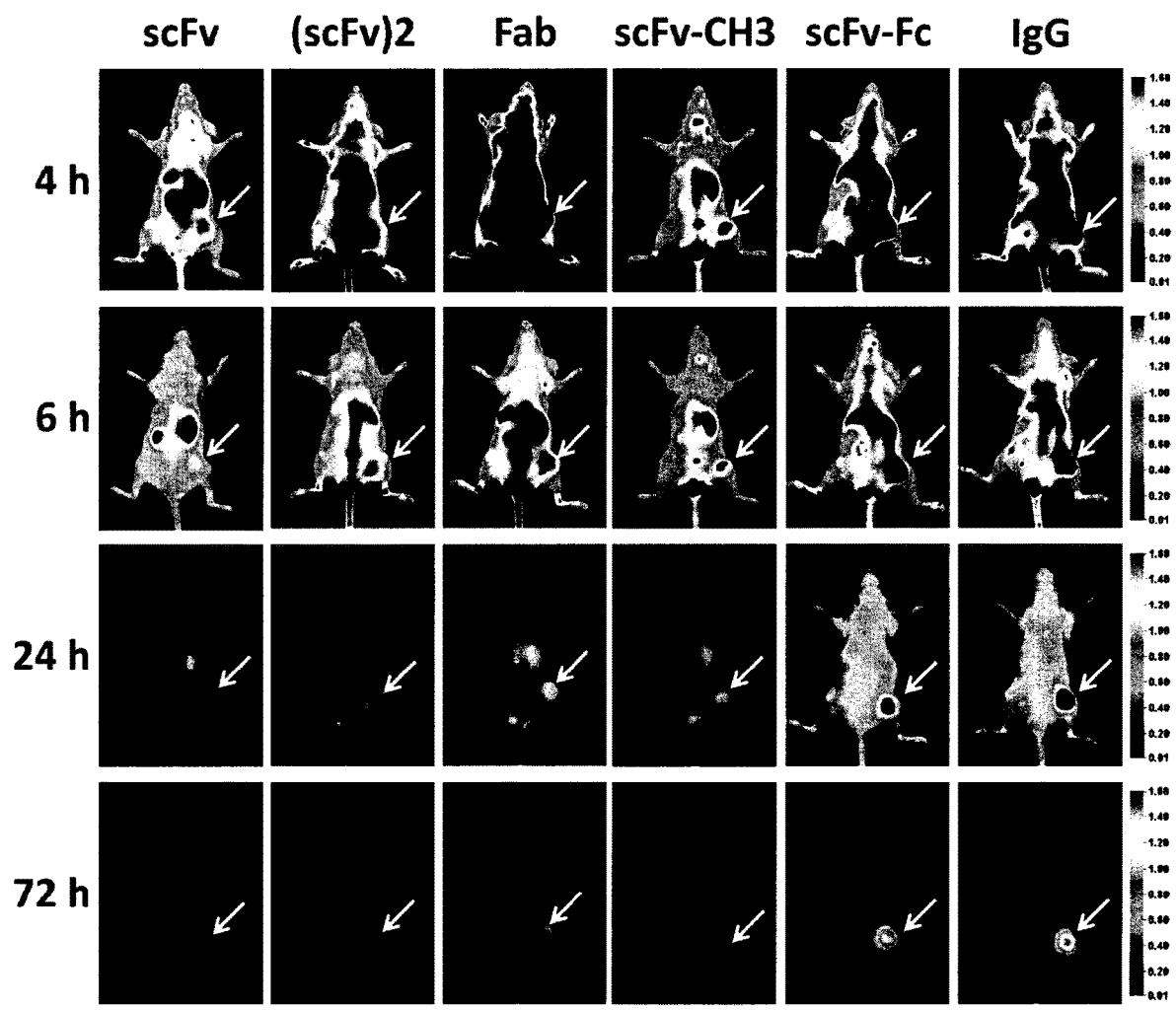
FIG. 14 shows anti-HER3 fragment imaging.
Figure 16:
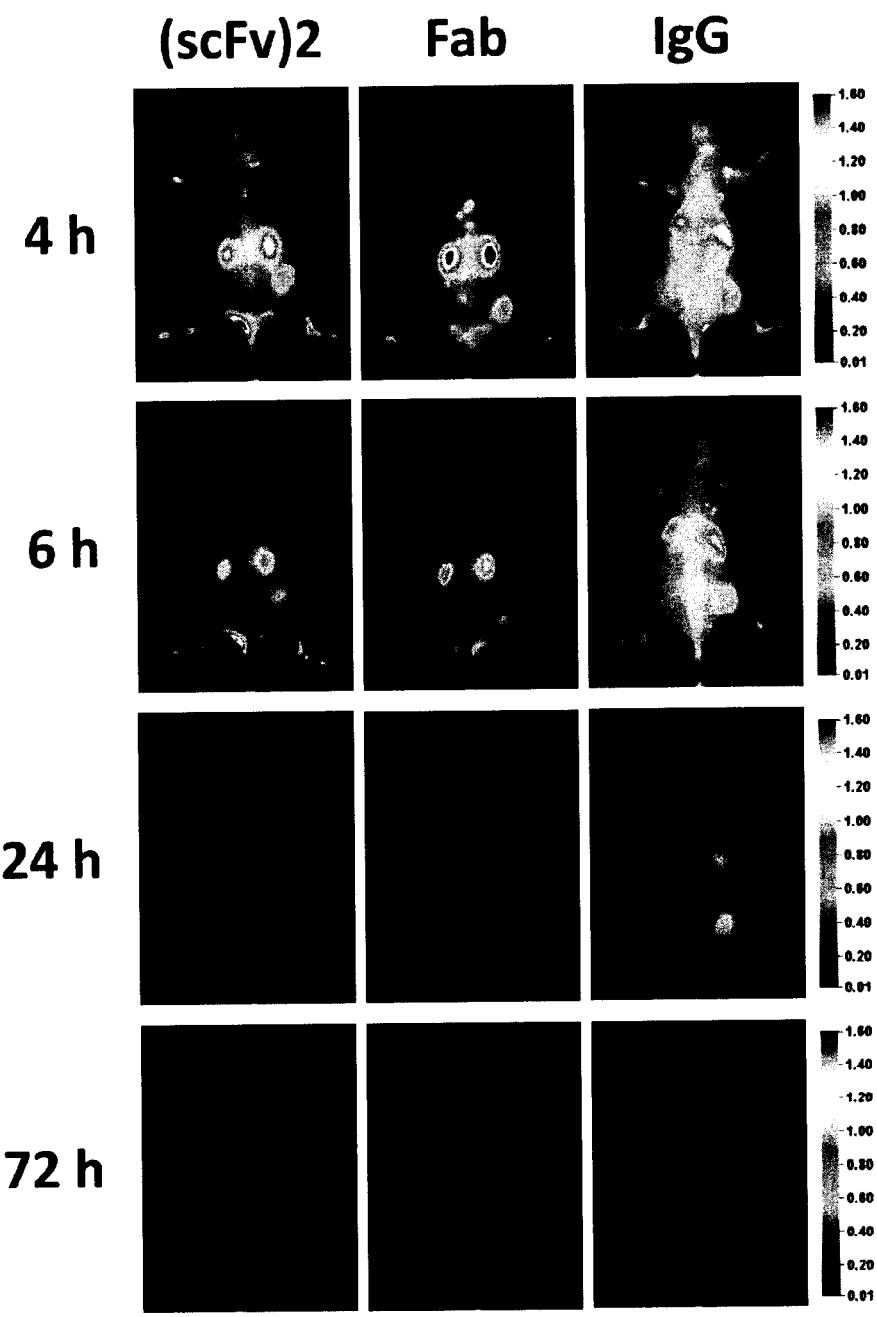
FIG. 16 shows control anti-MBP fragment imaging.

Mice expressing various anti-HER3 fragments were imaged (FIG. 14). Control anti-MBP fragment imaging is shown in FIG. 16.

Figure 15:
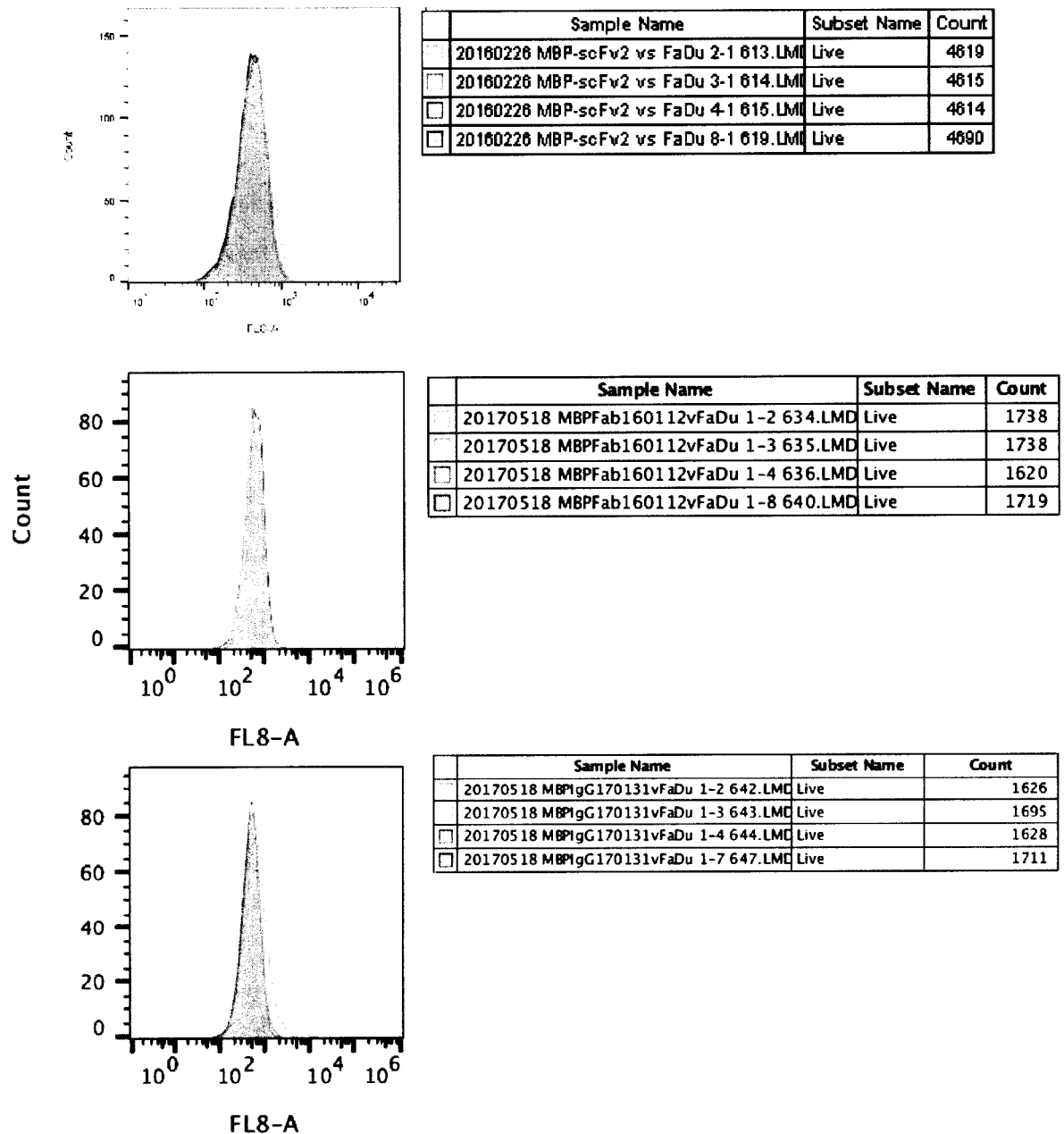
FIG. 15 shows anti-MBP (scFv)2, Fab and IgG binding to FaDu cells by flow cytometry.

Flow cytometry was performed on anti-MBP (scFv)2, Fab and IgG binding to FaDu cells (FIG. 15).

Figure 17:
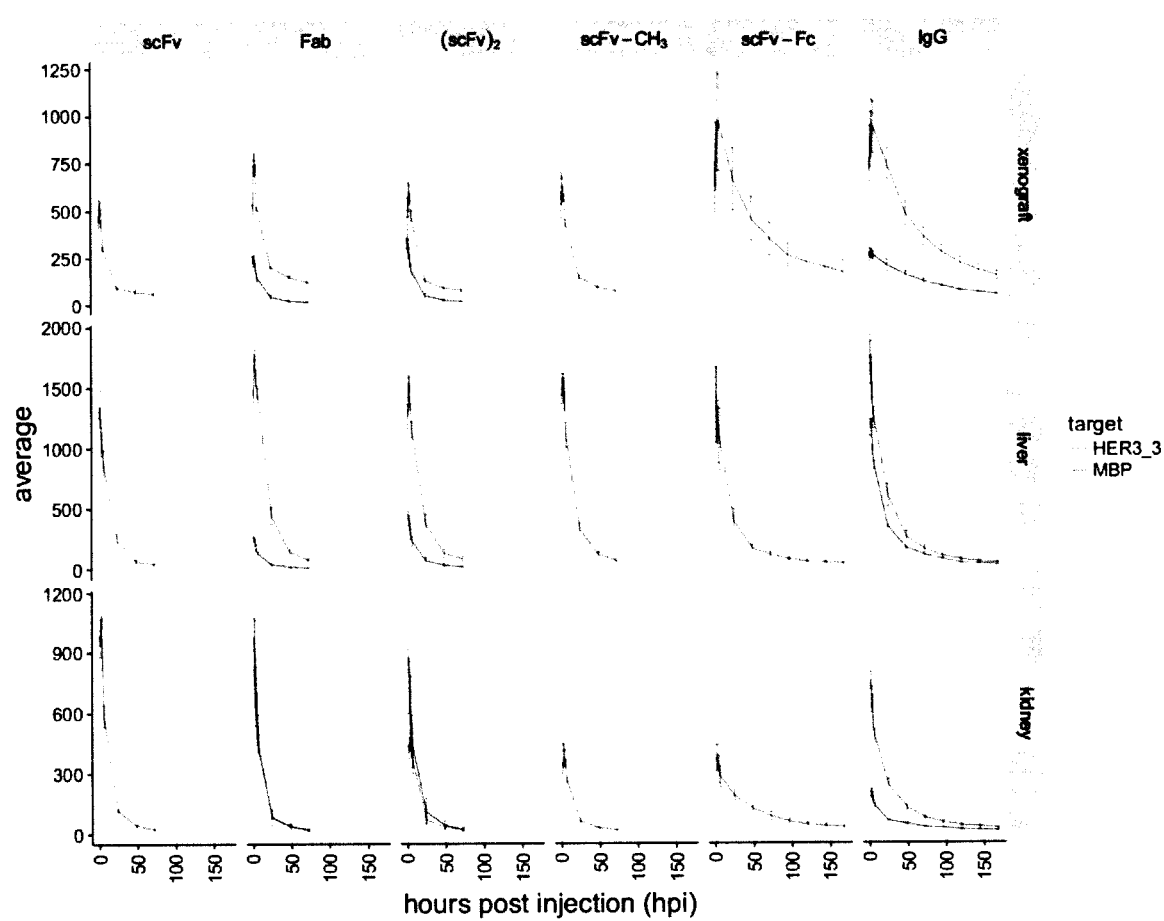
FIG. 17 shows time-fluorescence intensity curves of anti-HER3 fragments and control anti-MBP fragments in different organs.

Time-fluorescence intensity curves of anti-HER3 fragments and control anti-MBP fragments in different organs were generated (FIG. 17).

TABLE 5

Anti-HER3 fragments affinity constants by biolayer interferometry

| Fragment Name | Average $K_D$ nM | Average $K_D$ Error nM | Average $K_{ON}$ (1/Ms) | Average $K_{dis}$ (1/s) |
|---|---|---|---|---|
| HER3 scFv | 21.6 | 1.00 | 60380 | 0.001269 |
| HER3 (scFv)2 | 3.9 | 0.17 | 54080 | 0.000212 |
| HER3 Fab | 3.3 | 0.09 | 39520 | 0.000137 |
| HER3 scFv-CH3 | 0.49 | 0.03 | 96447 | 0.000049 |
| HER3 scFv-Fc | 0.57 | 0.03 | 77840 | 0.000046 |
| HER3 IgG | 0.34 | 0.05 | 25995 | 0.000009 |

Example 3

Summary

In vivo imaging is influenced by the half-life, tissue penetration, biodistribution, and affinity of the imaging probe. Immunoglobulin G (IgG) is composed of discrete domains with known functions, providing a template for engineering antibody fragments with desired imaging properties. Here, antibody-based imaging probes were engineered, consisting of different combinations of antibody domains, labeled them with the near-infrared fluorescent dye IRDye8000W, and their in vivo imaging properties were evaluated. Antibody-based imaging probes were based on an anti-HER3 antigen binding fragment (Fab) isolated using phage display.

Methods: Six anti-HER3 antibody-based imaging probes were constructed: a single chain variable fragment (scFv), Fab, diabody, scFv-$C_H3$, scFv-Fc, and IgG. IRDye8000W-labeled, antibody-based probes were injected into nude mice bearing FaDu xenografts and their distribution to the xenograft, liver, and kidneys was evaluated.

Results: These imaging probes bound to recombinant HER3 and to the HER3-positive cell line, FaDu. Small antibody fragments with molecular weight <60 kDa (scFv, diabody, and Fab) accumulated rapidly in the xenograft (maximum accumulation between 2-4 h post injection (hpi)) and cleared primarily through the kidneys. scFv-$C_H3$ (80 kDa) had fast clearance and peaked in the xenograft between 2-3 hpi and cleared from xenograft in a rate comparable to Fab and diabody. IgG and scFv-Fc persisted in the xenografts for up to 72 hpi and distributed mainly to the xenograft and liver. The highest xenograft fluorescence signals were observed with IgG and scFv-Fc imaging probes and persisted for 2-3 days.

Introduction

Antibodies are a well-established class of biologic affinity reagents with a range of therapeutic applications against cancer, and infectious and inflammatory diseases. The selective, high affinity binding of antibodies to their targets makes them attractive as nuclear or image-guided surgery probes upon conjugation to a radioisotope (Van Dongen et al, 2012) or a near infrared (NIR) fluorescent dye (Vahrmeijer et al, 2013), respectively. Antibodies have a long circulation time due to the interaction of their crystallizable fragment (Fc) with the neonatal Fc receptor (FcRn) on endothelial cells and pH-dependent recycling of antibodies back to circulation (Zalevsky et al, 2010; Beck et al, 2011). This long circulation time makes antibodies optimally-suited for therapeutic applications. Labeling a therapeutic antibody allows real-time tracking of its biodistribution, which can be used to predict therapeutic response. For example, objective responses to trastuzumab therapy were reported in patients who showed intense tumor uptake of $^{111}$In-trastuzumab (Behr et al, 2001), and $^{89}$Zr-Iumretuzumab was used to determine biodistribution in patients before and after receiving a pharmacodynamic-active unlabeled lumretuzumab dose (Bensch et al, 2017). Using antibodies for imaging applications often requires probes with faster clearance and tissue penetration to increase imaging contrast.

Here, the effect of size, valency, and the presence of an Fc domain on tumor accumulation and imaging parameters was examined using a set of six anti-human epidermal growth factor receptor 3 (HER3) antibody-derived imaging probes. HER3 overexpression is correlated with poor survival of patients with solid tumors (Ocana A et al, 2013), particularly in gastric cancer (Hayashi et al, 2008), colorectal cancer (Ledel et al, 2013), ovarian cancer (Tanner et al, 2006), and non-small cell lung carcinomas (Müller-Tidow et al, 2005). HER2/HER3 heterodimer is associated with resistance to anti-HER2 therapies. HER3 imaging probes are needed for detecting HER3 expression, detecting resistance to anti-HER2 therapeutics, identifying patients eligible for combination therapy of HER receptor inhibitors, and predicting patient survival.

An anti-HER3 Fab (HER3-3) was engineered into the following five antibody-based imaging probes of varying sizes: scFv (26.4 kDa), diabody (51.6 kDa), scFv-$C_H3$ (80.2 kDa), scFv-Fc (105.0 kDa), and IgG (150.6 kDa). A direct comparison of these fragments as fluorescent imaging probes for HER3-expressing xenografts. Antibody fragments were labelled with NIR IRDye8000W their biodistribution in mice bearing HER3-expressing xenografts was compared. The results show that antibody fragments can be engineered with properties tailored for image-guided surgery and PET/SPECT imaging.

Methods
Conversion of Anti-HER3 Fab to scFv

To assemble the variable domains of the anti-HER3 Fab into antibody fragments, the Gene Splicing by Overlap Extension or "gene SOEing" polymerase chain reaction (PCR) method was used. Anti-HER3 $V_L$ and $V_H$ genes were PCR-amplified and assembled by gene SOEing to produce an scFv with a 15 amino acid linker (GGGGS; SEQ ID NO: 127)$_3$ in the $V_L$-$V_H$ orientation. To produce the diabody fragment, a short 5 amino acid linker (GGGGS; SEQ ID NO: 127) between the $V_L$ and $V_H$ domains was used. scFv and diabody were cloned into pCW-LIC vector for bacterial expression under the influence of upstream StII (heat-stable enterotoxin 2) secretion sequence.

Expression and Purification of Anti-HER3 Fab, scFv and Diabody pCW-LIC vectors expressing anti-HER3 Fab, scFv, and diabody were transformed into BL21 (DE3) *E. coli* by electroporation. Anti-HER3 Fab, scFv, and diabody were expressed and purified as described herein. Purified antibody fragments were sterilized by filtration through a 0.22 µm sterile syringe filter and stored at 4° C. for short-term storage or at −80° C. for long term storage. Antibody fragment concentration was quantified by measuring absorbance at 280 nm and verified using the BCA protein assay kit (Pierce, Rockford, Ill.). The extinction coefficient was determined using the Expasy protparam tool available on the web. Amino acid sequences of the antibody fragments are listed in Table 6.

Conversion of Anti-HER3 scFv to scFv-Fc, scFv-$C_H$3, and IgG

The $C_H$3 domain with hinge region ($C_H$3-hinge) or $C_H$3-$C_H$2-hinge (Fc) from human IgG1 were PCR amplified from pFUSEss-CHIg-hG1 mammalian expression vector (InvivoGen, San Diego, Calif.) using primers that contain overlapping sequences with anti-HER3 scFv and then assembled into scFv-$C_H$3 or scFv-Fc using gene SOEing. Amplicons were cloned into pFUSEss-CHIg-hG1 vector digested with EcoRI and NsiI (Thermo Fisher Scientific) using Gibson Assembly™ master mix (New England Biolabs, Inc., Ipswich, Mass.). Anti-HER3 IgG1 expression vector was constructed by PCR amplifying $V_H$ and $V_L$ sequences and cloning them into EcoRI/NheI and EcoRI/BsiWI restriction sites in pFUSEss-CHIg-hG1 and pFUSE2ss-CLIg-hk (InvivoGen, San Diego, Calif.), respectively using Gibson Assembly™ protocol.

Expression and Purification of Anti-HER3 scFv-$C_H$3, scFv-Fc, and IgG1

Expi293F cells (Life Technologies Corporation, Carlsbad, Calif.) were cultured in Expi293 Expression Medium (Life Technologies Corporation, Grand Island, N.Y.). Expi293F cells were transfected using an Expifectamine 293 Transfection kit (Gibco, Carlsbad, Calif.), following the manufacturer's protocol. Cells were cultured for 5 days after transfection by shaking at 250 rpm in a 37° C. incubator with 8% $CO_2$. IgG and antibody fragments were harvested from supernatant by centrifugation at 3,000×g for 20 min and filtered using a 0.45 µm filter. scFv-$C_H$3 was purified using GE Healthcare AKTA FPLC system with HiTrap Protein L column (GE healthcare, Sweden). scFv-Fc and IgG1 were purified using HiTrap MabSelect SuRe column (GE healthcare, Sweden). Further purification was performed as described for antibody fragments expressed in *E. Coli*. Protein sequences of antibody fragments are listed in Table 6.

Capillary Electrophoresis Analysis of Anti-HER3 IgG and Antibody Fragments

Chip-based capillary electrophoresis-sodium-dodecyl sulfate (CE-SDS) analysis was used to analyze purified fragments using the Agilent 2100 Bioanalyzer with the Agilent High Sensitivity Protein 250 Kit (cat #5067-1575) under reducing conditions. Samples were diluted to 1 mg/mL and analyzed following the manufacturer's protocol. The size and relative peak area were calculated using Agilent 2100 Expert software.

Binding Kinetics of Anti-HER3 IgG and Antibody Fragments to Recombinant HER3

Binding kinetics were measured using an Octet Red instrument (ForteBio, Menlo Park, Calif.), following the manufacturer's protocol. Binding assays were performed in 96-well microtiter plates at 30° C. with sample plate orbital motion agitation at 1000 rpm. All washes, dilutions, and measurements were performed in phosphate buffered saline (PBS), pH 7.4. The IgG and antibody fragments were immobilized on amine-reactive second generation (AR2G) sensors using the manufacturer's protocol at pH 5 followed by quenching with 1 M ethanolamine, pH 8.5. Recombinant human HER3-Fc chimera protein target (R&D Systems, Minneapolis, Minn.) was serially diluted between 10-263 nM in PBS and placed in different wells. Binding was monitored by placing sensors into wells for 5 min, followed by dissociation in PBS for 10 min. $K_D$, $k_{ON}$, and $k_{OFF}$ were determined with ForteBio Data Analysis software v7.1.0.33 through locally fitting the processed data using a 1:1 binding model.

Labeling of IgG and Antibody Fragments

Antibody fragments were labeled with IRDye800CW-NHS (LI-COR Biosciences, Lincoln, Nebr.), following the manufacturer's protocol. Briefly, the IgG and antibody fragments in PBS, pH 7.4 were mixed with 5-fold molar excess of IRDye800CW-NHS in DMSO and reacted for 2 h at 20° C., followed by overnight incubation at 4° C. protected from light. Excess unbound dye was removed using Zeba Spin Desalting Columns, 5 mL, 7k MWCO (Thermo Scientific). After the free dye was removed, the dye to protein ratio was determined by measuring the labeled protein absorbance in PBS at 280 nm and 774 nm as per the manufacturer's recommendation. Samples were sterilized by filtration and stored protected from light at 4° C. for short-term storage or at −80° C. for long-term storage.

Cell Lines

The HER3-positive human hypopharyngeal squamous cell carcinoma FaDu cell line (ATCC #HTB-43) was propagated by serial passage in MEM/EBSS medium (HyClone Laboratories, Logan Utah) supplemented with 10% fetal bovine serum. Trastuzumab-resistant human breast cancer cell line (TrR1) derived from MDA-MB-231 that stably expresses HER2 was obtained from Dr. Robert Kerbel, Sunnybrook and Women's College Health Sciences Centre in Toronto, Ontario, Canada (Du Manoir et al, 2006). TrR1 cells were cultured in Dulbecco's minimal essential medium (DMEM) supplemented with 10% fetal bovine serum (Sigma-Aldrich). Both cell lines were grown at 37° C. in a humidified atmosphere of 5% $CO_2$.

Flow Cytometry

The binding affinity of labeled anti-HER3 IgG and antibody fragments to FaDu cells was determined by flow cytometry. 1×10$^5$ FaDu cells were incubated with IRDye800CW-labeled IgG or antibody fragments at a concentration of 0.5 µM for 60 min at room temperature, protected from light, followed by three washes with ice-cold PBS, pH 7.4. FaDu cells were then analyzed using a Gallios flow cytometer (Beckman Coulter, Inc.) using Ex 640 nm and Em 745-825 nm (FL8). Live cells were gated on forward and side scatter and 10,000 viable cells were analyzed. IRDye800CW-labeled control IgG or antibody fragments generated against the unrelated maltose-binding protein (MBP) were tested on FaDu cells at 0.1, 0.3, and 1 µM concentrations to confirm that IgG and antibody fragment do not nonspecifically accumulate in the xenograft and to monitor biodistribution. Binding of IRDye800CW-labeled anti-HER3 IgG, Fab, diabody, and scFv-Fc was measured on TrR1 cells (HER3-negative) at 0.1, 0.3, and 1 µM concentrations as a cell line negative control. Flow cytometry data were analyzed using FlowJo software, V10.1 (FlowJo, LLC).

In Vivo Animal Imaging

All animals used in imaging experiments were cared for and maintained under the supervision and guidelines of the University of Saskatchewan Animal Care Committee. Female CD-1 nude mice were obtained from Charles River Canada (St-Constant, Quebec, Canada) at 4 weeks of age and housed in a 12 h light, 12 h dark cycle in a temperature and humidity controlled vivarium. Animals had ad libitum access to mouse diet (Lab Diet, St. Louis, Mo.) and water. After one week of acclimatization, mice were subcutaneously injected with a suspension of $10^7$ FaDu or TrR1 cells in 100 µL of a 1:1 mixture of serum-free medium and Matrigel matrix basement membrane (Discovery Laboware, Inc. Bedford, Mass.) at the hind limb of each mouse. Tumor growth was followed by measuring the greatest length and the greatest width of each tumor using an external caliper. Then, tumor volume was calculated using the formula: tumor volume=length×width$^2$×0.5. When xenografts measured 150-300 mm$^3$ in volume, each mouse was injected intravenously with 0.5 nmol of labeled anti-HER3 or control IgG or antibody fragment through the tail vein. Mice were anesthetized with 2.5% isoflurane and imaged at 1, 2, 3, 4, 6, 24, 48, 72 hpi and up to 168 hpi for scFv-Fc and IgG using the Pearl Impulse Imager (LI-COR). The excitation/emission settings were 785/820 nm. The fluorescence signal was overlaid with the white light image captured by a CCD camera of the imager. Images were analyzed using Image Studio Software (version 3.1). Regions of interest (ROI) for xenografts, liver, kidneys, contralateral side and muscle background were selected from equivalent-sized areas containing the same number of pixels. Three ROIs were quantified per organ for each mouse and three mice were imaged per fragment. Antibody fragments raised against maltose-binding protein and labeled with IRDye800CW served as non-specific control in the imaging experiments.

Statistical Analysis

To compare mean fluorescence intensity in different organs we used two-way analysis of variance (ANOVA) with multiple comparisons using Prism6 version 6. All error bars are standard error of the mean (sem) unless otherwise noted.

Results

Expression and Purification of Anti-HER3 Antibody Fragments

As described herein, an anti-HER3 Fab was previously developed using phage display and showed that it binds human HER3 both in vitro and in vivo (HER3-3). Using this anti-HER3 Fab, an additional four anti-HER3 antibody fragments and an IgG were designed. These were expressed and purified in either E. coli BL21 (DE3) (FIG. 19A) or in mammalian Expi293F cells (FIG. 19B). The size and integrity of the IgG and antibody fragments were confirmed using capillary electrophoresis (FIG. 24). Yields for small fragments expressed in E. coli ranged from 2 mg/L for diabody to 5 mg/L for scFv and Fab. Mammalian cell expression of larger fragments from one plasmid yielded 39 mg/L and 49 mg/L of scFv-$C_H3$ and scFv-Fc, respectively. Expression of IgG from co-transfection with two plasmids resulted in a lower yield of 4 mg/L. Fragments were obtained with purities ranging from 75-96% (FIG. 24).

Affinity of Anti-HER3 Antibody Fragments to Recombinant HER3

Biolayer interferometry was used to measure the binding of the IgG and antibody fragments to recombinant human HER3 (FIG. 25A). The dissociation constants ($K_D$) decreased as the valency of fragments increased for scFv fragments (scFv (20 nM)>diabody (3.0 nM)>scFv-Fc (0.6 nM)>scFv-$C_H3$ (0.5 nM)) and for the Fab versus IgG (Fab (3.5 nM)>IgG (0.3 nM)) (Table 6). The monovalent Fab bound stronger than the monovalent scFv due to a higher off rate ($k_{OFF}$) for the scFv, suggesting the scFv structure was less stable. The diabody bound weaker than other divalent fragments and its $K_D$ was similar to the Fab, suggesting scFv moiety binding was not stable or that scFv was not oriented optimally to simultaneously engage recombinant HER3. Bivalent scFv-$C_H3$, scFv-Fc, and IgG bound similarly with subnanomolar $K_D$. The anti-HER3 IgG preferentially bound human HER3 with 100-fold higher affinity over murine HER3 (FIG. 25B and Table 7).

Binding of Anti-HER3 Antibody Fragments to FaDu and TrR1 Cell Lines

Flow cytometry was used to measure the binding of anti-HER3 IgG and antibody fragments to endogenous HER3 expressed on FaDu cells, a model of squamous cell carcinoma of the head and neck that expresses HER3 [42,43]. IgG and antibody fragments were labeled with IRDye800CW, which has an absorption maximum of 774 nm and an emission maximum of 789 nm. Antibody fragments were labeled at a ratio between 1-2 IRDye800CW molecules per antibody fragment. Labeling the IgG and antibody fragments with IRDye800CW had little effect on their $K_D$ (Table 7). The $K_D$ of scFv-$C_H3$ was affected the most, increasing from 0.5 to 2.1 nM. Binding of antibody fragments to FaDu cells was measured at a concentration of 0.5 µM (FIG. 20A). At this saturating concentration, all antibody fragments bound similarly to FaDu cells. Anti-HER3 IgG and fragments (Fab, diabody, and scFv-Fc) did not bind to HER3-negative TrR1 cells (FIG. 20B). A control IgG and antibody fragments generated against maltose-binding protein and labeled with IRDye800CW at a ratio 1.1-2.0 molecules per protein did not significantly bind FaDu cells (FIG. 20C).

Fluorescence Imaging of Anti-HER3 Antibody Fragments in Xenograft-Bearing Mice

The effectiveness of anti-HER3 antibody fragments as fluorescent imaging probes for HER3-positive FaDu xenografts was evaluated. Mice injected with IRDye800CW-labeled IgG or antibody fragments intravenously at different time points were imaged (FIG. 21A). Antibody fragments accumulated in xenografts at early time points with scFv and scFv-$C_H3$ fragments showing faster clearance of background fluorescence, allowing visualization of the xenografts at 4 hpi. The scFv fragment showed high clearance through the kidneys as early as 1 hpi. By 6 hpi the fluorescence of the scFv fragment started clearing from the xenograft. Xenografts were detectable at 6 hpi with diabody, Fab, and scFv-$C_H3$ fragments. At 24 hpi, diabody, Fab, scFv-$C_H3$, scFv-Fc, and IgG showed accumulation in xenografts with minimal background fluorescence. By 72 hpi antibody fragments with molecular weight less than 100 kDa were mostly cleared from mice. The fluorescence of larger anti-HER3 imaging probes (scFv-Fc and IgG) persisted in xenografts up to 72 hpi. By 72 hpi no significant fluorescence was observed in liver or kidneys for the IgG or antibody fragments.

To confirm that the accumulation of the anti-HER3 IgG and antibody fragments in FaDu xenografts was selective, an IgG and two control antibody fragments generated against the unrelated maltose-binding protein (MBP) that did not bind HER3 were imaged (FIG. 21B). anti-MBP Fab was used as a model for the small monovalent fragments (scFv, Fab), anti-MBP diabody as a model for the bivalent fragments that lacked the Fc domain (diabody and scFv-$C_H3$), and anti-MBP IgG was used as model for the large fragments containing an Fc (scFv-Fc and IgG). Two small, anti-MBP antibody fragments were rapidly cleared from the mice through kidneys with minimal xenograft fluorescence at 6 hpi and no fluorescence at 24 hpi (FIG. 21B). Fluorescence intensities of anti-HER3 scFv and Fab in xenografts were significantly higher than those of anti-MBP Fab at 4 and 6 hpi, while anti-HER3 diabody and scFv-$C_H3$ fluorescence intensities were higher than that of the anti-MBP diabody at 4 and 6 hpi (p value <0.01) (FIG. 26-27). Anti-MBP IgG took longer to distribute and cleared from the mice at a slower rate, mainly through the liver. By 24 hpi there was low fluorescence in the FaDu xenografts (FIG. 21B) in contrast to the significantly higher fluorescence observed with anti-HER3 IgG and scFv-Fc (p value <0.05) (FIG. 28).

The anti-HER3 Fab, diabody, scFv-Fc and IgG were imaged in mice bearing a control HER3-negative TrR1 xenograft (FIG. 21C), which showed no binding to these imaging probes by flow cytometry (FIG. 20B) [34]. These imaging probes were of interest because they showed higher fluorescence signal in the HER3-positive xenografts than their size-equivalent anti-MBP control (FIG. 21C). There was negligible accumulation of anti-HER3 IgG and antibody fragments in the control TrR1 xenografts (FIG. 21C).

The accumulation of IgG and antibody fragments in liver, kidneys, and xenografts was compared. Liver fluorescence was quantified using ventral images of mice. Xenograft and kidney fluorescence was quantified from dorsal images of mice. Mean fluorescence intensities in different organs were plotted against imaging time points (FIG. 22 and FIG. 26-30), which showed that the highest fluorescence intensity in xenografts was observed with scFv-Fc and IgG, which peaked between 4-6 hpi (FIG. 23A). The fluorescence intensity of the Fab and diabody peaked around 3-4 hpi, but had lower intensity than the IgG and scFv-Fc. The fluorescence of the scFv and scFv-$C_H3$ peaked between 2-3 hpi. The anti-HER3 IgG and antibody fragments had high initial liver fluorescence that cleared within 24 hpi. IgG and larger antibody fragments (scFv-$C_H3$ and larger) primarily clear through the liver, consistent with the observed liver accumulation for the anti-HER3 and anti-MBP IgGs and larger antibody fragments. Surprisingly, smaller anti-HER3 antibody fragments (scFv, Fab, diabody) showed accumulation in the liver even though they were expected to clear through the kidney [49, 50-52]. Mice have been previously shown to have HER3 expression in the liver, and the anti-HER3 IgG was found to bind recombinant mouse HER3 (FIG. 25B), but with a higher $K_D$ than with human HER3 (31.8 nM versus 0.3 nM). Together, this suggested that the liver accumulation, particularly for small fragments, was due to endogenous HER3 expression in the liver. Capillary electrophoresis did not show any significant aggregation of labeled small anti-HER3 fragments, excluding the possibility that liver accumulation was due to higher molecular weight aggregates (data not shown). In support of this, it was observed that at 6 and 24 hpi, the anti-HER3 Fab peaked at >1500 fluorescence arbitrary units (AU) in the liver, whereas the anti-MBP Fab peaked at ~250 AU and the anti-HER3 diabody peaked around 1500 AU and the anti-MBP diabody peaked around 500 AU (FIG. 22). In contrast, the kidney distribution was dependent on the molecular weight of the fragment. scFv, diabody, and Fab had high kidney fluorescence, most likely due to kidney excretion of these fragments through filtration. The scFv-$C_H3$, scFv-Fc, and IgG had minimal kidney fluorescence due to their higher molecular weights, which were above the renal molecular weight cut-off. Control small fragments, Fab and diabody, were mainly excreted through kidneys with low liver accumulation. The control IgG localized mainly to the liver with minimal kidney fluorescence.

The fluorescence of a contralateral site on xenografted mice as a proxy measurement for background tissue levels of the IgG and antibody fragments was measured. Anti-HER3 scFv and Fab showed the fastest clearance with contralateral fluorescence values at 24 hpi decreasing to 10% and 14% of their initial values at 1 hpi, respectively. They were followed by diabody and scFv-$C_H3$, which decreased to 19% and 21%, respectively over the same period. On the other hand, scFv-Fc and IgG fluorescence in the contralateral site decreased to 67% and 50% respectively, and their contralateral fluorescence did not differ significantly (p value >0.05) (FIG. 31). By 24 hpi the fluorescence intensities of anti-HER3 scFv-Fc and IgG in the contralateral site were at least triple those of scFv, diabody, Fab, and scFv-$C_H3$ (p value <0.01), indicating slower clearance of scFv-Fc and IgG compared to antibody fragments lacking the Fc domain (FIG. 22).

The fluorescence accumulation of the anti-HER3 fragments was also measured in a control TrR1 xenograft (FIG. 22). The fluorescence signal in the TrR1 xenograft was lower than the signal in the FaDu xenograft at all time points (except the diabody at 1 hpi was slightly higher in the TrR1 xenograft). The anti-HER3 antibody fragments had similar kidney and liver distribution in mice bearing either FaDu or TrR1 xenografts (FIG. 22).

There was a direct proportional correlation between size and time to reach maximum signal in the xenograft (FIG. 23A) with a Pearson correlation of 0.90. Similarly, the Pearson correlation between the size of anti-HER3 IgG or antibody fragments and the maximum signal reached in the xenograft was 0.80 (FIG. 23B). The anti-MBP diabody and Fab reached a maximum of less than 350 AU in less than 2 hpi, while the anti-MBP IgG maximum signal (<300 AU) was reached in less than 4 hpi (FIG. 23C). The smallest antibody fragment, anti-HER3 scFv, reached a maximum signal >500 AU at 2 hpi, while anti-HER3 Fab, diabody, and scFv-$C_H3$ all reached signals >600 AU between 2.5-3.5 hpi. Larger IgG and scFv-Fc reached signals >900 AU at 4.5 and 5.5 hpi, respectively.

Tumor to background ratio (TBR) was calculated for anti-HER3 imaging probes and non-specific anti-MBP probes using the mouse forelimb muscle fluorescence signal as background. In FaDu xenografts, the TBR of the anti-HER3 IgG and antibody fragment imaging probes was 5 or greater at 24 hpi and further increased up to 72 hpi (FIG. 23D). By 72 hpi, anti-HER3 scFv and Fab fragments showed the highest TBR; however, the xenograft fluorescence signal of these imaging probes at 72 hpi was low (60-120 AU). In contrast, anti-HER3 scFv-Fc and IgG imaging probes had TBRs greater than 6 and 9, respectively, and had higher fluorescence signals of ~350 AU. Anti-MBP Fab and diabody had comparable TBRs to their anti-HER3 counterparts up to 24 hpi, but at 48 and 72 hpi TBRs were significantly higher for anti-HER3 probes. Despite comparable TBRs of non-specific tracers signal intensities were significantly higher for anti-HER3 probes at these early time points (FIG. 26-27). The signal for anti-MBP probes steadily decreased in the xenograft in contrast to anti-HER3 probes, which showed accumulation at the early time points followed by clearance later (FIG. 26-27). This fast clearance of the anti-MBP probes resulted in very low background signals, which gave high TBRs values even with the low fluorescence signal of these probes in xenografts, making them unsuited for imaging. The anti-HER3 IgG had higher TBRs than the non-specific anti-MBP IgG at all time points and anti-MBP IgG TBRs were below 5 at all time points. The TBR was calculated for Fab, diabody, scFv-Fc, and IgG imaging probes in HER3-negative TrR1 xenografts. For these imaging probes, TBRs remained less than 5. The TBR for the Fab imaging probe was significantly higher in FaDu xenografts compared to TrR1 xenografts at 24, 48, and 72 hpi (p values <0.05, <0.0001, <0.0001, respectively). The TBR of the diabody and the scFv-Fc were significantly higher in FaDu xenografts compared to TrR1 xenografts at 72 hpi (p value <0.05). The TBR of the IgG was significantly higher at 6, 24, 48, and 72 hpi (p values <0.05, <0.001, <0.0001, and <0.0001, respectively).

Discussion

An IgG and five antibody fragments targeting human HER3 as optical imaging probes for HER3-expressing xenografts were compared. Antibody fragments ranged in molecular weight from 25 kDa to 150 kDa and had either monovalent binding (scFv, and Fab) or bivalent binding (diabody, scFv-$C_H$3, scFv-Fc, and IgG). Two fragments tested had an Fc domain (scFv-Fc and IgG), while one fragment had the $C_H$3 domain of the Fc (scFv-$C_H$3). IgG and antibody fragments were labeled with IRDye800CW, which is an ideal fluorescent dye for in vivo imaging as it avoids interference caused by the natural background fluorescence of tissues.

The effect of valency on binding to recombinant HER3 was analyzed and it was observed that the bivalent fragments bound stronger to HER3, which was consistent with increased avidity seen previously with diabody and IgGs relative to the scFv and Fab (Klein et al; 2009). The monovalent scFv bound weaker to HER3 relative to the bivalent diabody, scFv-$C_H$3, and scFv-Fc. Similarly, the Fab bound weaker than the IgG. The major difference in binding between the monovalent and bivalent fragments was a slower $k_{OFF}$ for bivalent fragments. For the monovalent fragments, the scFv had a higher $K_D$ than the Fab, with the scFv having a faster $k_{OFF}$. In this case, constant domains ($C_H$1, $C_L$) of the Fab may play a role in stabilizing Fab binding to its target (Torres et al, 2007). Previous reports suggested that the $C_H$1 domain plays a role in structuring the antigen-binding site into a more kinetically competent form (Protsch et al, 1996). For the bivalent fragments, the diabody had the highest $K_D$ due to its fast $k_{OFF}$. In this case, the scFv domains in the diabody may not be optimally oriented to engage two HER3 molecules, or the diabody may be less stable than the other bivalent fragments. The anti-HER3 antibody and fragments bound endogenous HER3 expressed on the FaDu cell line equally well at saturating concentrations.

Mice engrafted with HER3-positive FaDu xenografts were used to characterize accumulation of the anti-HER3 IgG and antibody fragments. Correlations were observed between fragment size and time required to obtain maximum xenograft fluorescence and the intensity of the xenograft fluorescence. Smaller fragments required less time to attain a maximum fluorescence signal in the xenograft and had lower xenograft fluorescence. The exception to these trends was the scFv-$C_H$3 fragment, which had a maximum signal similar to the smaller diabody and required less time to reach its maximum signal. It is possible the scFv-$C_H$3 was not stable in vivo (Olafsen et al, 2004) or the lack of a Fc domain caused it to clear similarly to the diabody.

Mice engrafted with HER3-positive FaDu and HER3-negative TrR1 xenografts were compared to characterize liver and kidney biodistribution and body clearance of the anti-HER3 IgG and its fragments. The IgG and antibody fragments accumulated in the liver at early time points. This liver distribution has been reported previously for IgG, scFv-Fc, and scFv-$C_H$3 (Olafsen et al, 2005), but was not expected for fragments below 60 kDa as they were below the filtration molecular weight cut-off of the kidneys (Ravn et al, 2007) and scFvs do not generally accumulate in the liver (Begent et al, 1996; Pavlinkova et al, 1999; Schneider et al, 2009). Liver accumulation has been reported previously for a small anti-HER3 affibody and this is proposed to be due to the interaction with endogenous HER3 expression in the liver (Malm et al, 2013) and this was likely the cause for the observed liver accumulation. Both affibody (Malm et al, 2013) and anti-HER3 antibody fragments bound murine HER3. In support of this, significant accumulation of the anti-MBP control Fab and diabody fragments was not observed in the liver, whereas the control anti-MBP IgG showed high levels of liver accumulation.

A correlation between fragment size and kidney accumulation was observed. Smaller anti-HER3 and anti-MBP control antibody fragments with molecular weights below the renal filtration cut-off (scFv, Fab, and diabody) showed high levels of kidney accumulation at early time points. Previous studies have shown that scFvs (Begent et al, 1996; Pavlinkova et al, 1999; Schneider et al, 2009), Fabs (Covell et al, 1986; Tang et al, 2005) and diabodies (Holliger et al, 2005; Schneider et al, 2009) are primarily cleared through the kidneys. The anti-MBP control IgG, anti-HER3 IgG and larger antibody fragments (scFv-$C_H$3 and scFv-Fc) showed much lower accumulation in the kidneys. For IgGs, the anti-HER3 IgG showed higher initial kidney accumulation than the anti-MBP control IgG and the anti-HER3 scFv-$C_H$3 and scFv-Fc; the reason for this accumulation was not clear. However, PET imaging of patients injected with another anti-HER3 IgG ($^{89}$Zr-Iumretuzumab) also showed high tracer accumulation in kidneys (Bensch et al, 2017).

The fluorescence of a contralateral site to the xenograft as a proxy measurement for background tissue levels of IgG and antibody fragments was measured. It was observed that antibody fragments lacking an Fc domain showed faster rates of fluorescence clearance from the contralateral site. The smallest fragments (scFv and Fab) showed the fastest levels of contralateral site clearance followed by the diabody and scFv-$C_H$3. This correlation between the clearance from the contralateral site and the presence of the Fc domain was likely due to the recycling of Fc domain-containing proteins back to the circulation through FcRn receptor (Beck et al, 2011; Behr et al, 2001).

It was observed that the anti-HER3 IgG and antibody fragments had similar TBRs that increased over time. The absolute fluorescence intensity in the xenograft was higher for the Fc-containing imaging probes (IgG, scFv-Fc), especially at 72 hpi where the TBRs were highest. Thus, for targets like HER3, which have low receptor density (Rosestedt et al., 2015) on the tumor and endogenous expression in tissues, imaging probes with longer circulation times are needed to provide sufficient time to accumulate at high levels in the tumor and clear from tissues. The larger Fc-containing fragments (IgG, scFv-Fc) have the required longer circulation half-lives and would be suitable for imaging-guided surgery, which is an intraoperative or endoscopic procedure where high fluorescence signal and TBR are desirable for tumor detection and margin delineation, respectively. The larger Fc-containing fragments would also be useful for PET imaging using radionuclides with long half-lives. The Fab may be useful for PET imaging at early time points as it showed the highest xenograft fluorescence of the antibody fragments without an Fc domain. The Fab has the advantage of faster body clearance, which for PET would allow the use of short-lived radionuclides and reduce radiation exposure.

CONCLUSION

There are currently no FDA-approved imaging probes for monitoring in vivo HER3 expression in tumors. Here, a set of six imaging probes consisting of an IgG and antibody fragments, ranging in size from 25 kDa to 150 kDa with monovalent or bivalent binding, were constructed and analyzed their imaging properties. Their xenograft accumulation, biodistribution, and clearance properties were examined to identify antibody fragments that showed the best properties for developing PET/SPECT and imaging-guided surgery probes. A correlation between antibody fragment size and time to reach maximum signal and the value of the maximum signal was observed. TBRs of the anti-HER3 IgG and antibody fragments increased overtime with the Fc-containing imaging probes showing the highest fluorescence after 72 hpi. HER3 is expressed at low levels in the tumor and has endogenous expression in tissues. Good images of HER3-positive xenografts were obtained with HER3 imaging probes with longer circulation times. Longer circulation half-lives provide imaging probes sufficient time to accumulate in the tumor and to clear from other tissues.

TABLE 6

Protein sequences for anti-HER3 antibody fragments

| Anti-HER3 fragment | Amino acid sequence |
|---|---|
| scFv | SDIQMTQSPSSLSASVGDRVTITCRASQGISNYLAWYQQKPGKAPKLLIY AASSLQSGVPSRFSGSRSGTDFTLTISSLQPEDFATYYCQQYGWLPLTF GQGTKVEIKGGGGSGGGGSGGGGSEISEVQLVESGGGLVQPGGSLRL SCAASGFTFSSYGMHWVRQAPGKGLEWVAVISYDGSNKYYADSVKGR FTISRDNSKNTLYLQMNSLRAEDTAVYYCARTDPYSLGGYYFDYWGQG TLVTVSS (SEQ ID NO: 83) |
| diabody | SDIQMTQSPSSLSASVGDRVTITCRASQGISNYLAWYQQKPGKAPKLLIY AASSLQSGVPSRFSGSRSGTDFTLTISSLQPEDFATYYCQQYGWLPLTF GQGTKVEIKGGGGSEISEVQLVESGGGLVQPGGSLRLSCAASGFTFSS YGMHWVRQAPGKGLEWVAVISYDGSNKYYADSVKGRFTISRDNSKNTL YLQMNSLRAEDTAVYYCARTDPYSLGGYYFDYWGQGTLVTVSS (SEQ ID NO: 84) |
| Fab | Light Chain: SDIQMTQSPSSLSASVGDRVTITCRASQGISNYLAWYQQKPGKAPKLLIY AASSLQSGVPSRFSGSRSGTDFTLTISSLQPEDFATYYCQQYGWLPLTF GQGTKVEIKRTVAAPSVFIFPPSDSQLKSGTASVVCLLNNFYPREAKVQ WKVDNALQSGNSQESVTEQDSKDSTYSLSSTLTLSKADYEKHKVYACE VTHQGLSSPVTKSFNRGECGGSDYKDDDDK (SEQ ID NO: 85) Heavy Chain: EISEVQLVESGGGLVQPGGSLRLSCAASGFTFSSYGMHWVRQAPGKGL EWVAVISYDGSNKYYADSVKGRFTISRDNSKNTLYLQMNSLRAEDTAVY YCARTDPYSLGGYYFDYWGQGTLVTVSSASTKGPSVFPLAPSSKSTSG GTAALGCLVKDYFPEPVTVSWNSGALTSGVHTFPAVLQSSGLYSLSSVV TVPSSSLGTQTYICNVNHKPSNTKVDKKVEPKSCDKTHTGGSHHHHHH (SEQ ID NO: 86) |
| scFv-$C_H3$ | SDIQMTQSPSSLSASVGDRVTITCRASQGISNYLAWYQQKPGKAPKLLIY AASSLQSGVPSRFSGSRSGTDFTLTISSLQPEDFATYYCQQYGWLPLTF GQGTKVEIKGGGGSGGGGSGGGGSEISEVQLVESGGGLVQPGGSLRL SCAASGFTFSSYGMHWVRQAPGKGLEWVAVISYDGSNKYYADSVKGR FTISRDNSKNTLYLQMNSLRAEDTAVYYCARTDPYSLGGYYFDYVVGQG TLVTVSSEPKSCDKTHTCPPCPGQPREPQVYTLPPSREEMTKNQVSLT CLVKGFYPSDIAVEWESNGQPENNYKTTPPVLDSDGSFFLYSKLTVDKS RWQQGNVFSCSVMHEALHNHYTQKSLSLSPGK (SEQ ID NO: 87) |
| scFv-Fc | SDIQMTQSPSSLSASVGDRVTITCRASQGISNYLAWYQQKPGKAPKLLIY AASSLQSGVPSRFSGSRSGTDFTLTISSLQPEDFATYYCQQYGWLPLTF GQGTKVEIKGGGGSGGGGSGGGGSEISEVQLVESGGGLVQPGGSLRL SCAASGFTFSSYGMHWVRQAPGKGLEWVAVISYDGSNKYYADSVKGR FTISRDNSKNTLYLQMNSLRAEDTAVYYCARTDPYSLGGYYFDYVVGQG TLVTVSSEPKSCDKTHTCPPCPAPELLGGPSVFLFPPKPKDTLMISRTPE VTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSR EEMTKNQVSLTCLVKGFYPSDIAVEWESNGQPENNYKTTPPVLDSDGS FFLYSKLTVDKSRWQQGNVFSCSVMHEALHNHYTQKSLSLSPGK (SEQ ID NO: 88) |

TABLE 6-continued

Protein sequences for anti-HER3 antibody fragments

| Anti-HER3 fragment | Amino acid sequence |
|---|---|
| IgG | Light Chain:<br>SDIQMTQSPSSLSASVGDRVTITCRASQGISNYLAWYQQKPGKAPKLLIY<br>AASSLQSGVPSRFSGSRSGTDFTLTISSLQPEDFATYYCQQYGWLPLTF<br>GQGTKVEIKRTVAAPSVFIFPPSDEQLKSGTASVVCLLNNFYPREAKVQ<br>WKVDNALQSGNSQESVTEQDSKDSTYSLSSTLTLSKADYEKHKVYACE<br>VTHQGLSSPVTKSFNRGEC<br>(SEQ ID NO: 89)<br>Heavy Chain:<br>EISEVQLVESGGGLVQPGGSLRLSCAASGFTFSSYGMHWVRQAPGKGL<br>EWVAVISYDGSNKYYADSVKGRFTISRDNSKNTLYLQMNSLRAEDTAVY<br>YCARTDPYSLGGYYFDYWGQGTLVTVSSASTKGPSVFPLAPSSKSTSG<br>GTAALGCLVKDYFPEPVTVSWNSGALTSGVHTFPAVLQSSGLYSLSSVV<br>TVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPI<br>EKTISKAKGQPREPQVYTLPPSREEMTKNQVSLTCLVKGFYPSDIAVEW<br>ESNGQPENNYKTTPPVLDSDGSFFLYSKLTVDKSRWQQGNVFSCSVM<br>HEALHNHYTQKSLSLSPGK<br>(SEQ ID NO: 90) |

TABLE 7

Anti-HER3 IgG and antibody fragments binding kinetics

| Antibody Format | Valency | Average Expression Yield (mg/L) | Average $K_D$ (nM) | Average $k_{ON}$ (×10$^4$ M$^{-1}$ s$^{-1}$) | Average $k_{OFF}$ (×10$^{-4}$ s$^{-1}$) | Average $K_D$ of IRDye800CW-labeled antibody (nM) |
|---|---|---|---|---|---|---|
| scFv | Monovalent | 5 | 20 ± 1.4 | 3.3 ± 0.1 | 5.4 ± 0.3 | 29 ± 3.7 |
| Fab | Monovalent | 5 | 3.5 ± 0.1 | 4.9 ± 0.1 | 1.7 ± 0.1 | 3.2 ± 0.1 |
| diabody | Bivalent | 2 | 3.0 ± 0.2 | 15 ± 0.1 | 4.4 ± 0.3 | 2.4 ± 0.2 |
| scFv-$C_H$3 | Bivalent | 39 | 0.5 ± 0.1 | 9.6 ± 0.1 | 0.5 ± 0.1 | 2.1 ± 0.1 |
| scFv-Fc | Bivalent | 49 | 0.6 ± 0.1 | 7.8 ± 0.2 | 0.5 ± 0.1 | 0.9 ± 0.1 |
| IgG | Bivalent | 4 | 0.3 ± 0.1<br>(31.8 ± 0.5)* | 2.6 ± 0.1<br>(0.5 ± 0.1)* | 0.10 ± 0.01<br>(1.7 ± 0.1)* | 0.5 ± 0.1 |

TABLE 8

HER3-3 CDR sequences as defined by IGMT numbering

| | | SEQ ID NO: |
|---|---|---|
| CDR-L1 | QGISNY | 117 |
| CDR-L2 | AAS | 118 |
| CDR-L3 | QQYGWLPLT | 119 |
| CDR-H1 | GFTFSSYG | 120 |
| CDR-H2 | ISYDGSNK | 121 |
| CDR-H3 | ARTDPYSLGGYYFDY | 122 |

Abbreviations

AU: fluorescence arbitrary units; CE-SDS: chip-based capillary electrophoresis-sodium-dodecyl sulfate; $C_H1$: constant heavy domain 1; $C_H2$: constant heavy domain 2; $C_H3$: constant heavy domain 3; DMEM: Dulbecco's minimal essential medium; E. coli: Escherichia coli; Fab: antigen-binding fragment; Fc: crystallizable fragment; FcRn: neonatal Fc receptor; HER2: human epidermal growth factor receptor 2; HER3: human epidermal growth factor receptor 3; hpi: hours post-injection; IFOM: imaging figure of merit; IgG: immunoglobulins; $K_D$: dissociation constant; MBP: maltose-binding protein; NIR: near-infrared; PBS: phosphate buffered saline; PCR: polymerase chain reaction; PET: positron emission tomography; % ID/g: percent injected dose per gram; scFv: single chain variable fragment; TBR: Tumor to background ratio; $V_L$: variable light domain; $V_H$: variable heavy domain.

REFERENCES

C. R. Geyer, J. McCafferty, S. Dubel, A. R. Bradbury, S. S. Sidhu, Methods Mol. Biol. 2012, 901, 11-32.

C. M. Mahon, M. A. Lambert, J. Glanville, J. M. Wade, B. J. Fennell, M. R. Krebs, D. Armellino, S. Yangm X. Liu, C. M. O'Sullivan, J. Mol. Biol. 2013, 425, 1712-1730; A. E. Nixon, D. J. Sexton, R. C. Ladner, mAbs 2014, 6, 73-85.

A. Frenzel, T. Schirrmann, M. Hust, mAbs 2016, 8, 1177-1194.

S. W. Michnick, S. S. Sidhu, Nat. Chem. Biol. 2008, 4, 326-329.

S. S. Sidhu, FEBS Lett. 2012, 586, 2778-2779.

H. Shim, Curr. Pharm. Des. 2016, 22, 6538-6559.

D. Ponsel, J. Neugebauer, K. Ladetzki-Baehs, K. Tissot, Molecules 2011, 16, 3675-3700.

N. Harel-Inbar, I. Benhar, *Arch. Biochem. Biophys.* 2012, 526, 87-98.

J. J. Adams, S. S. Sidhu, *Curr. Opin. Struct. Biol.* 2014, 24, 1-9.

S. Miersch, S. S. Sidhu, *Methods* 2012, 57, 486-498.

P. Carter, L. Presta, C. M. Gorman, J. B. Ridgway, D. Henner, W. L. Wong, A. M. Rowland, C. Kotts, M. E. Carver, H. M. Shepard, *Proc. Natl. Acad. Sci.* 1992, 89, 4285-4289.

H. Na, J. D. Laver, J. Jeon, F. Singh, K. Ancevicius, Y. Fan, W. X. Cao, K. Nie, Z. Yang, H. Luo, M. Want, O. Rissland, J. T. Westwood, P. M. Kim, C. A. Smibert, H. D. Lipshitz, S. S. Sidhu, *RNA* 2016, 22, 636-655.

F. A. Fellouse, K. Esaki, S. Birtalan, D. Raptis, V. J. Cancasci, A. Koide, P. Jhurani, M. Vasser, C. Wiesmann, A. A. Kossiakoff, S. Koide, S. S. Sidhu, *J. Mol. Biol.* 2007, 373, 924-940.

H. Persson, W. Ye, A. Wernimont, J. J. Adams, A. Koide, S. Koide, R. Lam, S. S. Sidhu, *J. Mol. Biol.* 2013, 425, 803-811.

C. V. Lee, W. C. Liang, M. S. Dennis, C. Eigenbrot, S. S. Sidhu, G. Fuh, *J. Mol. Biol.* 2004a, 340, 1073-1093.

R. F. Kelley, M. P. O'Connell, P. Carter, L. Presta, C. Eigenbrot, M. Covarrubias, B. Snedecor, J. H. Bourell, D. Vetterlein, *Biochemistry* 1992, 31, 5434-5441.

C. Eigenbrot, M. Randal, L. Presta, P. Carter, A. A. Kossiakoff, *J. Mol. Biol.* 1993, 229, 969-995.

A. C. Martin, J. M. Thornton, *J. Mol. Biol.* 1996, 263, 800-815.

B. Al-Lazikani, A. M. Lesk, C. Chothia, *J. Mol. Biol.* 1997, 273, 927-948.

V. Morea, A. Tramontano, M. Rustici, C. Chothia, A. M. Lesk, *J. Mol. Biol.* 1998, 275, 269-294.

C. Rothe, S. Urlinger, C. Lohning, J. Prassler, Y. Stark, U. Jager, B. Hubner, M. Bardoff, I. Pradel, M. Boss, R. Bittlingmaier, T. Bataa, C. Frisch, B. Brocks, A. Honegger, M. Urban, *J. Mol. Biol.* 2008, 376, 1182-1200.

J. Prassler, S. Thiel, C. Pracht, A. Polzer, S. Peters, M. Bauer, S. Norenberg, Y. Stark, J. Kolln, A. Popp, S. Urlinger, M. Enzelberger, *J. Mol. Biol.* 2011, 413, 261-278.

T. Tiller, I. Schuster, D. Deppe, K. Siegers, R. Strohner, T. Herrmann, M. Berenguer, D. Poujol, J. Stehle, Y. Stark, M. Hebling, D. Daubert, K. Felderer, S. Kaden, J. Kolln, M. Enzelberger, S. Urlinger, *mAbs* 2013, 5, 445-470.

C. Chothia, A. M. Lesk, E. Gherardi, I. M. Tomlinson, G. Walters, J. D. Marks, M. B. Llewelyn, G. Winter, *J. Mol. Biol.* 1992, 227, 799-817.

A. Knappik, L. Ge, A. Honegger, P. Pack, M. Fischer, G. Wellnhofer, A. Hoess, J. Wolle, A. Pluckthun, B. Virnekas, *J. Mol. Biol.* 2000, 296, 57-86.

B. North, A. Lehmann, R. L. Dunbrack, *J. Mol. Biol.* 2011, 406, 228-256. M. Zemlin, M. Klinger, J. Link, C. Zemlin, K. Bauer, J. A. Engler, H. W. Schroeder, P. M. Kirkham, *J. Mol. Biol.* 2003, 334, 733-749.

C. V. Lee, S. S. Sidhu, G. Fuh, *J. Immunol. Methods* 2004b, 284, 119-132. J. Ma, H. Lyu, H. Huang, *Mol. Cancer* 2014, 13, 105.

K, Zhang, P. Wong, C. Salvaggio, A. Salhi, I. Osman, B. Bedogni, *J. Invest. Dermatol.* 2015, 136, 464-472.

C. Mirschberger, C. B. Schiller, M. Schraml, N. Dimoudis, T. Friess, C. A. Gerdes, U. Reiff, V. Lifke, G. Hoelzlwimmer, I. Kolm, K. P. Hopfner, G. Niederfellner, B. Bossenmaier, *Cancer Res.* 2013, 73, 5183-5194.

A. G. Terwisscha Van Scheltinga, M. N. Lub-de Hooge, K. Abiraj, M. P. Schroder, L. Pot, B. Bossenmaier, M. Thomas, G. Holzlwimmer, T. Friess, J. G. W. Kosterink, E. G. E deVries, *mAbs* 2014, 6, 1051-1058.

D. M. Goldenberg, et al., *Cancer Res.* 1990, 50, 909-921.

T. A. Kunkel, J. D. Roberts, R. A. Zakour, *Methods Enzymol.* 1987, 154, 367-382. F. A. Fellouse, S. S. Sidhu, *Making and Using Antibodies: A Practical Handbook*, CRC Press, 2006, pp. 157-180.

S. Rajan, S. S. Sidhu, *Methods Enzymol.* 2012, 502, 3-23.

R Core Team, *R: A Language and Environment for Statistical Computing*, R Foundation for Statistical Computing, 2013, ISBN 3-900051-07-0.

J. M. duManoir, G. Francia, S. Man, M. Mossoba, J. A. Medin, A. Viloria-Petit, D. J. Hicklin, U. Emmenegger, R. S. Kerbel, *Clin Cancer Res.* 2006, 12, 904-916.

M. S. Dahabieh, M. Ooms, C. Brumme, J. Taylor, P. R. Harrigan, V. Simon, I. Sadowski, *Retrovirology* 2014, 11, 17.

Kabat et al., 1991. *Sequences of Proteins of Immunological Interest*, 5th Ed. Public Health Service, National Institutes of Health, Bethesda, Md.

M. Hornsby, M. Paduch, S. Miersch, A. Saaf, T. Matsuguchi, B. Lee, K. Wypisniak, A. Doak, D. King, S. Usatyuk, K. Perry, V. Lu, W. Thomas, J. Luke, J. Goodman, R. J. Hoey, D. Lai, C. Griffin, Z. Li, F. J. Vizeacoumar, D. Dong, E. Campbell, S. Anderson, N. Zhong, S. Graslund, S. Koide, J. Moffat, S. Sidhu, A. Kossiakoff, J. Wells, Mol. Cell. Proteomics 2015, 14, 2833-2847.

Y. Tang, J. Wang, D. A. Scollard, H. Mondal, C. Holloway, H. J. Kahn, R. M. Reilly, Nucl. Med. Biol. 2005, 32, 51-8.

D. G. Covell, J. Barbet, O. D. Holton, C. D. Black, R. J. Parker, J. N. Weinstein, Cancer Res. 1986, 46, 3969-78.

D. M. Goldenberg, et al., Cancer Res. 1990, 50, 909-921.

I. Sela-Culang, V. Kunik, Y. Ofran, Front Immunol. 2013, 8, 1-13.

C. R. MacKenzie, T. Hirama, S. J. Deng, D. R. Bundle, S. A. Narang, N. M. Young, J Biol Chem. 1996, 19, 1527-33.

A. M. Wu, Methods 2014, 1, 139-47.

A. C. Freise, A. M. Wu, Mol Immunol. 2015, 67, 142-52.

I. Colombo, M. Overchuk, J. Chen, R. M. Reilly, G. Zheng, S. Lheureux, Methods 2017, 16, 30341-3.

G. Abbineni, S. Modali, B. Safiejko-Mroczka, V. A. Petrenko, C. Mao, Mol. Pharmaceutics 2010, 7, 1629-42.

K. S. Sunderland, M. Yang, C. Mao, Angew. Chem. Int. Ed. 2017, 56, 1964-92. A. Burkovitz, Y. Ofran, mAbs 2016, 8, 278-87.

T. Ramaraj, T. Angel, E. A. Dratz, A. J. Jesaitis, B. Mumey, Biochim Biophys Acta 2012, 1824, 520-32.

Van Dongen G A M S, Poot A J, Vugts D J. PET imaging with radiolabeled antibodies and tyrosine kinase inhibitors: Immuno-PET and TKI-PET. Tumor Biol. 2012; 33: 607-15.

Vahrmeijer A L, Hutteman M, van der Vorst J R, van de Velde C J H, Frangioni J V. Image-guided cancer surgery using near-infrared fluorescence. Nat Rev Clin Oncol. 2013; 10: 507-18.

Zalevsky J, Chamberlain A K, Horton H M, Karki S, Leung IWL, Sproule T J, et al. Enhanced antibody half-life improves in vivo activity. Nat Biotechnol. 2010; 28: 157-9.

Beck A, Reichert J M. Therapeutic Fc-fusion proteins and peptides as successful alternatives to antibodies. MAbs. 2011; 3: 415-6.

Behr T M, Béhé M, Wormann B. Trastuzumab and breast cancer. N Engl J Med. 2001; 345: 995-6.

Bensch F, Lamberts L E, Smeenk M M, Jorritsma-Smit A, Lub-de Hooge M N, Terwisscha van Scheltinga A G T, et al. (89)Zr-Iumretuzumab PET imaging before and during HER3 antibody Iumretuzumab treatment in patients with solid tumors. Clin Cancer Res. 2017; 23: 6128-37.

Ocana A, Vera-Badillo F, Seruga B, Templeton A, Pandiella A, Amir E. HER3 overexpression and survival in solid tumors: A meta-analysis. J Natl Cancer Inst. 2013; 105: 266-73.

Hayashi M, Inokuchi M, Takagi Y, Yamada H, Kojima K, Kumagai J, et al. High expression of HER3 is associated with a decreased survival in gastric cancer. Clin Cancer Res. 2008; 14: 7843-9.

Ledel F, Hallstrom M, Ragnhammar P, Ohrling K, Edler D. HER3 expression in patients with primary colorectal cancer and corresponding lymph node metastases related to clinical outcome. Eur J Cancer. 2014; 50: 656-62.

Tanner B, Hasenclever D, Stern K, Schormann W, Bezler M, Hermes M, et al. ErbB-3 predicts survival in ovarian cancer. J Clin Oncol. 2006; 24: 4317-23.

Müller-Tidow C, Diederichs S, Bulk E, Pohle T, Steffen B, Schwable J, et al. Identification of metastasis-associated receptor tyrosine kinases in non-small cell lung cancer. Cancer Res. 2005; 65: 1778-82.

Sergina N V, Rausch M, Wang D, Blair J, Hann B, Shokat K M, et al. Escape from HER-family tyrosine kinase inhibitor therapy by the kinase-inactive HER3. Nature. 2007; 445: 437-41.

Huang X, Gao L, Wang S, McManaman J L, ThorAD, Yang X, et al. Heterotrimerization of the growth factor receptors erbB2, erbB3, and insulin-like growth factor-I receptor in breast cancer cells resistant to herceptin. Cancer Res. 2010; 70: 1204-14. [Internet] Immuno positron emission tomography study of GSK2849330 in subjects with human epidermal growth factor receptor 3-positive solid tumors. https://clinicaltrials.gov/ct2/show/NCT02345174

Lockhart A C, Liu Y, Dehdashti F, Laforest R, Picus J, Frye J, et al. Phase 1 evaluation of [64Cu]DOTA-patritumab to assess dosimetry, apparent receptor occupancy, and safety in subjects with advanced solid tumors. Mol Imaging Biol. 2016; 18: 446-53. Yuan Q, Furukawa T, Tashiro T, Okita K, Jin Z H, Aung W, et al. Immuno-PET imaging of HER3 in a model in which HER3 signaling plays a critical role. PLoS One. 2015; 10: e0143076.

Orlova A, Malm M, Rosestedt M, Varasteh Z, Andersson K, Selvaraju R K, et al. Imaging of HER3-expressing xenografts in mice using a 99mTc(CO) 3-HEHEHE-ZHER3:08699 affibody molecule. Eur J Nucl Med Mol Imaging. 2014; 41: 1450-9.

Rosestedt M, Andersson K G, Mitran B, Tolmachev V, Lofblom J, Orlova A, et al. Affibody-mediated PET imaging of HER3 expression in malignant tumours. Sci Rep. 2015; 5:15226.

Da Pieve C, Allott L, Martins C D, Vardon A, Ciobota D M, Kramer-Marek G, et al. Efficient [18F]AlF radiolabeling of ZHER3:8698 affibody molecule for imaging of HER3 positive tumors. Bioconjug Chem. 2016; 27: 1839-49.

Vellalore Maruthachalam B, E I-Sayed A, Liu J, Hill W, Sutherland A, Pastushok L, et al. A single-framework synthetic antibody library containing a combination of canonical and variable complementarity determining regions. Chembiochem. 2017; 18: 2247-2259.

Du Manoir J M, Francia G, Man S, Mossoba M, Medin J A, Viloria-Petit A, et al. Strategies for delaying or treating in vivo acquired resistance to trastuzumab in human breast cancer xenografts. Clin Cancer Res. 2006; 12: 904-16.

Garner A P, Bialucha C U, Sprague E R, Garrett J T, Sheng Q, Li S, et al. An antibody that locks HER3 in the inactive conformation inhibits tumor growth driven by HER2 or neuregulin. Cancer Res. 2013; 73: 6024-35.

Terwisscha van Scheltinga AGT, Lub-de Hooge M N, Abiraj K, Schroder C P, Pot L, Bossenmaier B, et al. Immuno-PET and biodistribution with human epidermal growth factor receptor 3 targeting antibody (8)(9)Zr-RG7116. MAbs. 2014; 6: 1051-8.

Klein J S, Gnanapragasam PNP, Galimidi R P, Foglesong C P, West A P, Bjorkman P J. Examination of the contributions of size and avidity to the neutralization mechanisms of the anti-HIV antibodies b12 and 4E10. Proc Natl Acad Sci USA. 2009; 106:7385-90.

Torres M, Fernandez-Fuentes N, Fiser A, Casadevall A. The immunoglobulin heavy chain constant region affects kinetic and thermodynamic parameters of antibody variable region interactions with antigen. J Biol Chem. 2007; 282: 13917-27.

Pritsch O, Hudry-Clergeon G, Buckle M, Petillot Y, Bouvet J P, Gagnon J, et al. Can immunoglobulin C(H)1 constant region domain modulate antigen binding affinity of antibodies? J Clin Invest. 1996; 98: 2235-43.

Olafsen T, Tan G J, Cheung C W, Yazaki P J, Park J M, Shively J E, et al. Characterization of engineered anti-p185HER-2 (scFv-C H3)2 antibody fragments (minibodies) for tumor targeting. Protein Eng Des Sel. 2004; 17: 315-23.

Ravn P, Stahn R, Danielczyk A, Faulstich D, Karsten U, Goletz S. The Thomsen-Friedenreich disaccharide as antigen for in vivo tumor targeting with multivalent scFvs. Cancer Immunol Immunother. 2007; 56: 1345-57.

Begent R H J, Verhaar M J, Chester K A, Casey J L, Green A J, Napier M P, et al. Clinical evidence of efficient tumor targeting based on single-chain Fv antibody selected from a combinatorial library. *Nat Med.* 1996; 2: 979-84.

Pavlinkova G, Beresford G W, Booth B J, Batra S K, Colcher D. Pharmacokinetics and biodistribution of engineered single-chain antibody constructs of MAb CC49 in colon carcinoma xenografts. *J Nucl Med.* 1999; 40: 1536-46.

Schneider D W, Heitner T, Alicke B, Light D R, McLean K, Satozawa N, et al. In vivo biodistribution, PET imaging, and tumor accumulation of 86Y- and 111In-antimindin/RG-1, engineered antibody fragments in LNCaP tumor-bearing nude mice. J Nucl Med. 2009; 50: 435-43.

Malm M, Kronqvist N, Lindberg H, Gudmundsdotter L, Bass T, Frejd F Y, et al. Inhibiting HER3-mediated tumor cell growth with affibody molecules engineered to low picomolar affinity by position-directed error-prone PCR-like diversification. PLoS One. 2013; 8: e62791.

Covell D G, Barbet J, Holton O D, Black C D V, Weinstein J N, Parker R J. Pharmacokinetics of monoclonal immunoglobulin G1, F(ab')2, and Fab' in mice. Cancer Res. 1986; 46: 3969-78.

Tang Y, Wang J, Scollard D A, Mondal H, Holloway C, Kahn H J, et al. Imaging of HER2/neu-positive BT-474 human breast cancer xenografts in athymic mice using 111In-trastuzumab (Herceptin) Fab fragments. Nucl Med Biol. 2005; 32: 51-8.

Williams L E, Wu a M, Yazaki P J, Liu a, Raubitschek a a, Shively J E, et al. Numerical selection of optimal tumor imaging agents with application to engineered antibodies. Cancer Biother Radiopharm. 2001; 16: 25-35.

SEQUENCE LISTING

<160> NUMBER OF SEQ ID NOS: 127

<210> SEQ ID NO 1
<211> LENGTH: 11
<212> TYPE: PRT
<213> ORGANISM: Artificial Sequence
<220> FEATURE:
<223> OTHER INFORMATION: Synthetic construct

<400> SEQUENCE: 1

Arg Ala Ser Gln Gly Ile Ser Asn Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic construct

<400> SEQUENCE: 2

Ala Ala Ser Ser Leu Gln Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Gln Gln Tyr Gly Trp Leu Pro Leu Thr
1               5

<210> SEQ ID NO 4
<211> LENGTH: 2
<212> TYPE: PRT
<213> ORGANISM: Artificial Sequence
<220> FEATURE:
<223> OTHER INFORMATION: Synthetic construct

<400> SEQUENCE: 4

Ser Tyr
1

<210> SEQ ID NO 5
<211> LENGTH: 17
<212> TYPE: PRT
<213> ORGANISM: Artificial Sequence
<220> FEATURE:
<223> OTHER INFORMATION: Synthetic construct

<400> SEQUENCE: 5

Val Ile Ser Tyr Asp Gly Ser Asn Lys Tyr Tyr Ala Asp Ser Val Lys
1               5                   10                  15

Gly

<210> SEQ ID NO 6
<211> LENGTH: 13
<212> TYPE: PRT
<213> ORGANISM: Artificial Sequence
<220> FEATURE:
<223> OTHER INFORMATION: Synthetic construct

<400> SEQUENCE: 6

Thr Asp Pro Tyr Ser Leu Gly Gly Tyr Tyr Phe Asp Tyr
1               5                   10

<210> SEQ ID NO 7
<211> LENGTH: 107
<212> TYPE: PRT
<213> ORGANISM: Artificial Sequence
<220> FEATURE:
<223> OTHER INFORMATION: Synthetic construct

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Trp Leu Pro Leu
                85                  90                  95

Thr Phe Gly Gln Gly Thr Lys Val Glu Ile Lys
            100                 105

<210> SEQ ID NO 8
<211> LENGTH: 122
<212> TYPE: PRT
<213> ORGANISM: Artificial Sequence
<220> FEATURE:
<223> OTHER INFORMATION: Synthetic construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Pro Tyr Ser Leu Gly Gly Tyr Tyr Phe Asp Tyr Trp
            100                 105                 110

Gly Gln Gly Thr Leu Val Thr Val Ser Ser
        115                 120

<210> SEQ ID NO 9
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 9

Gln Gln Tyr Gly Trp Leu Pro Leu Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic construct

<400> SEQUENCE: 10

Gln Gln Tyr Gly Trp Leu Pro Leu Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic construct

<400> SEQUENCE: 11

Gln Gln Tyr Gly Trp Leu Pro Pro Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic construct

<400> SEQUENCE: 12

Gln Gln Tyr Ala Tyr Pro Leu Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic construct

<400> SEQUENCE: 13

Gln Gln Tyr Gly Tyr Pro Leu Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic construct

<400> SEQUENCE: 14

Gln Gln Tyr Ser Tyr Pro Leu Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 15

Gln Gln Tyr Gly Ser Pro Leu Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic construct

<400> SEQUENCE: 16

Gln Gln Tyr Ser Phe Pro Leu Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic construct

<400> SEQUENCE: 17

Gln Gln Tyr Thr Thr His Pro Leu Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic construct

<400> SEQUENCE: 18

Gln Gln Ala Gly Tyr Arg Pro Leu Thr
1               5

<210> SEQ ID NO 19
<211> LENGTH: 20
<212> TYPE: PRT
<213> ORGANISM: Artificial Sequence
<220> FEATURE:
<223> OTHER INFORMATION: Synthetic construct

<400> SEQUENCE: 19

Ala Arg Ala Pro Ser Tyr Ser Tyr Gly Ser Tyr His Tyr Tyr Tyr
1               5                   10                  15

Tyr Phe Asp Val
            20

<210> SEQ ID NO 20
<211> LENGTH: 21
<212> TYPE: PRT
<213> ORGANISM: Artificial Sequence
<220> FEATURE:
<223> OTHER INFORMATION: Synthetic construct

<400> SEQUENCE: 20

Ala Arg Ala Pro Ser Tyr Ser Tyr Gly Ser Tyr His Tyr Tyr Tyr
1               5                   10                  15

Tyr Tyr Phe Asp Val
            20
```

<210> SEQ ID NO 21
<211> LENGTH: 21
<212> TYPE: PRT
<213> ORGANISM: Artificial Sequence
<220> FEATURE:
<223> OTHER INFORMATION: Synthetic construct

<400> SEQUENCE: 21

Ala Arg Ala Pro Ser Tyr Ser Tyr Gly Ser Tyr His Tyr Tyr Tyr
1               5                   10                  15

Tyr Tyr Phe Asp Tyr
            20

<210> SEQ ID NO 22
<211> LENGTH: 21
<212> TYPE: PRT
<213> ORGANISM: Artificial Sequence
<220> FEATURE:
<223> OTHER INFORMATION: Synthetic construct

<400> SEQUENCE: 22

Ala Arg Ser Pro Ser Tyr Ser Tyr Gly Ser Tyr His Tyr Tyr Tyr
1               5                   10                  15

Tyr Tyr Phe Asp Val
            20

<210> SEQ ID NO 23
<211> LENGTH: 21
<212> TYPE: PRT
<213> ORGANISM: Artificial Sequence
<220> FEATURE:
<223> OTHER INFORMATION: Synthetic construct

<400> SEQUENCE: 23

Ala Arg Ala Pro Ser Tyr His Phe Gly Val His Ser Phe Tyr Tyr
1               5                   10                  15

Tyr Tyr Phe Asp Val
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic construct

<400> SEQUENCE: 24

Ala Arg Ser Pro Tyr Ala Tyr Phe Gly Ser His His Tyr Tyr Tyr
1               5                   10                  15

Tyr Phe Asp Val
            20

<210> SEQ ID NO 25
<211> LENGTH: 21
<212> TYPE: PRT
<213> ORGANISM: Artificial Sequence
<220> FEATURE:
<223> OTHER INFORMATION: Synthetic construct

<400> SEQUENCE: 25

Ala Arg Ser Gly Ser Tyr Tyr His Tyr Gly Trp His Tyr Tyr Tyr
1               5                   10                  15

Tyr Tyr Phe Asp Val
            20

```
<210> SEQ ID NO 26
<211> LENGTH: 21
<212> TYPE: PRT
<213> ORGANISM: Artificial Sequence
<220> FEATURE:
<223> OTHER INFORMATION: Synthetic construct

<400> SEQUENCE: 26

Ala Arg Ser Pro Ser Tyr Tyr Tyr Gly His Asp Tyr Phe Tyr Tyr
1               5                   10                  15

Tyr Tyr Phe Asp Val
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic construct

<400> SEQUENCE: 27

Ala Arg Ser Ser Pro Tyr Phe Tyr Gly Tyr Ser Tyr Tyr Tyr Tyr
1               5                   10                  15

Tyr Phe Asp Val
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic construct

<400> SEQUENCE: 28

Ala Arg Ala Gly Tyr Tyr Val Tyr Gly Ala Ser Ala Tyr Tyr Tyr
1               5                   10                  15

Tyr Met Asp Val
            20

<210> SEQ ID NO 29
<211> LENGTH: 18
<212> TYPE: PRT
<213> ORGANISM: Artificial Sequence
<220> FEATURE:
<223> OTHER INFORMATION: Synthetic construct

<400> SEQUENCE: 29

Ala Arg Gly Gly Ser Ala Trp Tyr Val Ser Tyr Tyr Tyr Tyr Phe
1               5                   10                  15

Asp Val

<210> SEQ ID NO 30
<211> LENGTH: 16
<212> TYPE: PRT
<213> ORGANISM: Artificial Sequence
<220> FEATURE:
<223> OTHER INFORMATION: Synthetic construct

<400> SEQUENCE: 30

Ala Arg Ala Gly Tyr Ala Ser Pro Tyr Tyr Tyr Tyr Phe Asp Tyr
1               5                   10                  15
```

```
<210> SEQ ID NO 31
<211> LENGTH: 17
<212> TYPE: PRT
<213> ORGANISM: Artificial Sequence
<220> FEATURE:
<223> OTHER INFORMATION: Synthetic construct

<400> SEQUENCE: 31

Ala Arg Ala Gly Tyr Ala Ser Pro Tyr Tyr Tyr Tyr Tyr Phe Asp
1               5                   10                  15
Tyr

<210> SEQ ID NO 32
<211> LENGTH: 16
<212> TYPE: PRT
<213> ORGANISM: Artificial Sequence
<220> FEATURE:
<223> OTHER INFORMATION: Synthetic construct

<400> SEQUENCE: 32

Ala Arg Ala Gly Tyr Ala Pro Gly Tyr Tyr Tyr Tyr Phe Asp Tyr
1               5                   10                  15

<210> SEQ ID NO 33
<211> LENGTH: 17
<212> TYPE: PRT
<213> ORGANISM: Artificial Sequence
<220> FEATURE:
<223> OTHER INFORMATION: Synthetic construct

<400> SEQUENCE: 33

Ala Arg Ala Gly Tyr Ala Ser Pro Tyr Tyr Tyr Tyr Tyr Phe Asp
1               5                   10                  15
Val

<210> SEQ ID NO 34
<211> LENGTH: 17
<212> TYPE: PRT
<213> ORGANISM: Artificial Sequence
<220> FEATURE:
<223> OTHER INFORMATION: Synthetic construct

<400> SEQUENCE: 34

Ala Arg Gly Gly Tyr Ala Ser Pro Tyr Tyr Tyr Tyr Tyr Phe Asp
1               5                   10                  15
Val

<210> SEQ ID NO 35
<211> LENGTH: 17
<212> TYPE: PRT
<213> ORGANISM: Artificial Sequence
<220> FEATURE:
<223> OTHER INFORMATION: Synthetic construct

<400> SEQUENCE: 35

Ala Arg Gly Gly Tyr Ala Ser Pro Tyr Tyr Tyr Tyr Tyr Phe Asp
1               5                   10                  15
Tyr

<210> SEQ ID NO 36
<211> LENGTH: 17
<212> TYPE: PRT
<213> ORGANISM: Artificial Sequence
<220> FEATURE:
<223> OTHER INFORMATION: Synthetic construct
```

```
<400> SEQUENCE: 36

Ala Arg Ala Gly Tyr Tyr Ser Pro Tyr Ala Tyr Tyr Tyr Phe Asp
1               5                   10                  15

Tyr

<210> SEQ ID NO 37
<211> LENGTH: 18
<212> TYPE: PRT
<213> ORGANISM: Artificial Sequence
<220> FEATURE:
<223> OTHER INFORMATION: Synthetic construct

<400> SEQUENCE: 37

Ala Arg Gly Gly Ser His Ser Ser Tyr Pro Gly Tyr Tyr Tyr Phe
1               5                   10                  15

Asp Tyr

<210> SEQ ID NO 38
<211> LENGTH: 19
<212> TYPE: PRT
<213> ORGANISM: Artificial Sequence
<220> FEATURE:
<223> OTHER INFORMATION: Synthetic construct

<400> SEQUENCE: 38

Ala Arg Gly Gly Ser His Ser Ser Tyr Pro Gly Tyr Tyr Tyr Tyr
1               5                   10                  15

Phe Asp Tyr

<210> SEQ ID NO 39
<211> LENGTH: 16
<212> TYPE: PRT
<213> ORGANISM: Artificial Sequence
<220> FEATURE:
<223> OTHER INFORMATION: Synthetic construct

<400> SEQUENCE: 39

Ala Arg Gly Gly Tyr Ser Ser Tyr Gly Tyr Tyr Tyr Phe Asp Tyr
1               5                   10                  15

<210> SEQ ID NO 40
<211> LENGTH: 17
<212> TYPE: PRT
<213> ORGANISM: Artificial Sequence
<220> FEATURE:
<223> OTHER INFORMATION: Synthetic construct

<400> SEQUENCE: 40

Ala Arg Gly Gly Tyr Ser Ser Tyr Gly Tyr Tyr Tyr Tyr Phe Asp
1               5                   10                  15

Tyr

<210> SEQ ID NO 41
<211> LENGTH: 18
<212> TYPE: PRT
<213> ORGANISM: Artificial Sequence
<220> FEATURE:
<223> OTHER INFORMATION: Synthetic construct

<400> SEQUENCE: 41

Ala Arg Gly Gly Tyr Ser Ser Tyr Pro Gly Tyr Tyr Tyr Tyr Phe
1               5                   10                  15

Asp Tyr
```

```
<210> SEQ ID NO 42
<211> LENGTH: 19
<212> TYPE: PRT
<213> ORGANISM: Artificial Sequence
<220> FEATURE:
<223> OTHER INFORMATION: Synthetic construct

<400> SEQUENCE: 42

Ala Arg Ala Gly His Val Pro Gly Pro Trp Gly Tyr Tyr Tyr Tyr
1               5                   10                  15

Phe Asp Tyr

<210> SEQ ID NO 43
<211> LENGTH: 18
<212> TYPE: PRT
<213> ORGANISM: Artificial Sequence
<220> FEATURE:
<223> OTHER INFORMATION: Synthetic construct

<400> SEQUENCE: 43

Ala Arg Tyr Tyr Gly Tyr Asp Pro Ser His Tyr Tyr Tyr Tyr Phe
1               5                   10                  15

Asp Tyr

<210> SEQ ID NO 44
<211> LENGTH: 15
<212> TYPE: PRT
<213> ORGANISM: Artificial Sequence
<220> FEATURE:
<223> OTHER INFORMATION: Synthetic construct

<400> SEQUENCE: 44

Ala Arg Thr Asp Pro Tyr Ser Leu Val Gly Tyr Tyr Phe Asp Tyr
1               5                   10                  15

<210> SEQ ID NO 45
<211> LENGTH: 14
<212> TYPE: PRT
<213> ORGANISM: Artificial Sequence
<220> FEATURE:
<223> OTHER INFORMATION: Synthetic construct

<400> SEQUENCE: 45

Ala Arg Thr Asp Pro Tyr Ser Leu Val Tyr Tyr Phe Asp Tyr
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Synthetic construct

<400> SEQUENCE: 46

Ala Arg Thr Asp Gln Tyr Ser Leu Gly Gly Tyr Tyr Phe Asp Tyr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic construct
```

```
<400> SEQUENCE: 47

Ala Arg Thr Asp Ser Tyr Ser Leu Gly Gly Tyr Tyr Phe Asp Tyr
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic construct

<400> SEQUENCE: 48

Ala Arg Thr Asp Pro Tyr Ser Leu Gly Gly Tyr Tyr Phe Gly Tyr
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic construct

<400> SEQUENCE: 49

Ala Arg Thr Asp Pro Tyr Ser Leu Gly Gly Tyr Tyr Phe Asn Tyr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic construct

<400> SEQUENCE: 50

Ala Arg Ala Asp Pro Tyr Ser Leu Gly Gly Tyr Tyr Phe Asp Tyr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic construct

<400> SEQUENCE: 51

Ala Arg Thr Asp Pro Tyr Ser Leu Gly Gly Tyr Tyr Phe Asp Tyr
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic construct

<400> SEQUENCE: 52

Ala Arg Thr Asp Pro Tyr Ser Leu Gly Gly His Tyr Phe Asp Tyr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic construct
```

```
<400> SEQUENCE: 53

Ala Arg Thr Asp Pro Tyr Ser Leu Gly Gly Tyr Tyr Phe Asp Val
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic construct

<400> SEQUENCE: 54

Ala Arg Thr Asp Arg His Ser Leu Gly Gly Tyr Tyr Phe Asp Tyr
1               5                   10                  15

<210> SEQ ID NO 55
<211> LENGTH: 9
<212> TYPE: PRT
<213> ORGANISM: Artificial Sequence
<220> FEATURE:
<223> OTHER INFORMATION: Synthetic construct

<400> SEQUENCE: 55

Ala Arg Gly Gly Tyr Tyr Phe Asp Tyr
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic construct

<400> SEQUENCE: 56

Ala Arg His Gly Ser Tyr Ala Ala Phe Asp Tyr
1               5                   10

<210> SEQ ID NO 57
<211> LENGTH: 20
<212> TYPE: PRT
<213> ORGANISM: Artificial Sequence
<220> FEATURE:
<223> OTHER INFORMATION: Synthetic construct

<400> SEQUENCE: 57

Ala Arg Ala Pro Ser Thr Leu Thr Val Leu Pro Leu Leu Leu Leu
1               5                   10                  15

Leu Leu Arg Arg
            20

<210> SEQ ID NO 58
<211> LENGTH: 15
<212> TYPE: PRT
<213> ORGANISM: Artificial Sequence
<220> FEATURE:
<223> OTHER INFORMATION: Synthetic construct

<400> SEQUENCE: 58

Ala Arg Thr Asp Pro Tyr Ser Leu Gly Gly Tyr Tyr Phe Asp Tyr
1               5                   10                  15

<210> SEQ ID NO 59
<211> LENGTH: 15
<212> TYPE: PRT
<213> ORGANISM: Artificial Sequence
```

```
<220> FEATURE:
<223> OTHER INFORMATION: Synthetic construct

<400> SEQUENCE: 59

Ala Arg Thr Asp Pro Tyr Ser Leu Gly Gly His Tyr Phe Asp Tyr
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic construct

<400> SEQUENCE: 60

Ala Arg Thr Asp Pro Tyr Ser Leu Gly Gly Tyr Tyr Phe Asp Val
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic construct

<400> SEQUENCE: 61

Ala Arg Thr Asp Arg His Ser Leu Gly Gly Tyr Tyr Phe Asp Tyr
1               5                   10                  15

<210> SEQ ID NO 62
<211> LENGTH: 60
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(36)
<223> OTHER INFORMATION: n is A, T, G or C and (25) to (27), (28) to
      (30), (31) to (33) and (34) to (36) encode Y, S, G, T, A, P, H, R,
      E, F, W, V or L

<400> SEQUENCE: 62
ttcgcaactt attactgtca gcaannnnnn nnnnnncctc tgacgttcgg acagggtacc      60

<210> SEQ ID NO 63
<211> LENGTH: 49
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(23)
<223> OTHER INFORMATION: n is A, T, G or C and (21) to (23) encode Y, S,
      G, T, A, P, H, R, E, F, W, V or L;
<220> FEATURE:
<221> NAME/KEY: misc_feature
<222> LOCATION: (24)..(26)
<223> OTHER INFORMATION: n is A, T, G or C and (24) to (26) encode A, G,
      D or Y

<400> SEQUENCE: 63
ccgtctatta ttgtgctcgc nnnnnnttcg actactgggg tcaaggaac      49

<210> SEQ ID NO 64
<211> LENGTH: 52
<212> TYPE: DNA
<213> ORGANISM: Artificial Sequence
```

```
<220> FEATURE:
<223> OTHER INFORMATION: Synthetic construct
<220> FEATURE:
<221> NAME/KEY: misc_feature
<222> LOCATION: (21)..(26)
<223> OTHER INFORMATION: n is A, T, G or C and (21) to (23) and (24) to
      (26) encode Y, S, G, T, A, P, H, R, E, F, W, V or L
<220> FEATURE:
<221> NAME/KEY: misc_feature
<222> LOCATION: (27)..(29)
<223> OTHER INFORMATION: n is A, T, G or C and (27) to (29) encode A, G,
      D or Y

<400> SEQUENCE: 64
ccgtctatta ttgtgctcgc nnnnnnnnnt tcgactactg gggtcaagga ac              52

<210> SEQ ID NO 65
<211> LENGTH: 55
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(29)
<223> OTHER INFORMATION: n is A, T, G or C and (21) to (23), (24) to
      (26) and (27) to (29) encode Y, S, G, T, A, P, H, R, E, F, W, V or
      L
<220> FEATURE:
<221> NAME/KEY: misc_feature
<222> LOCATION: (30)..(32)
<223> OTHER INFORMATION: n is A, T, G or C and (30) to (32) encode A, G,
      D or Y

<400> SEQUENCE: 65
ccgtctatta ttgtgctcgc nnnnnnnnnn nnttcgacta ctggggtcaa ggaac           55

<210> SEQ ID NO 66
<211> LENGTH: 58
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(32)
<223> OTHER INFORMATION: n is A, T, G or C and (21) to (23), (24) to
      (26), (27) to (29) and (30) to (32) encode Y, S, G, T, A, P, H, R,
      E, F, W, V or L
<220> FEATURE:
<221> NAME/KEY: misc_feature
<222> LOCATION: (33)..(35)
<223> OTHER INFORMATION: n is A, T, G or C and (33) to (35) encode A, G,
      D or Y

<400> SEQUENCE: 66
ccgtctatta ttgtgctcgc nnnnnnnnnn nnnnttcga ctactggggt caaggaac         58

<210> SEQ ID NO 67
<211> LENGTH: 61
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(35)
<223> OTHER INFORMATION: n is A, T, G, OR C and (21 to (23), (24) to
      (26), (27) to (29), (30) to (32) and (33) to (35) encode Y, S, G,
      T, A, P, H, R, E, F, W, V or L
```

```
<220> FEATURE:
<221> NAME/KEY: misc_feature
<222> LOCATION: (36)..(38)
<223> OTHER INFORMATION: n is A, T, G, OR C and (36) to (38) encode A,
      G, D or Y

<400> SEQUENCE: 67
ccgtctatta ttgtgctcgc nnnnnnnnnn nnnnnnnntt cgactactgg ggtcaaggaa    60
c                                                                    61

<210> SEQ ID NO 68
<211> LENGTH: 64
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(38)
<223> OTHER INFORMATION: n is A, T, G or C and (21) to (23), (24) to
      (26), (27) to (29), (30) to (32), (33) to (35) and (36) to (38)
      encode Y, S, G, T, A, P, H, R, E, F, W, V or L
<220> FEATURE:
<221> NAME/KEY: misc_feature
<222> LOCATION: (39)..(41)
<223> OTHER INFORMATION: n is A, T, G or C and (39) to (41) encode A, G,
      D or Y

<400> SEQUENCE: 68
ccgtctatta ttgtgctcgc nnnnnnnnnn nnnnnnnnn nttcgactac tggggtcaag     60
gaac                                                                 64

<210> SEQ ID NO 69
<211> LENGTH: 67
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(41)
<223> OTHER INFORMATION: n is A, T, G or C and (21) to (23), (24) to
      (26), (27) to (29), (30) to (32), (33) to (35), (36) to (38) and
      (39) to (41) encode Y, S, G, T, A, P, H, R, E, F, W, V or L
<220> FEATURE:
<221> NAME/KEY: misc_feature
<222> LOCATION: (42)..(44)
<223> OTHER INFORMATION: n is A, T, G or C and (42) to (44) encode A, G,
      D or Y

<400> SEQUENCE: 69
ccgtctatta ttgtgctcgc nnnnnnnnnn nnnnnnnnnn nnnnttcgac tactggggtc    60
aaggaac                                                              67

<210> SEQ ID NO 70
<211> LENGTH: 70
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(44)
<223> OTHER INFORMATION: n is A, T, G or C and (21) to (23), (24) to
      (26), (27) to (29), (30) to (32), (33) to (35), (36) to (38), (39)
      to (41) and (42) to (44) encode Y, S, G, T, A, P, H, R, E, F, W,
      V or L
```

-continued

```
<220> FEATURE:
<221> NAME/KEY: misc_feature
<222> LOCATION: (45)..(47)
<223> OTHER INFORMATION: n is A, T, G or C and (45) to (47) encode A, G,
      D or Y

<400> SEQUENCE: 70
ccgtctatta ttgtgctcgc nnnnnnnnnn nnnnnnnnnn nnnnnnnttc gactactggg      60
gtcaaggaac                                                            70

<210> SEQ ID NO 71
<211> LENGTH: 73
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(47)
<223> OTHER INFORMATION: n is A, T, G or C and (21) to (23), (24) to
      (26), (27) to (29), (30) to (32), (33) to (35), (36) to (38), (39)
      to (41), (42) to (44) and (45) to (47) encode Y, S, G, T, A, P, H,
      R, E, F, W, V or L
<220> FEATURE:
<221> NAME/KEY: misc_feature
<222> LOCATION: (48)..(50)
<223> OTHER INFORMATION: n is A, T, G or C and (48) to (50) encode A, G,
      D or Y

<400> SEQUENCE: 71
ccgtctatta ttgtgctcgc nnnnnnnnnn nnnnnnnnnn nnnnnnnnnn ttcgactact      60
ggggtcaagg aac                                                        73

<210> SEQ ID NO 72
<211> LENGTH: 76
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(50)
<223> OTHER INFORMATION: n is A, T, G, or C and (21) to (23), (24) to
      (26), (27) to (29), (30) to (32), (33) to (35), (36) to (38),
      (39) to (41), (42) to (44), (45) to (47) and (48) to (50) encode
      Y, S, G, T, A, P, H, R, E, F, W, V or L
<220> FEATURE:
<221> NAME/KEY: misc_feature
<222> LOCATION: (51)..(53)
<223> OTHER INFORMATION: n is A, T, G, or C and (51) to (53) encode A,
      G, D or Y

<400> SEQUENCE: 72
ccgtctatta ttgtgctcgc nnnnnnnnnn nnnnnnnnnn nnnnnnnnnn nnnttcgact      60
actggggtca aggaac                                                     76

<210> SEQ ID NO 73
<211> LENGTH: 79
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(41)
<223> OTHER INFORMATION: n is A, T, G or C and (21) to (23), (24) to
      (26), (27) to (29), (30) to (32), (33) to (35), (36) to (38) and
      (39) to (41) encode Y, S, G, A, F, W, H, P or V
```

<400> SEQUENCE: 73
ccgtctatta ttgtgctcgc nnnnnnnnnn nnnnnnnnnn ntactactac tactttgact    60
actggggtca aggaaccct                                                 79

<210> SEQ ID NO 74
<211> LENGTH: 82
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(44)
<223> OTHER INFORMATION: n is A, T, G or C and (21) to (23), (24) to
      (26), (27) to (29), (30) to (32), (33) to (35), (36) to (38), (39)
      to (41) and (42) to (44) encode Y, S, G, A, F, W, H, P or V
<220> FEATURE:
<221> NAME/KEY: misc_feature
<222> LOCATION: (54)..(56)
<223> OTHER INFORMATION: n is A, T, G or C and (54) to (56) encode G or
      Y
<220> FEATURE:
<221> NAME/KEY: misc_feature
<222> LOCATION: (57)..(59)
<223> OTHER INFORMATION: n is A, T, G or C and (54) to (56) encode M or
      F
<220> FEATURE:
<221> NAME/KEY: misc_feature
<222> LOCATION: (63)..(65)
<223> OTHER INFORMATION: n is A, T, G or C and (63) to (65) encode V or
      Y

<400> SEQUENCE: 74
ccgtctatta ttgtgctcgc nnnnnnnnnn nnnnnnnnnn nnntactac tacnnnnnng    60 acnnntgggg tcaaggaacc ct                                             82

<210> SEQ ID NO 75
<211> LENGTH: 85
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(47)
<223> OTHER INFORMATION: n is A, T, G or C and (21) to (23), (24) to
      (26), (27) to (29), (30) to (32), (33) to (35), (36) to (38), (39)
      to (41), (42) to (44) and (45) to (47) encode Y, S, G, A, F, W, H,
      P or V
<220> FEATURE:
<221> NAME/KEY: misc_feature
<222> LOCATION: (57)..(59)
<223> OTHER INFORMATION: n is A, T, G or C and (57) to (59) encode G or
      Y
<220> FEATURE:
<221> NAME/KEY: misc_feature
<222> LOCATION: (60)..(62)
<223> OTHER INFORMATION: n is A, T, G or C and (60) to (62) encode M or
      F
<220> FEATURE:
<221> NAME/KEY: misc_feature
<222> LOCATION: (66)..(68)
<223> OTHER INFORMATION: n is A, T, G or C and (60) to (62) encode V or
      Y

<400> SEQUENCE: 75
ccgtctatta ttgtgctcgc nnnnnnnnnn nnnnnnnnnn nnnnnnntac tactacnnnn    60
nngacnnntg gggtcaagga accct                                          85

<210> SEQ ID NO 76
<211> LENGTH: 88
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(47)
<223> OTHER INFORMATION: n is A, T, G or C and (21) to (23), (24) to (26), (27) to (29), (30) to (32), (33) to (35), (36) to (38), (39) to (41), (42) to (44) and (45) to (47) encode Y, S, G, A, F, W, H, P or V
<220> FEATURE:
<221> NAME/KEY: misc_feature
<222> LOCATION: (60)..(62)
<223> OTHER INFORMATION: n is A, T, G or C and (60) to (62) encode G or Y
<220> FEATURE:
<221> NAME/KEY: misc_feature
<222> LOCATION: (63)..(65)
<223> OTHER INFORMATION: n is A, T, G or C and (60) to (62) encode M or F
<220> FEATURE:
<221> NAME/KEY: misc_feature
<222> LOCATION: (69)..(71)
<223> OTHER INFORMATION: n is A, T, G or C and (60) to (62) encode V or Y

<400> SEQUENCE: 76
ccgtctatta ttgtgctcgc nnnnnnnnnn nnnnnnnnnn nnnnnntac tactactacn      60 nnnnngacnn ntggggtcaa ggaacccct                                        88

<210> SEQ ID NO 77
<211> LENGTH: 91
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(50)
<223> OTHER INFORMATION: n is A, T, G or C and (21) to (23), (24) to (26), (27) to (29), (30) to (32), (33) to (35), (36) to (38), (39) to (41), (42) to (44), (45) to (47) and (48) to (50) encode Y, S, G, A, F, W, H, P or V
<220> FEATURE:
<221> NAME/KEY: misc_feature
<222> LOCATION: (63)..(65)
<223> OTHER INFORMATION: n is A, T, G or C and (63) to (65) encode G or Y
<220> FEATURE:
<221> NAME/KEY: misc_feature
<222> LOCATION: (66)..(68)
<223> OTHER INFORMATION: n is A, T, G or C and (66) to (68) encode M or F

<400> SEQUENCE: 77
ccgtctatta ttgtgctcgc nnnnnnnnnn nnnnnnnnnn nnnnnnnnnn tactactact      60
acnnnnnnga cgtttggggt caaggaaccc t                                     91

<210> SEQ ID NO 78
<211> LENGTH: 94
<212> TYPE: DNA
<213> ORGANISM: Artificial Sequence
<220> FEATURE:
<223> OTHER INFORMATION: Synthetic construct

```
<220> FEATURE:
<221> NAME/KEY: misc_feature
<222> LOCATION: (21)..(53)
<223> OTHER INFORMATION: n is A, T, G or C and (21) to (23), (24) to
      (26), (27) to (29), (30) to (32), (33) to (35), (36) to (38), (39)
      to (41), (42) to (44), (45) to (47), (48) to (50) and (51) to (53)
      encode Y, S, G, A, F, W, H, P or V
<220> FEATURE:
<221> NAME/KEY: misc_feature
<222> LOCATION: (66)..(68)
<223> OTHER INFORMATION: n is A, T, G or C and (66) to (68) encode G or
      Y
<220> FEATURE:
<221> NAME/KEY: misc_feature
<222> LOCATION: (69)..(71)
<223> OTHER INFORMATION: n is A, T, G or C and (69) to (71) encode M or
      F

<400> SEQUENCE: 78
ccgtctatta ttgtgctcgc nnnnnnnnnn nnnnnnnnnn nnnnnnnnnn nnntactact      60
actacnnnnn ngacgtttgg ggtcaaggaa ccct                                   94

<210> SEQ ID NO 79
<211> LENGTH: 97
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(56)
<223> OTHER INFORMATION: n is A, T, G or C and (21) to (23), (24) to
      (26), (27) to (29), (30) to (32), (33) to (35), (36) to (38), (39)
      to (41), (42) to (44), (45) to (47), (48) to (50), (51) to (53)
      and (54) to (56) encode Y, S, G, A, F, W, H, P or V
<220> FEATURE:
<221> NAME/KEY: misc_feature
<222> LOCATION: (69)..(71)
<223> OTHER INFORMATION: n is A, T, G or C and (69) to (71) encode G or
      Y
<220> FEATURE:
<221> NAME/KEY: misc_feature
<222> LOCATION: (72)..(74)
<223> OTHER INFORMATION: n is A, T, G or C and (72) to (74) encode M or
      F

<400> SEQUENCE: 79
ccgtctatta ttgtgctcgc nnnnnnnnnn nnnnnnnnnn nnnnnnnnnn nnnnnntact      60
actactacnn nnnngacgtt tggggtcaag gaaccct                                97

<210> SEQ ID NO 80
<211> LENGTH: 100
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(59)
<223> OTHER INFORMATION: n is A, T, G or C and (21) to (23), (24) to
      (26), (27) to (29), (30) to (32), (33) to (35), (36) to (38), (39)
      to (41), (42) to (44), (45) to (47), (48) to (50), (51) to (53),
      (54) to (56) and (57) to (59) encode Y, S, G, A, F, W, H, P or V
<220> FEATURE:
<221> NAME/KEY: misc_feature
<222> LOCATION: (75)..(77)
<223> OTHER INFORMATION: n is A, T, G or C and  (75) to (77) encode M or
      F
```

<400> SEQUENCE: 80
ccgtctatta ttgtgctcgc nnnnnnnnnn nnnnnnnnnn nnnnnnnnnn nnnnnnnnt      60 actactacta cggannngac gtttggggtc aaggaaccct                           100

<210> SEQ ID NO 81
<211> LENGTH: 103
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(62)
<223> OTHER INFORMATION: n is A, T, G or C and (21) to (23), (24) to
    (26), (27) to (29), (30) to (32), (33) to (35), (36) to (38), (39)
    to (41), (42) to (44), (45) to (47), (48) to (50), (51) to (53),
    (54) to (56), (57) to (59) and (60) to (62) encode Y, S, G, A, F,
    W, H, P or V
<220> FEATURE:
<221> NAME/KEY: misc_feature
<222> LOCATION: (78)..(80)
<223> OTHER INFORMATION: n is A, T, G or C and (78) to (80) encode M or
    F

<400> SEQUENCE: 81
ccgtctatta ttgtgctcgc nnnnnnnnnn nnnnnnnnnn nnnnnnnnnn nnnnnnnnnn      60
nntactacta ctacggannn gacgtttggg gtcaaggaac cct                        103

<210> SEQ ID NO 82
<211> LENGTH: 106
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(65)
<223> OTHER INFORMATION: n is A, T, G or C and (21) to (23), (24) to
    (26), (27) to (29), (30) to (32), (33) to (35), (36) to (38), (39)
    to (41), (42) to (44), (45) to (47), (48) to (50), (51) to (53),
    (54) to (56), (57) to (59), (60) to (62) and (63) to (65) encode
    Y, S, G, A, F,

<400> SEQUENCE: 82
ccgtctatta ttgtgctcgc nnnnnnnnnn nnnnnnnnnn nnnnnnnnnn nnnnnnnnnn      60
nnnnntacta ctactacgga atggacgttt ggggtcaagg aaccct                     106

<210> SEQ ID NO 83
<211> LENGTH: 248
<212> TYPE: PRT
<213> ORGANISM: Artificial Sequence
<220> FEATURE:
<223> OTHER INFORMATION: Synthetic construct

<400> SEQUENCE: 83

Ser Asp Ile Gln Met Thr Gln Ser Pro Ser Ser Leu Ser Ala Ser Val
1               5                  10                  15

Gly Asp Arg Val Thr Ile Thr Cys Arg Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

```
Pro Glu Asp Phe Ala Thr Tyr Tyr Cys Gln Gln Tyr Gly Trp Leu Pro
                85                  90                  95

Leu Thr Phe Gly Gln Gly Thr Lys Val Glu Ile Lys Gly Gly Gly Gly
            100                 105                 110

Ser Gly Gly Gly Gly Ser Gly Gly Gly Ser Glu Ile Ser Glu Val
            115                 120                 125

Gln Leu Val Glu Ser Gly Gly Leu Val Gln Pro Gly Gly Ser Leu
    130                 135                 140

Arg Leu Ser Cys Ala Ala Ser Gly Phe Thr Phe Ser Ser Tyr Gly Met
145                 150                 155                 160

His Trp Val Arg Gln Ala Pro Gly Lys Gly Leu Glu Trp Val Ala Val
                165                 170                 175

Ile Ser Tyr Asp Gly Ser Asn Lys Tyr Tyr Ala Asp Ser Val Lys Gly
                180                 185                 190

Arg Phe Thr Ile Ser Arg Asp Asn Ser Lys Asn Thr Leu Tyr Leu Gln
                195                 200                 205

Met Asn Ser Leu Arg Ala Glu Asp Thr Ala Val Tyr Tyr Cys Ala Arg
            210                 215                 220

Thr Asp Pro Tyr Ser Leu Gly Gly Tyr Tyr Phe Asp Tyr Trp Gly Gln
225                 230                 235                 240

Gly Thr Leu Val Thr Val Ser Ser
                245

<210> SEQ ID NO 84
<211> LENGTH: 238
<212> TYPE: PRT
<213> ORGANISM: Artificial Sequence
<220> FEATURE:
<223> OTHER INFORMATION: Synthetic construct

<400> SEQUENCE: 84

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Gly Trp Leu Pro
                85                  90                  95

Leu Thr Phe Gly Gln Gly Thr Lys Val Glu Ile Lys Gly Gly Gly Gly
            100                 105                 110

Ser Glu Ile Ser Glu Val Gln Leu Val Glu Ser Gly Gly Gly Leu Val
            115                 120                 125

Gln Pro Gly Gly Ser Leu Arg Leu Ser Cys Ala Ala Ser Gly Phe Thr
    130                 135                 140

Phe Ser Ser Tyr Gly Met His Trp Val Arg Gln Ala Pro Gly Lys Gly
145                 150                 155                 160

Leu Glu Trp Val Ala Val Ile Ser Tyr Asp Gly Ser Asn Lys Tyr Tyr
                165                 170                 175

Ala Asp Ser Val Lys Gly Arg Phe Thr Ile Ser Arg Asp Asn Ser Lys
            180                 185                 190
```

```
Asn Thr Leu Tyr Leu Gln Met Asn Ser Leu Arg Ala Glu Asp Thr Ala
            195                 200                 205

Val Tyr Tyr Cys Ala Arg Thr Asp Pro Tyr Ser Leu Gly Gly Tyr Tyr
        210                 215                 220

Phe Asp Tyr Trp Gly Gln Gly Thr Leu Val Thr Val Ser Ser
225                 230                 235

<210> SEQ ID NO 85
<211> LENGTH: 226
<212> TYPE: PRT
<213> ORGANISM: Artificial Sequence
<220> FEATURE:
<223> OTHER INFORMATION: Synthetic construct

<400> SEQUENCE: 85

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Gly Trp Leu Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Ser Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Ser Asp Tyr Lys Asp Asp Asp
    210                 215                 220

Asp Lys
225

<210> SEQ ID NO 86
<211> LENGTH: 242
<212> TYPE: PRT
<213> ORGANISM: Artificial Sequence
<220> FEATURE:
<223> OTHER INFORMATION: Synthetic construct

<400> SEQUENCE: 86

Glu Ile Ser Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30
```

Ser Ser Tyr Gly Met His Trp Val Arg Gln Ala Pro Gly Lys Gly Leu
            35                  40                  45

Glu Trp Val Ala Val Ile Ser Tyr Asp Gly Ser Asn Lys Tyr Tyr Ala
 50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg Thr Asp Pro Tyr Ser Leu Gly Tyr Tyr Phe
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
            210                 215                 220

Pro Lys Ser Cys Asp Lys Thr His Thr Gly Gly Ser His His His His
225                 230                 235                 240

His His

<210> SEQ ID NO 87
<211> LENGTH: 370
<212> TYPE: PRT
<213> ORGANISM: Artificial Sequecne
<220> FEATURE:
<223> OTHER INFORMATION: Synthetic construct

<400> SEQUENCE: 87

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Gly Trp Leu Pro
                85                  90                  95

Leu Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Ile Ser Glu Val
        115                 120                 125

Gln Leu Val Glu Ser Gly Gly Gly Leu Val Gln Pro Gly Gly Ser Leu
    130                 135                 140

```
Arg Leu Ser Cys Ala Ala Ser Gly Phe Thr Phe Ser Ser Tyr Gly Met
145                 150                 155                 160

His Trp Val Arg Gln Ala Pro Gly Lys Gly Leu Glu Trp Val Ala Val
                165                 170                 175

Ile Ser Tyr Asp Gly Ser Asn Lys Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Arg
    210                 215                 220

Thr Asp Pro Tyr Ser Leu Gly Tyr Tyr Phe Asp Tyr Trp Gly Gln
225                 230                 235                 240

Gly Thr Leu Val Thr Val Ser Ser Glu Pro Lys Ser Cys Asp Lys Thr
                245                 250                 255

His Thr Cys Pro Pro Cys Pro Gly Gln Pro Arg Glu Pro Gln Val Tyr
            260                 265                 270

Thr Leu Pro Pro Ser Arg Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
    370

<210> SEQ ID NO 88
<211> LENGTH: 480
<212> TYPE: PRT
<213> ORGANISM: Artificial Sequence
<220> FEATURE:
<223> OTHER INFORMATION: Synthetic construct

<400> SEQUENCE: 88

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Asn
                20                  25                  30

Tyr Leu Ala Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
        50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Gly Trp Leu Pro
                85                  90                  95

Leu Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Ile Ser Glu Val
        115                 120                 125
```

```
Gln Leu Val Glu Ser Gly Gly Gly Leu Val Gln Pro Gly Gly Ser Leu
    130                 135                 140
Arg Leu Ser Cys Ala Ala Ser Gly Phe Thr Phe Ser Ser Tyr Gly Met
145                 150                 155                 160
His Trp Val Arg Gln Ala Pro Gly Lys Gly Leu Glu Trp Val Ala Val
                165                 170                 175
Ile Ser Tyr Asp Gly Ser Asn Lys Tyr Tyr Ala Asp Ser Val Lys Gly
            180                 185                 190
Arg Phe Thr Ile Ser Arg Asp Asn Ser Lys Asn Thr Leu Tyr Leu Gln
        195                 200                 205
Met Asn Ser Leu Arg Ala Glu Asp Thr Ala Val Tyr Tyr Cys Ala Arg
    210                 215                 220
Thr Asp Pro Tyr Ser Leu Gly Gly Tyr Tyr Phe Asp Tyr Trp Gly Gln
225                 230                 235                 240
Gly Thr Leu Val Thr Val Ser Ser Glu Pro Lys Ser Cys Asp Lys Thr
                245                 250                 255
His Thr Cys Pro Pro Cys Pro Ala Pro Glu Leu Leu Gly Gly Pro Ser
            260                 265                 270
Val Phe Leu Phe Pro Pro Lys Pro Lys Asp Thr Leu Met Ile Ser Arg
        275                 280                 285
Thr Pro Glu Val Thr Cys Val Val Val Asp Val Ser His Glu Asp Pro
    290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Ala Leu Pro Ala Pro Ile Glu Lys Thr
        355                 360                 365
Ile Ser Lys Ala Lys Gly Gln Pro Arg Glu Pro Gln Val Tyr Thr Leu
    370                 375                 380
Pro Pro Ser Arg Glu Glu Met Thr Lys Asn Gln Val Ser Leu Thr Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Lys Leu Thr Val Asp Lys Ser
        435                 440                 445
Arg Trp Gln Gln Gly Asn Val Phe Ser Cys Ser Val Met His Glu Ala
    450                 455                 460
Leu His Asn His Tyr Thr Gln Lys Ser Leu Ser Leu Ser Pro Gly Lys
465                 470                 475                 480

<210> SEQ ID NO 89
<211> LENGTH: 215
<212> TYPE: PRT
<213> ORGANISM: Artificial Sequence
<220> FEATURE:
<223> OTHER INFORMATION: Synthethic construct
```

```
<400> SEQUENCE: 89

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Gly Trp Leu Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 90
<211> LENGTH: 455
<212> TYPE: PRT
<213> ORGANISM: Artificial Sequence
<220> FEATURE:
<223> OTHER INFORMATION: Synthetic contstruct

<400> SEQUENCE: 90

Glu Ile Ser Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Gly Met His Trp Val Arg Gln Ala Pro Gly Lys Gly Leu
        35                  40                  45

Glu Trp Val Ala Val Ile Ser Tyr Asp Gly Ser Asn Lys Tyr Tyr Ala
50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg Thr Asp Pro Tyr Ser Leu Gly Gly Tyr Tyr Phe
            100                 105                 110

Asp Tyr Trp Gly Gln Gly Thr Leu Val Thr Val Ser Ser Ala Ser Thr
        115                 120                 125
```

```
Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 91
<211> LENGTH: 8
<212> TYPE: PRT
<213> ORGANISM: Artificial Sequence
<220> FEATURE:
<223> OTHER INFORMATION: Synthetic construct

<400> SEQUENCE: 91

Gln Gln Tyr Ser Tyr Pro Leu Thr
1               5
```

```
<210> SEQ ID NO 92
<211> LENGTH: 21
<212> TYPE: PRT
<213> ORGANISM: Artificial Sequence
<220> FEATURE:
<223> OTHER INFORMATION: Synthetic construct

<400> SEQUENCE: 92

Ala Arg Ala Pro Ser Tyr Ser Tyr Gly Ser Tyr His Tyr Tyr Tyr
1               5                   10                  15

Tyr Tyr Phe Asp Val
            20

<210> SEQ ID NO 93
<211> LENGTH: 9
<212> TYPE: PRT
<213> ORGANISM: Artificial Sequence
<220> FEATURE:
<223> OTHER INFORMATION: Synthetic construct

<400> SEQUENCE: 93

Gln Gln Gly Thr Tyr Leu Pro Leu Thr
1               5

<210> SEQ ID NO 94
<211> LENGTH: 15
<212> TYPE: PRT
<213> ORGANISM: Artificial Sequence
<220> FEATURE:
<223> OTHER INFORMATION: Synthetic construct

<400> SEQUENCE: 94

Ala Arg Thr Tyr Ser Tyr Ala Ser Arg Gly Trp Tyr Phe Asp Tyr
1               5                   10                  15

<210> SEQ ID NO 95
<211> LENGTH: 9
<212> TYPE: PRT
<213> ORGANISM: Artificial Sequence
<220> FEATURE:
<223> OTHER INFORMATION: Synthetic construct

<400> SEQUENCE: 95

Gln Gln Ser Tyr Arg Ser Pro Leu Thr
1               5

<210> SEQ ID NO 96
<211> LENGTH: 15
<212> TYPE: PRT
<213> ORGANISM: Artificial Sequence
<220> FEATURE:
<223> OTHER INFORMATION: Synthetic construct

<400> SEQUENCE: 96

Ala Arg Ser Gly Arg Tyr Gly Thr Tyr Lys Gly Asp Phe Asp Tyr
1               5                   10                  15

<210> SEQ ID NO 97
<211> LENGTH: 9
<212> TYPE: PRT
<213> ORGANISM: Artificial Sequence
<220> FEATURE:
<223> OTHER INFORMATION: Synthetic construct

<400> SEQUENCE: 97

Gln Gln Ser Gly Ser Ser Pro Leu Thr
1               5
```

-continued

```
<210> SEQ ID NO 98
<211> LENGTH: 14
<212> TYPE: PRT
<213> ORGANISM: Artificial Sequence
<220> FEATURE:
<223> OTHER INFORMATION: Synthetic construct

<400> SEQUENCE: 98

Ala Ser His Ser Tyr Val Tyr Thr Ala Gly Tyr Phe Asp Tyr
1               5                   10

<210> SEQ ID NO 99
<211> LENGTH: 9
<212> TYPE: PRT
<213> ORGANISM: Artificial Sequence
<220> FEATURE:
<223> OTHER INFORMATION: Synthetic construct

<400> SEQUENCE: 99

Gln Gln Ser Leu Ala Thr Pro Leu Thr
1               5

<210> SEQ ID NO 100
<211> LENGTH: 13
<212> TYPE: PRT
<213> ORGANISM: Artificial Sequence
<220> FEATURE:
<223> OTHER INFORMATION: Synthetic construct

<400> SEQUENCE: 100

Ala Arg Ser Glu Tyr Gly Thr Ser Gly Tyr Phe Asp Tyr
1               5                   10

<210> SEQ ID NO 101
<211> LENGTH: 106
<212> TYPE: PRT
<213> ORGANISM: Artificial Sequence
<220> FEATURE:
<223> OTHER INFORMATION: Synthetic construct

<400> SEQUENCE: 101

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Thr Gly Val Pro Asp Arg Phe Thr Gly Asn
    50                  55                  60

Arg Ser Gly Thr Asp Phe Thr Phe Thr Ile Ser Ser Val Gln Ala Glu
65                  70                  75                  80

Asp Leu Ala Val Tyr Tyr Cys Gln Gln His Tyr Thr Thr Pro Pro Thr
                85                  90                  95

Phe Gly Gly Gly Thr Lys Leu Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Synthetic construct
```

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 103
<211> LENGTH: 107
<212> TYPE: PRT
<213> ORGANISM: Artificial Sequence
<220> FEATURE:
<223> OTHER INFORMATION: Synthetic construct

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 104
<211> LENGTH: 101
<212> TYPE: PRT
<213> ORGANISM: Artificial Sequence
<220> FEATURE:
<223> OTHER INFORMATION: Synthetic construct

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

```
Glu Asp Phe Ala Thr Tyr Tyr Cys Gln Gln Thr Phe Gly Gln Gly Thr
                85                  90                  95

Lys Val Glu Ile Lys
            100

<210> SEQ ID NO 105
<211> LENGTH: 103
<212> TYPE: PRT
<213> ORGANISM: Artificial Sequence
<220> FEATURE:
<223> OTHER INFORMATION: Synthetic construct

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Leu Thr Phe Gly Gln
                85                  90                  95

Gly Thr Lys Val Glu Ile Lys
            100

<210> SEQ ID NO 106
<211> LENGTH: 120
<212> TYPE: PRT
<213> ORGANISM: Artificial Sequence
<220> FEATURE:
<223> OTHER INFORMATION: Synthetic construct

<400> SEQUENCE: 106

Glu Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser
        115                 120

<210> SEQ ID NO 107
<211> LENGTH: 119
<212> TYPE: PRT
<213> ORGANISM: Artificial Sequence
<220> FEATURE:
<223> OTHER INFORMATION: Synthetic construct
```

```
<400> SEQUENCE: 107

Glu Val Gln Leu Val Glu Trp Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Arg Asp Asp Ser Lys Asn Thr Leu Tyr
65                  70                  75                  80

Gln Met Asn Ser Leu Arg Ala Glu Asp Thr Ala Val Tyr Tyr Cys Ala
                85                  90                  95

Arg Trp Gly Gly Asp Gly Phe Tyr Ala Met Asp Val Trp Gly Gln Gly
            100                 105                 110

Thr Leu Val Thr Val Ser Ser
        115

<210> SEQ ID NO 108
<211> LENGTH: 119
<212> TYPE: PRT
<213> ORGANISM: Artificial Sequence
<220> FEATURE:
<223> OTHER INFORMATION: Synthetic construct

<400> SEQUENCE: 108

Glu Val Gln Leu Val Glu Trp Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Gln Met Asn Ser Leu Arg Ala Glu Asp Thr Ala Val Tyr Tyr Cys Ser
                85                  90                  95

Arg Trp Gly Gly Asp Gly Phe Tyr Ala Met Asp Tyr Trp Gly Gln Gly
            100                 105                 110

Thr Leu Val Thr Val Ser Ser
        115

<210> SEQ ID NO 109
<211> LENGTH: 96
<212> TYPE: PRT
<213> ORGANISM: Artificial Sequence
<220> FEATURE:
<223> OTHER INFORMATION: Synthetic construct

<400> SEQUENCE: 109

Glu Val Gln Leu Val Glu Trp Gly Gly Gly Leu Val Gln Pro Gly Gly
1               5                   10                  15

Ser Leu Arg Leu Ser Cys Ala Ala Ser Gly Phe Asn His Trp Val Arg
            20                  25                  30

Gln Ala Pro Gly Lys Gly Leu Glu Trp Val Ala Ile Thr Tyr Ala Asp
        35                  40                  45
```

Ser Val Lys Gly Arg Phe Thr Ile Ser Ala Asp Thr Ser Lys Asn Thr
        50                  55                  60

Ala Tyr Gln Met Asn Ser Leu Arg Ala Glu Asp Thr Ala Val Tyr Tyr
65                  70                  75                  80

Cys Ala Arg Asp Tyr Trp Gly Gln Gly Thr Leu Val Thr Val Ser Ser
                85                  90                  95

<210> SEQ ID NO 110
<211> LENGTH: 104
<212> TYPE: PRT
<213> ORGANISM: Artificial Sequence
<220> FEATURE:
<223> OTHER INFORMATION: Synthetic construct

<400> SEQUENCE: 110

Glu Val Gln Leu Val Glu Trp Gly Gly Gly Leu Val Gln Pro Gly Gly
1               5                   10                  15

Ser Leu Arg Leu Ser Cys Ala Ala Ser Gly Phe Asn His Trp Val Arg
            20                  25                  30

Gln Ala Pro Gly Lys Gly Leu Glu Trp Val Ala Val Ile Ser Tyr Asp
        35                  40                  45

Gly Ser Asn Lys Tyr Tyr Ala Asp Ser Val Lys Gly Arg Phe Thr Ile
    50                  55                  60

Ser Arg Asp Asn Ser Lys Asn Thr Leu Tyr Gln Met Asn Ser Leu Arg
65                  70                  75                  80

Ala Glu Asp Thr Ala Val Tyr Tyr Cys Ala Arg Asp Tyr Trp Gly Gln
                85                  90                  95

Gly Thr Leu Val Thr Val Ser Ser
            100

<210> SEQ ID NO 111
<211> LENGTH: 11
<212> TYPE: PRT
<213> ORGANISM: Artificial Sequence
<220> FEATURE:
<223> OTHER INFORMATION: Synthetic cosntruct

<400> SEQUENCE: 111

Arg Ala Ser Gln Gly Ile Ser Asn Tyr Leu Ala
1               5                   10

<210> SEQ ID NO 112
<211> LENGTH: 8
<212> TYPE: PRT
<213> ORGANISM: Artificial Sequence
<220> FEATURE:
<223> OTHER INFORMATION: Synthetic construct

<400> SEQUENCE: 112

Tyr Ala Ala Ser Ser Leu Gln Ser
1               5

<210> SEQ ID NO 113
<211> LENGTH: 13
<212> TYPE: PRT
<213> ORGANISM: Artificial Sequence
<220> FEATURE:
<223> OTHER INFORMATION: Synthetic construct

<400> SEQUENCE: 113

Ala Ala Ser Gln Phe Thr Phe Ser Ser Tyr Gly Met His
1               5                   10

```
<210> SEQ ID NO 114
<211> LENGTH: 10
<212> TYPE: PRT
<213> ORGANISM: Artificial Sequence
<220> FEATURE:
<223> OTHER INFORMATION: Synthetic construct

<400> SEQUENCE: 114

Val Ile Ser Tyr Asp Gly Ser Asn Lys Tyr
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Synthetic construct

<400> SEQUENCE: 115

Gln Gln Tyr Gly Trp Leu Pro Leu Thr
1               5

<210> SEQ ID NO 116
<211> LENGTH: 15
<212> TYPE: PRT
<213> ORGANISM: Artificial Sequence
<220> FEATURE:
<223> OTHER INFORMATION: Synthetic construct

<400> SEQUENCE: 116

Ala Arg Thr Asp Pro Tyr Ser Leu Gly Gly Tyr Tyr Phe Asp Tyr
1               5                   10                  15

<210> SEQ ID NO 117
<211> LENGTH: 6
<212> TYPE: PRT
<213> ORGANISM: Artificial Sequence
<220> FEATURE:
<223> OTHER INFORMATION: Synthetic construct

<400> SEQUENCE: 117

Gln Gly Ile Ser Asn Tyr
1               5

<210> SEQ ID NO 118
<211> LENGTH: 3
<212> TYPE: PRT
<213> ORGANISM: Artificial Sequence
<220> FEATURE:
<223> OTHER INFORMATION: Synthetic construct

<400> SEQUENCE: 118

Ala Ala Ser
1

<210> SEQ ID NO 119
<211> LENGTH: 9
<212> TYPE: PRT
<213> ORGANISM: Artificial Sequence
<220> FEATURE:
<223> OTHER INFORMATION: Synthetic construct

<400> SEQUENCE: 119

Gln Gln Tyr Gly Trp Leu Pro Leu Thr
1               5
```

```
<210> SEQ ID NO 120
<211> LENGTH: 8
<212> TYPE: PRT
<213> ORGANISM: Artificial Sequence
<220> FEATURE:
<223> OTHER INFORMATION: Synthetic construct

<400> SEQUENCE: 120

Gly Phe Thr Phe Ser Ser Tyr Gly
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic construct

<400> SEQUENCE: 121

Ile Ser Tyr Asp Gly Ser Asn Lys
1               5

<210> SEQ ID NO 122
<211> LENGTH: 15
<212> TYPE: PRT
<213> ORGANISM: Artificial Sequence
<220> FEATURE:
<223> OTHER INFORMATION: Synthetic construct

<400> SEQUENCE: 122

Ala Arg Thr Asp Pro Tyr Ser Leu Gly Gly Tyr Tyr Phe Asp Tyr
1               5                   10                  15

<210> SEQ ID NO 123
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X is G or S
<220> FEATURE:
<221> NAME/KEY: MISC_FEATURE
<222> LOCATION: (3)..(3)
<223> OTHER INFORMATION: X is W or Y

<400> SEQUENCE: 123

Tyr Xaa Xaa Leu
1

<210> SEQ ID NO 124
<211> LENGTH: 10
<212> TYPE: PRT
<213> ORGANISM: Artificial Sequence
<220> FEATURE:
<223> OTHER INFORMATION: Synethic construct

<400> SEQUENCE: 124

Thr Asp Pro Tyr Ser Leu Gly Gly Tyr Tyr
1               5                   10

<210> SEQ ID NO 125
<211> LENGTH: 4
<212> TYPE: PRT
<213> ORGANISM: Artificial Sequence
<220> FEATURE:
<223> OTHER INFORMATION: Synthetic contruct
```

```
<400> SEQUENCE: 125

Tyr Phe Asp Tyr
1

<210> SEQ ID NO 126
<211> LENGTH: 8
<212> TYPE: PRT
<213> ORGANISM: Artificial Sequence
<220> FEATURE:
<223> OTHER INFORMATION: Synthetic construct

<400> SEQUENCE: 126

Tyr Tyr Tyr Tyr Tyr Phe Asp Val
1               5

<210> SEQ ID NO 127
<211> LENGTH: 5
<212> TYPE: PRT
<213> ORGANISM: Artificial Sequence
<220> FEATURE:
<223> OTHER INFORMATION: Synthetic construct

<400> SEQUENCE: 127

Gly Gly Gly Gly Ser
1               5
```

The invention claimed is:

1. An antibody or antigen binding fragment thereof that specifically binds HER3 comprising:
a light chain variable region and a heavy chain variable region, the light chain variable region comprising complementarity determining region CDR-L1, CDR-L2 and CDR-L3 and the heavy chain variable region comprising complementarity determining region CDR-H1, CDR-H2 and CDR-H3, wherein
CDR-L1 comprises the amino acid sequence set out in SEQ ID NO: 1, CDR-L2 comprises the amino acid sequence set out in SEQ ID NO: 2, CDR-L3 comprises the amino acid sequence set out in SEQ ID NO: 3, CDR-H1 comprises the amino acid sequence set out in SEQ ID NO: 4, CDR-H2 comprises the amino acid sequence set out in SEQ ID NO: 5 and CDR-H3 comprises the amino acid sequence set out in SEQ ID NO: 6, as defined by Kabat numbering; or
CDR-L1 comprises the amino acid sequence set out in SEQ ID NO: 117, CDR-L2 comprises the amino acid sequence set out in SEQ ID NO: 118, CDR-L3 comprises the amino acid sequence set out in SEQ ID NO: 119, CDR-H1 comprises the amino acid sequence set out in SEQ ID NO: 120, SEQ ID NO: 121 and CDR-H3 comprises the amino acid sequence set out in SEQ ID NO: 122, as defined by IMGT numbering.

2. The antibody or antigen binding fragment of claim 1, wherein the HER3 is human HER3.

3. The antibody or antigen binding fragment of claim 1, wherein the light chain variable region comprises (a) the amino acid sequence of SEQ ID NO: 7 or an amino acid sequence having at least 70% sequence identity to the framework regions of SEQ ID NO: 7 and (b) the amino acid sequence of SEQ ID NO: 8 or an amino acid sequence having at least 70% sequence identity to the framework regions of SEQ ID NO: 8.

4. The antibody or antigen binding fragment of claim 1, wherein the antibody or binding fragment specifically binds HER3 with a dissociation constant ($K_D$) less than or about 2.14 nM and/or wherein the antibody or binding fragment does not inhibit the growth of HER3 expressing cells.

5. The antibody or antigen binding fragment of claim 1, wherein the antigen binding fragment is selected from the group consisting of a fragment antigen-binding Fab, a single-chain Fv (scFv), a scFv-CH3, a scFv-Fc, a diabody, a bispecific antibody, a phage-Fab and a phage-scFv.

6. The antibody or antigen binding fragment of claim 1, wherein the antibody or antigen binding fragment is an IgG molecule.

7. An immunoconjugate comprising (1) the antibody or antigen binding fragment of claim 1 attached to (2) an effector agent.

8. The immunoconjugate of claim 7, wherein the effector agent is a detection agent or a toxin.

9. A composition comprising the antibody or antigen binding fragment of claim 1.

10. A method of detecting a HER3 expressing cell in a sample, the method comprising:
a) contacting the sample with
(i) the antibody or antigen binding fragment of claim 1, under conditions to form an antibody:HER3 complex; and
b) detecting the antibody:HER3 complex.

11. The method of claim 10, wherein the antibody or antigen binding fragment of claim 1 is conjugated to a fluorescent compound or a radionuclide.

12. A method of detecting a HER3 expressing cell in a subject, the method comprising:
a) administering
the antibody or antigen binding fragment of claim 1, wherein the antibody or antigen binding fragment is conjugated to a detection agent, and
b) subjecting said subject to imaging.

13. The method of claim 12, wherein the imaging comprises SPECT or PET imaging.

14. The method of claim 12, wherein the antibody or antigen binding fragment is administered by intravenous injection.

\* \* \* \* \*